United States Patent
Jiang et al.

(12)

(10) Patent No.: US 10,407,400 B2
(45) Date of Patent: Sep. 10, 2019

(54) COMPOUNDS, COMPOSITIONS, AND METHODS FOR MODULATING SWEET TASTE

(71) Applicant: Chromocell Corporation, North Brunswick, NJ (US)

(72) Inventors: Deshou Jiang, East Brunswick, NJ (US); Hao Zhou, Paramus, NJ (US); Stuart Hayden, Manalapan, NJ (US)

(73) Assignee: Chromocell Corporation, North Brunswick, NJ (US)

( * ) Notice: Subject to any disclaimer, the term of this patent is extended or adjusted under 35 U.S.C. 154(b) by 0 days.

(21) Appl. No.: 15/543,229

(22) PCT Filed: Jan. 13, 2016

(86) PCT No.: PCT/US2016/013296
§ 371 (c)(1),
(2) Date: Jul. 12, 2017

(87) PCT Pub. No.: WO2016/115278
PCT Pub. Date: Jul. 21, 2016

(65) Prior Publication Data
US 2018/0002306 A1    Jan. 4, 2018

Related U.S. Application Data

(60) Provisional application No. 62/102,790, filed on Jan. 13, 2015, provisional application No. 62/258,931, filed on Nov. 23, 2015.

(51) Int. Cl.
| | | |
|---|---|---|
| *C07D 239/38* | (2006.01) | |
| *C07D 311/20* | (2006.01) | |
| *A23L 27/30* | (2016.01) | |
| *C07D 311/42* | (2006.01) | |
| *A61K 8/49* | (2006.01) | |
| *A61Q 11/00* | (2006.01) | |
| *A23L 27/00* | (2016.01) | |
| *A23L 33/125* | (2016.01) | |
| *A61K 47/22* | (2006.01) | |
| *A61Q 19/00* | (2006.01) | |

(52) U.S. Cl.
CPC .......... *C07D 311/20* (2013.01); *A23L 27/30* (2016.08); *A23L 27/86* (2016.08); *A23L 27/88* (2016.08); *A23L 33/125* (2016.08); *A61K 8/498* (2013.01); *A61K 47/22* (2013.01); *A61Q 11/00* (2013.01); *A61Q 19/00* (2013.01); *C07D 311/42* (2013.01); *A23V 2002/00* (2013.01)

(58) Field of Classification Search
CPC .................................................... C07D 311/74
See application file for complete search history.

(56) References Cited

U.S. PATENT DOCUMENTS

| | | | |
|---|---|---|---|
| 9,131,719 B2 | 9/2015 | Backes et al. | |
| 9,315,496 B2 | 4/2016 | Zhang et al. | |
| 2013/0078192 A1* | 3/2013 | Backes .................. | A61K 8/498 424/49 |
| 2013/0084252 A1 | 4/2013 | Backes et al. | |
| 2014/0113911 A1 | 4/2014 | Zhang et al. | |

FOREIGN PATENT DOCUMENTS

| | | |
|---|---|---|
| CN | 102206214 A | 10/2011 |
| CN | 102206214 B | 3/2014 |
| EP | 2570036 A1 | 3/2013 |
| EP | 2698369 A1 | 2/2014 |
| EP | 2570036 B1 | 6/2014 |
| WO | WO-2012136147 | 10/2012 |

OTHER PUBLICATIONS

S. Akoi et al., 61 Tetrahedron, 9291-9297 (2005).*
CAS Registry No. RN 1945993-01-0 (Jul. 5, 2016).*
CAS Abstract and Indexed Compounds US 2013/0078192 (2013).*
R. Suthunuru et al., 1 Arkivoc, 138-145 (2004).*
Singh, I. "Synthetic and Novel Biocatalytic Resolution Studies on (±)-5/6/7-Acetoxy-4-aryl-3, 4- dihydrocoumarins", Bioorganic and Medicinal Chemisrty, 2003, vol. 11, No. 4, pp. 529-538.
Aoki, S. A convenient synthesis of dihydrocoumarins from phenols and cinnamic acid derivatives Department of Chemistry, Saga Univ, 61 (2005) 9291-9297.

* cited by examiner

*Primary Examiner* — Alexander R Pagano

(57) ABSTRACT

The present disclosure provides edible compositions comprising a flavor-grade sweet taste modulator or a combination of flavor-grade sweet taste modulators or a flavor-grade bitter taste blocker or a combination of flavor-grade bitter taste blockers of the present disclosure, food products comprising such edible compositions and methods of preparing such food products. The present disclosure also provides methods of reducing the amount of sugar in a food product, methods of reducing the caloric intake in a diet, and methods of enhancing sweet taste or blocking a bitter taste in a food product.

11 Claims, No Drawings

COMPOUNDS, COMPOSITIONS, AND METHODS FOR MODULATING SWEET TASTE

CROSS-REFERENCE TO RELATED APPLICATION

This application is a national phase filing under 35 U.S.C. § 371 of International Application No. PCT/US2016/013296 filed Jan. 13, 2016, which claims priority from U.S. application No. 62/102,790, filed Jan. 13, 2015 and U.S. application No. 62/258,931, filed Nov. 23, 2015, the entire contents of each are hereby incorporated by reference herein.

FIELD OF THE INVENTION

The present disclosure relates to flavor in edible compositions.

BACKGROUND OF THE INVENTION

There is an increasing demand worldwide to have broader available choices of reduced sugar content in foods and beverages, whether for taste preference, lifestyle reasons or for certain individuals (e.g., diabetic patients) for health-related goals. Accordingly, the health benefits associated with the reduction of sugar content in foods and beverages are desirable. The use of non-caloric artificial and natural high-potency sweeteners to reduce the level of sweeteners such as caloric and non-caloric sweeteners in foods is limited due to temporal and/or flavor issues, e.g., slow onset of sweetness, sweetness linger, bitter, metallic or licorice taste.

The market for compounds or food products for which nothing artificial or synthetic has been included in, has been added to, or has been used to synthesize the compounds or food products is growing. A 2014 analysis estimated that almost 50% of U.S. consumers look for a mention of no artificial ingredients before purchasing a product (See, Tully & Holland, "Flavors & Fragrances Industry Update," August 2014). It is, therefore, desirable to provide compounds, food products, consumer products and pharmaceuticals which allow for the use of reduced amounts of caloric sweeteners (e.g., sugars) while maintaining desirable sweet taste and avoiding the flavor issues associated with sugar substitutes that do not include or are not prepared from artificial or synthetic components. Development of processes that do not utilize artificial or synthetic materials to generate such compounds, food products, consumer products and pharmaceuticals is needed.

SUMMARY OF THE INVENTION

The present disclosure provides methods of preparing flavor-grade compounds that enhance sweet taste, edible compositions comprising such flavor-grade compounds, and methods of preparing such edible compositions. The present disclosure also provides methods of reducing the amount of a sweetener in an edible composition. The present disclosure further provides a method of enhancing, modulating or potentiating the sweet taste of an edible composition, such as a food, consumer or pharmaceutical product, in a subject. The present disclosure also provides a method of modulating, particularly enhancing or potentiating the activation of a sweet taste receptor. A further aspect of the present disclosure provides flavor-grade compounds or mixtures thereof for masking or reducing unpleasant taste sensations, in particular for masking or reducing the bitter taste sensation of a bitter-tastant.

One aspect of the present disclosure provides a method for preparing flavor-grade compounds for modulating sweet taste (e.g., enhancing sweet taste) of a sweet tastant. In some embodiments, the flavor-grade compound is a neoflavonoid compound. In some embodiments, the flavor-grade neoflavonoid compound has a molecular weight less than about 1000, about 500, or about 300 Daltons. In certain embodiments, the flavor-grade neoflavonoid compound is a compound of Formula (I), or a comestibly or biologically acceptable salt or derivative thereof, or an enantiomer thereof, or a combination of any of the foregoing compounds. In certain embodiments, the flavor-grade neoflavonoid compound is flavor-grade Compound 1 or 4, or a comestibly or biologically acceptable salt, derivative, or enantiomer thereof. In certain embodiments, the flavor-grade neoflavonoid compound is flavor-grade Compound 2, 3, 5, or 6, or a comestibly or biologically acceptable salt or derivative thereof. In certain embodiments, the flavor-grade neoflavonoid compound is a combination of flavor-grade Compounds 1-3, or comestibly or biologically acceptable salts or derivatives thereof. In certain embodiments wherein the flavor-grade neoflavonoid compound is a combination of flavor-grade Compounds 1-3, or comestibly or biologically acceptable salts or derivatives thereof, the compound further comprises a combination of flavor-grade Compounds 4-6, or comestibly or biologically acceptable salts or derivatives thereof. In certain embodiments, the flavor-grade neoflavonoid compound is a combination of flavor-grade Compounds 4-6, or comestibly or biologically acceptable salts or derivatives thereof. In certain embodiments, the flavor-grade neoflavonoid compound is a combination of flavor-grade Compounds 1-6, or comestibly or biologically acceptable salts or derivatives thereof. In certain embodiments, the flavor-grade neoflavonoid compound is a combination of flavor-grade Compounds 1 and 4, or comestibly or biologically acceptable salts, enantiomers, or derivatives thereof.

In some embodiments, the method comprises mixing an aryl alcohol with ferulic acid, such as trans-ferulic acid, and one or more natural acids; and producing a compound according to Formula (I) by heating the combination of the aryl alcohol, the ferulic acid (e.g., trans-ferulic acid), and the one or more natural acid to a temperature of 25° C. to 220° C. for a reaction time of 30 minutes to 24 hours. In some embodiments, the aryl alcohol is from a natural source. Optionally, the trans-ferulic (e.g., trans-ferulic acid) is from a natural source.

In some embodiments, the natural acid is oxalic acid, malic acid, tartaric acid, hydrochloric acid, phosphoric acid, benzoic acid, formic acid, maleic acid, pyruvic acid, lactic acid; or a combination of any of the foregoing acids. In some embodiments, the natural acid is oxalic acid. In some embodiments, the natural acid is phosphoric acid. In some embodiments, the natural acid is malic acid. In other embodiments, natural acid is tartaric acid. Preferably, the natural acid is a combination of malic acid and tartaric acid.

In some embodiments, the heating temperature is 110° C. to 150° C., preferably 150° C. In some embodiments, the reaction time is 30 minutes to 1.5 hours, preferably one hour. In some embodiments, the heating temperature is about 110° C. to about 150° C., preferably about 150° C. In some embodiments, the reaction time is about 30 minutes to about 1.5 hours, preferably about one hour.

In some embodiments, the aryl alcohol is orcinol. Preferably, the orcinol is from a natural source. In certain embodiments, the orcinol is from a lichen selected from the group consisting of *Roccella tinctoria, Lecanora, Roccella fuciformis, Roccella pygmaea, Roccella phycopsis, Lecanora tartarea, Variolaria dealbata, Ochrolechia parella, Parmotrema tinctorum, Parmelia, Roccella montagnei*, and *Dendrographa leucophoea*. In certain embodiments, the orcinol is from curculigo orchioides, oakmoss (*Evernia prunastri*), treemoss (*Pseudevernia furfuracea*), or an aloe, preferably curculigo orchioides. In some embodiments, the trans-ferulic acid is from cereal bran. In some embodiments, the flavor-grade neoflavonoid compounds are purified from the reaction mixture. In some embodiments, the flavor-grade neoflavonoid compounds are used crude from the reaction mixture. In some embodiments, the flavor-grade neoflavonoid compounds 1 and 4, or comestibly or biologically acceptable salts, enantiomers, or derivatives thereof, are used crude from the reaction mixture.

One aspect of the present disclosure provides flavor-grade compounds for modulating sweet taste (e.g., enhancing sweet taste) of a sweet tastant. In some embodiments, the flavor-grade compounds for modulating sweet taste of a sweet tastant are prepared by the method described herein. In some embodiments, the flavor-grade compound is a neoflavonoid compound. In some embodiments, the flavor-grade neoflavonoid compound has a molecular weight less than about 1000, about 500, or about 300 Daltons. In certain embodiments, the flavor-grade neoflavonoid compound is a compound of Formula (I), or a comestibly or biologically acceptable salt or derivative thereof, or an enantiomer thereof, or a combination of any of the foregoing compounds. In certain embodiments, the flavor-grade neoflavonoid compound is flavor-grade Compound 1 or 4, or a comestibly or biologically acceptable salt, derivative, or enantiomer thereof. In certain embodiments, the flavor-grade neoflavonoid compound is Compound 2, 3, 5, or 6, or a comestibly or biologically acceptable salt or derivative thereof. In certain embodiments, the flavor-grade neoflavonoid compound is a combination of flavor-grade Compound 1 or 4, or comestibly or biologically acceptable salts, derivatives, or enantiomers thereof. The present disclosure also includes edible compositions comprising flavor-grade sweet taste modulating compounds such as the compounds of Formula (I). In addition, the present disclosure also includes edible compositions comprising flavor-grade sweet taste modulating compounds such as flavor-grade Compounds 1 or 4 or a comestibly or biologically acceptable salt, derivative, or enantiomer thereof or flavor-grade Compounds 2, 3, 5, or 6, or a comestibly or biologically acceptable salt or derivative thereof. The present disclosure also includes edible compositions comprising flavor-grade sweet taste modulating compounds such as a combination of flavor-grade Compounds 1 and 4 or comestibly or biologically acceptable salts, derivatives, or enantiomers thereof.

Such flavor-grade taste modulators may be combined with any suitable sweetener, such as a natural caloric sweetener, a natural high-potency sweetener, a synthetic sweetener including a synthetic high-potency sweetener, sugar alcohols, rare sugars, sweetener enhancers or combinations thereof, to provide a composition having enhanced sweetness. In some embodiments, the flavor-grade compound of Formula (I), or a comestibly or biologically acceptable salt or derivative thereof, or an enantiomer thereof, or a combination of any of the foregoing compounds is present in the composition in an amount at or below its sweetness threshold. In other embodiments, flavor-grade Compound 1, or a comestibly or biologically acceptable salt, derivative, or enantiomer thereof is present in the composition in an amount at or below its sweetness threshold. In other embodiments, flavor-grade Compound 2, or a comestibly or biologically acceptable salt or derivative thereof is present in the composition in an amount at or below its sweetness threshold. In other embodiments, flavor-grade Compound 3, or a comestibly or biologically acceptable salt or derivative thereof is present in the composition in an amount at or below its sweetness threshold. In other embodiments, flavor-grade Compound 4, or a comestibly or biologically acceptable salt, derivative, or enantiomer thereof is present in the composition in an amount at or below its sweetness threshold. In other embodiments, flavor-grade Compound 5, or a comestibly or biologically acceptable salt or derivative thereof is present in the composition in an amount at or below its sweetness threshold. In other embodiments, flavor-grade Compound 6, or a comestibly or biologically acceptable salt or derivative thereof is present in the composition in an amount at or below its sweetness threshold. In other embodiments, a combination of flavor-grade Compounds 1 and 4, or comestibly or biologically acceptable salts, derivatives, or enantiomers thereof is present in the composition in an amount at or below its sweetness threshold. In embodiments wherein the flavor-grade compound is present in the composition in an amount at or below its sweetness threshold, the compound does not act as a sweetener. The compositions may further comprise at least one sweet taste improving composition.

In another aspect, the present disclosure provides a method of enhancing the sweetness of a sweetener comprising combining (i) at least one sweetener, such as a natural caloric sweetener, a natural high-potency sweetener, a synthetic sweetener including a synthetic high-potency sweetener, sugar alcohols, rare sugars, sweetener enhancers or combinations thereof, and (ii) a flavor-grade neoflavonoid sweet taste modulator of the present disclosure, such as a compound of Formula (I), or a comestibly or biologically acceptable salt or derivative thereof, or an enantiomer thereof, or a combination of any of the foregoing compounds. In some embodiments, the flavor-grade neoflavonoid sweet taste modulator of the present disclosure is flavor-grade Compound 1, or a comestibly or biologically acceptable salt or derivative thereof or an enantiomer thereof. In some embodiments, the flavor-grade neoflavonoid sweet taste modulator of the present disclosure is flavor-grade Compound 2, or a comestibly or biologically acceptable salt or derivative thereof. In some embodiments, the flavor-grade neoflavonoid sweet taste modulator of the present disclosure is flavor-grade Compound 3, or a comestibly or biologically acceptable salt or derivative thereof. In some embodiments, the flavor-grade neoflavonoid sweet taste modulator of the present disclosure is flavor-grade Compound 4, or a comestibly or biologically acceptable salt or derivative thereof or an enantiomer thereof. In some embodiments, the flavor-grade neoflavonoid sweet taste modulator of the present disclosure is flavor-grade Compound 5, or a comestibly or biologically acceptable salt or derivative thereof. In some embodiments, the flavor-grade neoflavonoid sweet taste modulator of the present disclosure is flavor-grade Compound 6, or a comestibly or biologically acceptable salt or derivative thereof. In some embodiments, the flavor-grade neoflavonoid sweet taste modulator of the present disclosure is a combination of flavor-grade Compounds 1 and 4, or comestibly or biologically acceptable salts or derivatives thereof or enantiomers thereof. The method may further comprise combining (iii) at least one sweet taste improving composition. The flavor-grade compounds may be added in an amount at or below their sweetness threshold.

Other aspects of the present disclosure include edible compositions, such as beverage compositions, concentrates (for use in, e.g., beverage compositions), food products, pharmaceutical preparations and table-top sweeteners comprising the compositions of the present disclosure; methods for preparing an edible composition; methods for reducing the amount of a sweetener in an edible composition; methods for reducing caloric intake; and methods of enhancing activation of a sweet taste receptor using the flavor-grade sweet taste modulators of the present disclosure.

Particular embodiments of the disclosure are set forth in the following numbered paragraphs:

1. A method of preparing a flavor-grade compound of Formula (I):

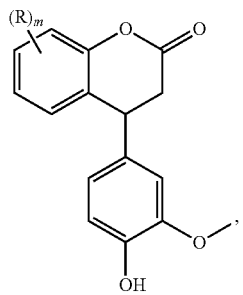

wherein R is —OH, $C_1$-$C_4$ alkyl, —$CO_2H$, acyl or formyl; m is 2 or 3; and at least one R is not OH; or a comestibly or biologically acceptable salt, solvate, or enantiomer thereof or a combination of any of the foregoing compounds, comprising:

mixing an aryl alcohol from a natural source with ferulic acid from a natural source (e.g., trans-ferulic acid having the structure:

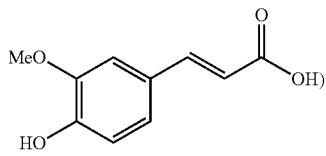

and one or more natural acids; and heating the combination of the aryl alcohol, the ferulic acid (e.g., trans-ferulic acid), and the one or more natural acid to a temperature of 25° C. to 220° C. for a reaction time of 30 minutes to 24 hours to produce the compound of Formula (I).

2. The method of Paragraph 1, wherein the natural acid is oxalic acid, malic acid, tartaric acid, hydrochloric acid, phosphoric acid, benzoic acid, formic acid, maleic acid, pyruvic acid, lactic acid; or a combination of any of the foregoing acids.

3. The method of Paragraph 2, wherein the natural acid is malic acid.

4. The method of Paragraph 2, wherein the natural acid is tartaric acid.

5. The method of Paragraph 2, wherein the natural acid is a combination of malic acid and tartaric acid.

6. The method of any one of Paragraphs 1-5, wherein the heating temperature is 110° C. to 150° C.

7. The method of any one of Paragraphs 1-5, wherein the heating temperature is 150° C.

8. The method of any one of Paragraphs 1-7, wherein the reaction time is 30 minutes to 1.5 hours.

9. The method of any one of Paragraphs 1-7, wherein the reaction time is one hour.

10. The method of any one of Paragraphs 1-9, wherein the aryl alcohol is orcinol having the structure

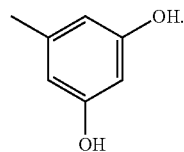

11. The method of Paragraph 10, wherein the orcinol is from a lichen selected from the group consisting of *Roccella tinctoria, Lecanora, Roccella fuciformis, Roccella pygmaea, Roccella phycopsis, Lecanora tartarea, Variolaria dealbata, Ochrolechia parella, Parmotrema tinctorum, Parmelia, Roccella montagnei*, and *Dendrographa leucophoea*.

12. The method of Paragraph 10, wherein the orcinol is from curculigo orchioides, *Evernia prunastri, Pseudevernia furfuracea*, or an aloe.

13. The method of Paragraph 12, wherein the orcinol is from curculigo orchioides.

14. The method of Paragraphs 1-13, wherein the trans-ferulic acid is from cereal bran.

15. A flavor-grade compound of Formula (I):

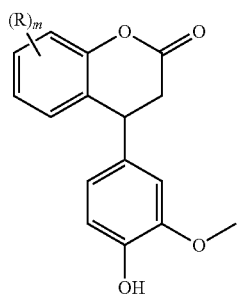

wherein R is —OH, $C_1$-$C_4$ alkyl, —$CO_2H$, acyl or formyl; m is 2 or 3; and at least one R is not OH; or a comestibly or biologically acceptable salt, solvate, or enantiomer thereof or a combination of any of the foregoing compounds.

16. The flavor-grade compound of Paragraph 15, wherein said compound is one of Compounds 1-6 having the structure:

Compound 1

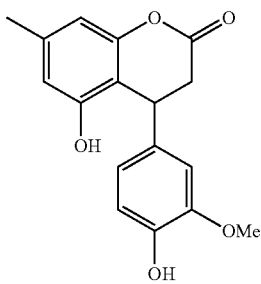 [SMILES: COc1cc(C2CC(=O)Oc3cc(C)cc(O)c32)ccc1O]

5-hydroxy-4-(4-hydroxy-3-methoxyphenyl)-7-methylchroman-2-one,

Compound 4

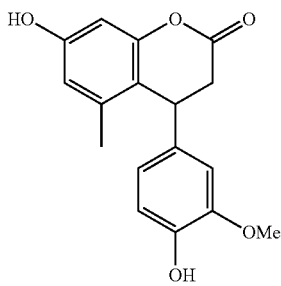

7-hydroxy-4-(4-hydroxy-3-methoxyphenyl)-5-methylchroman-2-one, or a comestibly or biologically acceptable salt, solvate, or enantiomer thereof, or Compound 2

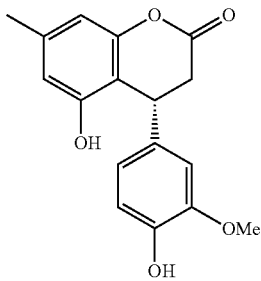 [SMILES: COc1cc([C@H]2CC(=O)Oc3cc(C)cc(O)c32)ccc1O]

(R)-5-hydroxy-4-(4-hydroxy-3-methoxyphenyl)-7-methylchroman-2-one,

Compound 3

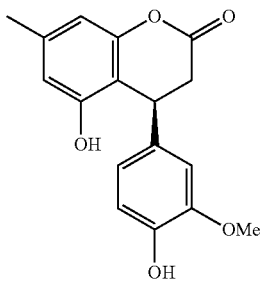 [SMILES: COc1cc([C@@H]2CC(=O)Oc3cc(C)cc(O)c32)ccc1O]

(S)-5-hydroxy-4-(4-hydroxy-3-methoxyphenyl)-7-methylchroman-2-one,

Compound 5

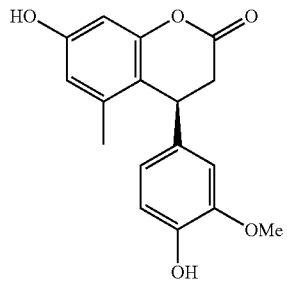

(S)-7-hydroxy-4-(4-hydroxy-3-methoxyphenyl)-5-methylchroman-2-one,

Compound 6

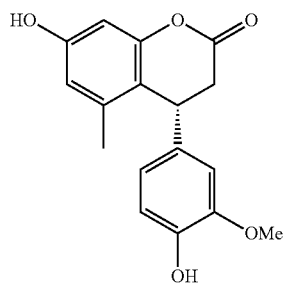

(R)-7-hydroxy-4-(4-hydroxy-3-methoxyphenyl)-5-methylchroman-2-one, or a comestibly or biologically acceptable salt or solvate thereof; or a combination of any of the foregoing compounds.

17. The flavor-grade compound of Paragraph 16, wherein said compound is flavor-grade Compound 1, 5-hydroxy-4-(4-hydroxy-3-methoxyphenyl)-7-methylchroman-2-one, or a comestibly or biologically acceptable salt, solvate, or enantiomer thereof.

18. The flavor-grade compound of Paragraph 16, wherein said compound is flavor-grade Compound 2, (R)-5-hydroxy-4-(4-hydroxy-3-methoxyphenyl)-7-methylchroman-2-one, or a comestibly or biologically acceptable salt or solvate thereof.

19. The flavor-grade compound of Paragraph 16, wherein said compound is flavor-grade Compound 3, (S)-5-hydroxy-4-(4-hydroxy-3-methoxyphenyl)-7-methylchroman-2-one, or a comestibly or biologically acceptable salt or solvate thereof.

20. The flavor-grade compound of Paragraph 16, wherein said compound is flavor-grade Compound 4, 7-hydroxy-4-(4-hydroxy-3-methoxyphenyl)-5-methylchroman-2-one, or a comestibly or biologically acceptable salt, solvate, or enantiomer thereof.

21. The flavor-grade compound of Paragraph 16, wherein said compound is flavor-grade Compound 5, (S)-7-hydroxy-4-(4-hydroxy-3-methoxyphenyl)-5-methylchroman-2-one, or a comestibly or biologically acceptable salt or solvate thereof.

22. The flavor-grade compound of Paragraph 16, wherein said compound is flavor-grade Compound 6, (R)-7-hydroxy-4-(4-hydroxy-3-methoxyphenyl)-5-methylchroman-2-one, or a comestibly or biologically acceptable salt or solvate thereof.

23. The flavor-grade compound of Paragraph 16, wherein said compound is a combination of flavor-grade Compounds 1 and 4, or comestibly or biologically acceptable salts, solvates, or enantiomers thereof.

24. A flavor-grade compound of any one of Paragraphs 15-23, or a combination of any of the foregoing compounds, prepared by the method of any one of Paragraphs 1-14.

25. A method of enhancing the sweet taste of a sweetener in an edible composition, wherein said method comprises adding an effective amount of a flavor-grade compound of Formula (I), or a comestibly or biologically acceptable salt, solvate, or enantiomer thereof, or any one of flavor-grade Compounds 1-6, or a comestibly or biologically acceptable salt or solvate thereof, or a combination of any of the foregoing compounds, to said edible composition, such that the perception of sweetness intensity of said sweetener is enhanced.

26. The method of Paragraph 25, wherein an effective amount of flavor-grade Compound 1 is added.

27. The method of Paragraph 25, wherein an effective amount of flavor-grade Compound 2 is added.

28. The method of Paragraph 25, wherein an effective amount of flavor-grade Compound 3 is added.

29. The method of Paragraph 25, wherein an effective amount of flavor-grade Compound 4 is added.

30. The method of Paragraph 25, wherein an effective amount of flavor-grade Compound 5 is added.

31. The method of Paragraph 25, wherein an effective amount of flavor-grade Compound 6 is added.

32. The method of Paragraph 25, wherein an effective amount of a combination of flavor-grade Compounds 1 and 4 is added.

33. The method of any one of Paragraphs 25-32, wherein the sweetener is a caloric sweetener, an artificial sweetener, an artificial high-potency sweetener, a natural high-potency sweetener, a sugar alcohol, a rare sugar, or a combination of any of the foregoing sweeteners.

34. The method of Paragraph 33, wherein the caloric sweetener is a carbohydrate selected from sucrose, high fructose corn or starch syrup, glucose, and fructose.

35. The method of Paragraph 34, wherein the caloric sweetener is high fructose corn or starch syrup.

36. The method of Paragraph 34, wherein the caloric sweetener is sucrose.

37. The method of Paragraph 33, wherein the sugar alcohol is a polyol selected from erythritol, sorbitol, mannitol and xylitol.

38. The method of Paragraph 33, wherein the artificial high-potency sweetener is sucralose, acesulfame potassium or other salts, aspartame, alitame, sodium or calcium salt of saccharin, neohesperidin dihydrochalcone, sodium cyclamate, neotame, or advantame, or a salt of any of the foregoing sweetners.

39. The method of Paragraph 33, wherein the natural high-potency sweetener is a steviol glycoside, rebaudioside A, rebaudioside B, rebaudioside C (dulcoside B), rebaudioside D, rebaudioside E, rebaudioside F, rebaudioside I, rebaudioside H, rebaudioside L, rebaudioside K, rebaudioside J, rebaudioside N, rebaudioside O, rebaudioside M, dulcoside A, rubusoside, stevia leaf extract, a stevioside, a glycosylated steviol glycoside, a mogroside, mogroside V, isomogroside, mogroside IV, Luo Han Guo fruit extract, siamenoside, monatin or any salt thereof (monatin SS, RR, RS, SR), curculin, glycyrrhizic acid or any salt thereof, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, or cyclocarioside I or a mixture of any of the foregoing sweeteners.

40. The method of Paragraph 33, wherein the rare sugar is a D-Psicose, D-Turanose, D-allose, D-Tagatose, D-Sorbose, L-fructose, L-glucose, D-sorbose, L-fructose, L-talose, L-ribose, L-arabinose or a mixture thereof.

41. The method of any one of Paragraphs 25-40, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 1 ppm to about 100 ppm.

42. The method of Paragraph 41, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 1 ppm to about 60 ppm.

43. The method of Paragraph 41, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 1 ppm to about 50 ppm or about 5 to about 50 ppm.

44. The method of any one of Paragraphs 25-40, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 20 to about 3,000 ppm.

45. The method of Paragraph 44, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 100 to about 1,000 ppm.

46. The method of Paragraph 45, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 100 to about 300 ppm.

47. The method of any one of Paragraphs 25-40, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 5 ppm, about 10 ppm, about 15 ppm, about 20 ppm, about 25 ppm, about 30 ppm, about 35 ppm, about 40 ppm, about 45 ppm, or about 50 ppm.

48. The method of any one of Paragraphs 25-47, wherein the edible composition is at a pH of about 2.0 to about 8.5.

49. The method of Paragraph 48, wherein the edible composition is at a pH of about 2.0 to about 4.0 or about 6.0 to about 8.0.

50. The method of Paragraph 48, wherein the edible composition is at a pH of about 3.0 or about 7.0.

51. The method of any one of Paragraphs 25-48, wherein the perception of sweetness intensity of said sweetener is enhanced by about 5% to about 50% in an edible composition at a pH of about 6.5 to about 7.5.

52. The method of any one of Paragraphs 25-48, wherein the perception of sweetness intensity of said sweetener is enhanced by about 5% to about 50% in an edible composition at a pH of about 2.5 to about 3.5.

53. The method of any one of Paragraphs 25-50, wherein the perception of sweetness intensity of said sweetener in the edible composition is enhanced by about 5% to about 100%.

54. The method of Paragraph 53, wherein the perception of sweetness intensity of said sweetener in the edible composition is enhanced by about 5% to about 75%.

55. The method of Paragraph 54, wherein the perception of sweetness intensity of said sweetener in the edible composition is enhanced by about 10% to about 60%.

56. The method of Paragraph 55, wherein the perception of sweetness intensity of said sweetener in the edible composition is enhanced by about 10% to about 50%.

57. The method of Paragraph 56, wherein the perception of sweetness intensity of said sweetener in the edible composition is enhanced by about 10% to about 25%.

58. The method of any one of Paragraphs 25-57, wherein the edible composition is a beverage.

59. The method of Paragraph 58, wherein the beverage is a non-alcoholic beverage.

60. The method of any one of Paragraphs 25-59, wherein the edible composition further comprises one or more of an antioxidant, a vitamin, glucosamine, a dietary fiber, a hydration agent, a probiotic, a prebiotic, a phytosterol, an omega-3 oil, a fatty acid, a saponin, a natural or synthetic preservative, a mineral, a weight management agent, an osteoporosis management agent, a phytoestrogen, a long chain primary aliphatic saturated alcohol, or a phytosterol or a combination of any of the foregoing.

61. The method of any one of Paragraphs 25-60, wherein said edible composition further comprises one or more of a sweet taste improving additive.

62. The method of Paragraph 61, wherein said sweet taste improving additive is selected from the group consisting of a carbohydrate, a polyol, a glycoside, an amino acid, a sugar acid, a polyamino acid, a nucleotide, a salt, an organic acid, an organic ester, a flavoring agent, a sweet flavor, an alcohol, a flavonoid, a bitter compound, a protein, a protein hydrolysate, an emulsifier, a surfactant and a polymer.

63. The method of Paragraph 62, wherein the sweet taste improving additive is a sweet flavor.

64. The method of Paragraph 62, wherein the sweet taste improving additive is a polyol.

65. The method of Paragraph 64, wherein the polyol is erythritol.

66. The method of Paragraph 65, wherein the ratio of erythritol to the flavor-grade compound of Formula (I), or the comestibly or biologically acceptable salt, solvate, or enantiomer thereof, or any one of flavor-grade Compounds 1-6, or the comestibly or biologically acceptable salt or solvate thereof; or the combination of any of the foregoing compounds, is about 1:1 to about 800:1 by weight.

67. The method of Paragraph 66, wherein the ratio of erythritol to the flavor-grade compound of Formula (I), or the comestibly or biologically acceptable salt, solvate, or enantiomer thereof, or any one of flavor-grade Compounds 1-6, or the comestibly or biologically acceptable salt or solvate thereof; or the combination of any of the foregoing compounds, is about (30-200):1 or about (50-100):1 by weight.

68. The method of Paragraph 62, wherein the sweet taste improving additive is an amino acid.

69. The method of Paragraph 68, wherein the amino acid is glycine, alanine, lysine, glutamic acid, taurine, serine or proline.

70. The method of Paragraph 68 or 69, wherein the amino acid is present in a concentration of about 10 ppm to about 25,000 ppm.

71. The method of Paragraph 70, wherein the amino acid is present in a concentration of about 100 ppm to about 5,000 ppm.

72. The method of Paragraph 62, wherein said sweet taste improving additive is a salt.

73. The method of Paragraph 72, wherein said salt is NaCl, KCl or $MgCl_2$.

74. The method of any one of Paragraphs 25-73, wherein the perception of sweetness intensity of said sweetener is enhanced, as measured in an in-vitro assay for a sweet, responsive assay.

75. The method of any one of Paragraphs 25-73, wherein the perception of sweetness intensity of said sweetener is enhanced, as measured in an in-vivo assay for a sweet, responsive assay.

76. A method of reducing the bitter taste of a bitter tastant in an edible composition, wherein said method comprises adding an effective amount of a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, to said edible composition, such that the perception of bitter taste of said bitter tastant is reduced.

77. The method of any one of Paragraphs 25-76, wherein the flavor-grade compound of Formula (I), or the comestibly or biologically acceptable salt, solvate, or enantiomer thereof, or any one of flavor-grade Compounds 1-6, or the comestibly or biologically acceptable salt or solvate thereof; or the combination of any of the foregoing compounds, are used to decrease off-taste in an edible composition.

78. The method of Paragraph 77, wherein the off-taste is bitter, metallic or astringent.

79. A composition comprising a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, wherein said composition is edible and capable of enhancing the sweet taste of a sweetener.

80. The composition of Paragraph 79, wherein the composition further comprises a sweetener.
81. The composition of any one of Paragraphs 79-80, wherein the sweetener is a caloric sweetener, an artificial sweetener, a natural high-potency sweetener, or a combination of any of the foregoing sweeteners.
82. The composition of Paragraph 81, wherein the caloric sweetener is a carbohydrate selected from sucrose, high fructose corn or starch syrup, glucose, and fructose.
83. The composition of Paragraph 82, wherein the caloric sweetener is high fructose corn or starch syrup.
84. The composition of Paragraph 82, wherein the caloric sweetener is sucrose.
85. The composition of Paragraph 81, wherein the caloric sweetener is a polyol selected from erythritol, sorbitol, mannitol and xylitol.
86. The composition of Paragraph 81, wherein the artificial sweetener is sucralose, acesulfame potassium or another salt thereof, aspartame, alitame, a sodium or calcium salt of saccharin, neohesperidin dihydrochalcone, sodium cyclamate, neotame, or advantame, or a salt thereof.
87. The composition of Paragraph 81, wherein the natural high-potency sweetener is steviol glycoside, rebaudioside A, rebaudioside B, rebaudioside C (dulcoside B), rebaudioside D, rebaudioside E, rebaudioside F, rebaudioside I, rebaudioside H, rebaudioside L, rebaudioside K, rebaudioside J, rebaudioside N, rebaudioside O, Rebaudioside M, dulcoside A, rubusoside, stevia leaf extract, a stevioside, a glycosylated steviol glycoside, mogroside V, isomogroside, mogroside IV, Luo Han Guo fruit extract, siamenoside, monatin or any salt thereof (monatin SS, RR, RS, SR), curculin, glycyrrhizic acid or any salt thereof, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, or cyclocarioside I or a mixture of any of the foregoing sweeteners.
88. The composition of any one of Paragraphs 79-87, wherein said composition comprises flavor-grade Compound 1 or a comestibly acceptable salt or enantiomer thereof.
89. The composition of any one of Paragraphs 79-87, wherein said composition comprises flavor-grade Compound 2 or a comestibly acceptable salt thereof.
90. The composition of any one of Paragraphs 79-87, wherein said composition comprises flavor-grade Compound 3 or a comestibly acceptable salt thereof.
91. The composition of any one of Paragraphs 79-87, wherein said composition comprises flavor-grade Compound 4 or a comestibly acceptable salt or enantiomer thereof.
92. The composition of any one of Paragraphs 79-87, wherein said composition comprises flavor-grade Compound 5 or a comestibly acceptable salt thereof.
93. The composition of any one of Paragraphs 79-87, wherein said composition comprises flavor-grade Compound 6 or a comestibly acceptable salt thereof.
94. The composition of any one of Paragraphs 79-87, wherein said composition comprises a combination of flavor-grade Compounds 1 and 4, or comestibly acceptable salts or enantiomers thereof.
95. The composition of any one of Paragraphs 79-87, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 0.1 ppm to about 100 ppm.
96. The composition of Paragraph 95, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 5 ppm to about 60 ppm.
97. The composition of Paragraph 96, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 10 ppm to about 50 ppm.
98. The composition of any one of Paragraphs 79-87, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 30 ppm to about 3,000 ppm.
99. The composition of Paragraph 98, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 100 ppm to about 1,000 ppm.
100. The composition of Paragraph 99, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 100 ppm to about 300 ppm.
101. The composition of Paragraph 95, wherein said flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present in the edible composition at a concentration of about 1 ppm, about 5 ppm, about 10 ppm, about 15 ppm, about 20 ppm, about 25 ppm, about 30 ppm, about 35 ppm, about 40 ppm, about 45 ppm, or about 50 ppm.
102. The composition of any one of Paragraphs 79-101, wherein the edible composition is at a pH of about 2.0 to about 8.5.
103. The composition of Paragraph 102, wherein the edible composition is at a pH of about 2.0 to about 4.0, about 3.0 to about 7.0, or about 6.0 to about 8.0.
104. The composition of Paragraph 103, wherein the edible composition is at a pH of about 3.0 or about 7.0.

105. The composition of any one of Paragraphs 79-104, wherein the perception of sweetness intensity of said sweetener in the edible composition is enhanced by about 5% to about 100%.
106. The composition of Paragraph 105, wherein the perception of sweetness intensity of said sweetener in the edible composition is enhanced by about 5% to about 70%.
107. The composition of Paragraph 106, wherein the perception of sweetness intensity of said sweetener in the edible composition is enhanced by about 5% to about 50%.
108. The composition of Paragraph 106, wherein the perception of sweetness intensity of said sweetener in the edible composition is enhanced by about 10% to about 60%.
109. The composition of Paragraph 108, wherein the perception of sweetness intensity of said sweetener in the edible composition is enhanced by about 10% to about 50%.
110. The composition of Paragraph 109, wherein the perception of sweetness intensity of said sweetener in the edible composition is enhanced by about 10% to about 40%.
111. The composition of any one of Paragraphs 79-110, wherein the edible composition is a beverage.
112. The composition of Paragraph 111, wherein the beverage is a non-alcoholic beverage.
113. The composition of any one of Paragraphs 79-112, wherein the edible composition further comprises one or more of an antioxidant, a vitamin, glucosamine, a fiber, a hydration agent, a probiotic, a prebiotic, a phytosterol, an omega-3 oil, a fatty acid, a saponin, a natural or synthetic preservative, a mineral, a weight management agent, an osteoporosis management agent, a phytoestrogen, a long chain primary aliphatic saturated alcohol, a phytosterol or a combination of any of the foregoing.
114. The composition of any one of Paragraphs 79-113, wherein said edible composition further comprises one or more of a sweet taste improving additive.
115. The composition of Paragraph 114, wherein said sweet taste improving additive is selected from the group consisting of a carbohydrate, a polyol, a glycoside, an amino acid, a sugar acid, a polyamino acid, a nucleotide, a salt, an organic acid, an organic ester, a flavoring agent, a sweet flavor, an alcohol, a flavonoid, a bitter compound, a protein, a protein hydrolysate, an emulsifier, a surfactant and a polymer.
116. The composition of Paragraph 115, wherein the sweet taste improving additive is a polyol.
117. The composition of Paragraph 116, wherein the polyol is erythritol.
118. The composition of Paragraph 117, wherein the ratio of erythritol to the flavor-grade compound of Formula (I), or the comestibly or biologically acceptable salt, solvate, or enantiomer thereof, or any one of flavor-grade Compounds 1-6, or the comestibly or biologically acceptable salt or solvate thereof; or the combination of any of the foregoing compounds, is about 1:1 to about 800:1 by weight.
119. The composition of Paragraph 118, wherein the ratio of erythritol to the flavor-grade compound of Formula (I), or the comestibly or biologically acceptable salt, solvate, or enantiomer thereof, or any one of flavor-grade Compounds 1-6, or the comestibly or biologically acceptable salt or solvate thereof; or the combination of any of the foregoing compounds, is about (30-200):1 or about (50-100):1 by weight.
120. The composition of Paragraph 115, wherein the sweet taste improving additive is an amino acid.
121. The composition of Paragraph 120, wherein the amino acid is glycine, alanine, taurine, serine or proline.
122. The composition of Paragraph 120 or 121, wherein the amino acid is present in a concentration of about 10 ppm to about 25,000 ppm.
123. The composition of Paragraph 122, wherein the amino acid is present in a concentration of about 100 ppm to about 1000 ppm.
124. The composition of Paragraph 115, wherein said sweet taste improving additive is a salt.
125. The composition of Paragraph 124, wherein said salt is NaCl, KCl or $MgCl_2$.
126. A method of preparing an edible composition comprising:
    (a) providing a comestibly acceptable carrier; and
    (b) adding to said comestibly acceptable carrier a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds.
127. The method of Paragraph 126, wherein the comestibly acceptable carrier comprises a sweetener.
128. The method of any one of Paragraphs 126-127, wherein the sweetener is a caloric sweetener, an artificial sweetener, a natural high-potency sweetener, or a combination of any of the foregoing sweeteners.
129. The method of Paragraph 128, wherein the caloric sweetener is a carbohydrate selected from sucrose, high fructose corn or starch syrup, glucose, and fructose.
130. The method of Paragraph 129, wherein the caloric sweetener is high fructose corn or starch syrup.
131. The method of Paragraph 128, wherein the caloric sweetener is a polyol selected from erythritol, sorbitol, mannitol and xylitol.
132. The method of Paragraph 128, wherein the artificial sweetener is sucralose, acesulfame potassium or another salt thereof, aspartame, alitame, a sodium or calcium salt of saccharin, neohesperidin dihydrochalcone, sodium cyclamate, neotame, or advantame, or a salt thereof.
133. The method of Paragraph 128, wherein the natural high-potency sweetener is steviol glycoside, rebaudioside A, rebaudioside B, rebaudioside C (dulcoside B), rebaudioside D, rebaudioside E, rebaudioside F, rebaudioside I, rebaudioside H, rebaudioside L, rebaudioside K, rebaudioside J, rebaudioside N, rebaudioside O, rebaudioside M, dulcoside A, rubusoside, stevia leaf extract, a stevioside, a glycosylated steviol glycoside, mogroside V, isomogroside, mogroside IV, Luo Han Guo fruit extract, siamenoside, monatin or one of its salts (monatin SS, RR, RS, SR), curculin, glycyrrhizic acid or one of its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, or cyclocarioside I or a mixture thereof.
134. The composition of Paragraph 111, wherein said composition is a beverage selected from the group consisting of a non-carbonated beverage, a carbonated beverage, a cola, a root beer, a fruit flavored beverage, a citrus-flavored beverage, a fruit juice, a fruit-containing beverage, a vegetable juice, a vegetable containing beverage, tea, coffee, a dairy beverage, a sports drink, an energy drink, and enhanced or flavored water.

135. The composition of Paragraph 79, wherein the composition is used in food, a beverage product, a pharmaceutical composition, a nutritional product, a functional product, a dietary supplement, an over-the-counter medication, or an oral care product.

136. A tabletop sweetener composition comprising a sweetener and a flavor-grade sweet taste modulator according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds.

137. The tabletop sweetener composition of Paragraph 136, further comprising at least one bulking agent, additive, anti-caking agent, functional ingredient or a combination of any of the foregoing.

138. The tabletop sweetener composition of Paragraph 136, wherein the tabletop sweetener composition is in the form of a liquid.

139. The composition of Paragraph 135, wherein the food or beverage product is selected from the group consisting of soup, a powdered soft drink, a bakery product, a chewing gum, a confection, a cereal, an edible gel, a jam or jelly, a spread, ketchup, a dairy product, a frozen dairy product, a gelatin/pudding, and an ice-cream.

140. A delivery system selected from the group consisting of a co-crystallized flavor composition with a sugar or a polyol, an agglomerated flavor composition, a compacted flavor composition, a dried flavor composition, a particle flavor composition, a spheronized flavor composition, a granular flavor composition or a liquid flavor composition, wherein the flavor composition comprises a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds.

141. A method of reducing the bitter taste of a bitter tastant in an edible composition, wherein said method comprises adding an effective amount of a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, to said edible composition, such that the perception of bitter taste of said bitter tastant is reduced.

142. A composition comprising a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, wherein said composition is edible and capable of reducing the bitter taste of a bitter tastant.

143. A composition comprising flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, wherein said composition is edible and capable of enhancing the sweet taste of a sweetener and reducing the bitter taste of a bitter tastant.

144. The composition of Paragraph 143, wherein the composition is a beverage.

145. A flavor-grade sweet enhancer prepared by the method of any one of Paragraphs 1-14.

DETAILED DESCRIPTION OF THE INVENTION

In order that the disclosure herein may be fully understood, the following detailed description is set forth.

Unless defined otherwise, all technical and scientific terms used herein have the same meaning as those commonly understood by one of ordinary skill in the art to which this disclosure belongs. Although methods and materials similar or equivalent to those described herein can be used in the practice or testing of the present disclosure, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "aliphatic" refers to straight chain or branched hydrocarbons that are completely saturated or that contain one or more units of unsaturation. For example, aliphatic groups include substituted or unsubstituted linear or branched alkyl, alkenyl, and alkynyl groups. Unless indicated otherwise, the term "aliphatic" encompasses both substituted and unsubstituted hydrocarbons.

The term "alkoxy" refers to O-alkyl substituent, wherein the alkyl portion may be optionally substituted. Examples of alkoxy substituents include, but are not limited to, methoxy, ethoxy, n-propoxy, isopropoxy and n-butoxy. Also, explicitly included within the scope of the term "alkoxy" are O-alkenyl or O-alkynyl groups. In all cases, the alkyl, alkene, and alkyne portions may be optionally substituted.

The term "alkyl" refers to both straight and branched saturated chains containing, for example, 1-3, 1-6, 1-9, or 1-12 carbon atoms. An alkyl group may be optionally substituted.

The term "alkenyl" refers to both straight and branched saturated chains containing, for example, 2-3, 2-6, 2-9, or 2-12 carbon atoms, and at least one carbon-carbon double bond. An alkenyl group may be optionally substituted.

The term "alkynyl" refers to both straight and branched saturated chains containing, for example, 2-3, 2-6, 2-9, or 2-12 carbon atoms, and at least one carbon-carbon triple bond. An alkynyl group may be optionally substituted.

The term "bitter" or "bitter taste" as used herein refers to the perception or gustatory sensation resulting following the detection of a bitter tastant. The following flavor attributes may contribute to bitter taste: astringent, bitter-astringent, metallic, bitter-metallic, as well as off-tastes aftertastes and undesirable tastes including but not limited to freezer-burn and card-board taste or a combination of these. It is noted that, in the art, the term "off-taste" is often synonymous with "bitter taste."

The term "bitter tastant" refers to a compound that activates or that can be detected by a bitter taste receptor and/or confers the perception of a bitter taste in a subject. A "bitter tastant" also refers to a multiplicity of compounds that combine to activate or be detected by a bitter taste receptor and/or confer the perception of a bitter taste in a subject. Those of skill in the art can readily identify and understand what is meant by a bitter tastant. Bitter tastants may include substances which also possess or primarily possess a sweet taste. Examples of such substances include steviol glycosides and acesulfame potassium.

The term "combination" as it relates to compounds of the disclosure refers to two or more flavor-grade compounds of Formula (I) (including Compounds 1-6), or comestibly or biologically acceptable salts, solvates, or enantiomers thereof.

The term "comestibly or biologically acceptable salt" refers to any comestibly or biologically acceptable salt, ester, or salt of such ester, of a compound of the present disclosure, which, upon ingestion, is capable of providing (directly or indirectly) a compound of the present disclosure, or a metabolite, residue or portion thereof, characterized by the ability to enhance the perception of a sweet taste attributed to a sweetener and/or reduce the perception of bitter taste due to a bitter tastant. Similarly, the term "comestibly or biologically acceptable derivative" refers to any comestibly or biologically acceptable derivative of a compound of the present disclosure, which, upon ingestion, is capable of providing (directly or indirectly) a compound of the present disclosure, or a metabolite, residue or portion thereof, characterized by the ability to enhance the perception of a sweet taste attributable to a sweetener and reduce the perception of a bitter taste attributed to a bitter tastant. A "comestible product" is a product suitable for oral use, such as eating or drinking. Therefore, a comestibly acceptable compound is an edible compound. If a comestibly or biologically acceptable salt of a compound of the present disclosure is used, such salt is preferably derived from inorganic or organic acids and bases. Examples of such salts include, but are not limited to, those derived from appropriate bases, including alkali metal (e.g., sodium and potassium), alkaline earth metal (e.g., magnesium), ammonium and $N^+(C_{1-4}$ alkyl$)_4$ salts.

The term "solvate" refers to a physical association of a compound of this disclosure with one or more solvent molecules that does not interfere with the biological activity of the compound. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, hydrates, and the like. A "hydrate" is a solvate wherein the solvent molecule is water and includes a hemihydrate, a monohydrate, a sesquihydrate, a dihydrate, etc.

The term "diet" collectively refers to the food products and/or beverages consumed by a subject. A subject's "diet" also includes any consumer products or pharmaceutical compositions the subject ingests.

The term "flavor modifier" refers to a compound or a mixture of compounds that, when added to an edible composition, such as a food product, changes the individual characteristics of a food flavor (odor and/or taste). Flavor modification effects can include increasing, decreasing, masking, eliminating, reducing, enhancing or changing the perception of relevant sensorial characteristics of flavor in the edible composition. The ability of flavor modifiers to modify flavor may be independent of their aromatic or taste characteristics.

The term "flavor-grade" refers to a compound for which nothing artificial or synthetic has been included in, has been added to, or has been used to synthesize, make, or prepare said compound. A flavor-grade compound is synthesized, made, or prepared using material of plant, animal or microbiological origin, and preferably material of plant origin. The significant function of a flavor-grade compound in food is flavoring rather than nutritional. Processes to generate flavor-grade compounds include traditional food preparation processes, such as heating, fermentation, distillation, and microbiological processes, among others.

The term "natural acid" refers to an acid from a natural source, typically a botanical source. Preferably, the natural acid is flavor-grade. Non-limiting examples of natural acids include acid oxalic acid, malic acid, tartaric acid, hydrochloric acid, phosphoric acid, benzoic acid, formic acid, maleic acid, pyruvic acid, and lactic acid. In some embodiments, a combination of natural acids are used. In some embodiments, the natural acid is not a sulfuric acid. Optionally, the natural acid is not a sulfonic acid, such as p-toluenesulfonic acid.

The term "natural source" refers to a living organism from which a natural product can be extracted or derived. Preferably, the natural source is a botanical source.

The term "pharmaceutically active ingredient" refers to a compound in a pharmaceutical composition which is biologically active.

The term "replace" or "replacing" refers to substituting one compound for another compound in or in the preparation of, for example, an edible composition, such as food product. It includes complete and partial replacements or substitutions.

An aliphatic group may contain one or more substituents. Examples of suitable substituents on a saturated or unsaturated carbon of an aliphatic group include, but are not limited to, halogen, $-CF_3$, $-R'$, $-OR'$, $-OH$, $-SH$, $-SR'$, protected $-OH$ (such as acyloxy), $-NO_2$, $-CN$, $-NH_2$, $-NHR'$, $-N(R')_2$, $-NHCOR'$, $-NHCONH_2$, $-NHCONHR'$, $-NHCON(R')_2$, $-NRCOR'$, $-NHCO_2H$, $-NHCO_2R'$, $-CO_2R'$, $-CO_2H$, $-COR'$, $-CONH_2$, $-CONHR'$, $-CON(R')_2$, $-S(O)_2H$, $-S(O)_2R'$, $-S(O)_3H$, $-S(O)_3R'$, $-S(O)_2NH_2'-S(O)H$, $-S(O)R'$, $-S(O)_2NHR'$, $-S(O)_2N(R')_2$, $-NH\ S(O)_2H$, or $-NHS(O)_2R'$, $=O$, $=S$, $=NNHR'$, $=NN(R')_2$, $=N-OR'$, $=NNHCOR'$, $=NNHCO_2R'$, $=NNHSO_2R'$, $=N-CN$, or $=NR'$, wherein $R'$ is selected from H, aliphatic, carbocyclyl, heterocyclyl, aryl, aralkyl, heteroaryl, or heteroaralkyl and each $R'$ is optionally substituted with one or more halogen, nitro, cyano, amino, $-NH$-(unsubstituted aliphatic), $-N$-(unsubstituted aliphatic)$_2$, carboxy, carbamoyl, hydroxy, $-O$-(unsubstituted aliphatic), $-SH$, $-S$-(unsubstituted aliphatic), $CF_3$, $-S(O)_2NH_2'$ unsubstituted aliphatic, unsubstituted carbocyclyl, unsubstituted heterocyclyl, unsubstituted aryl, unsubstituted aralkyl, unsubstituted heteroaryl, or unsubstituted heteroaralkyl. Guided by this specification, the selection of suitable substituents is within the knowledge of one skilled in the art.

As defined herein, the compounds of the disclosure are intended to include all stereochemical forms of the compound, including geometric isomers (i.e., E, Z) and optical isomers (i.e., R, S). Single stereochemical isomers as well as enantiomeric mixtures of the present compounds are within the scope of the disclosure and are specifically contemplated. Unless otherwise stated, formulas depicted herein are also meant to include compounds which differ only in the presence of one or more isotopically enriched atoms. For example, compounds having the present formulas except for the replacement of a hydrogen by a deuterium or tritium, or the replacement of a carbon by a $^{13}$C- or $^{14}$C-enriched carbon are within the scope of this disclosure.

One aspect of present disclosure provides edible compositions comprising a flavor-grade sweet taste modulator of the present disclosure, including food products, consumer products, and pharmaceutical compositions comprising said compounds, and methods of preparing a such compositions. The present disclosure also provides methods of reducing the amount of a sweetener in an edible composition, methods for reducing caloric intake, methods of enhancing or potentiating sweet taste of a sweetener, methods of blocking a bitter taste, methods of enhancing or potentiating the activity of a sweet taste receptor, and methods of synthesizing flavor-grade sweet taste modulators. The present disclosure also includes reducing the amount of a sweetener in an edible composition or diet by replacing an amount of sugar or the other sweetener with an amount of one or more compounds or one or more extracts containing compounds of the present disclosure.

Process for Preparing Flavor-Grade Sweet Taste Modulators

In some embodiments, the disclosure relates to a process for preparing a flavor-grade compound of Formula (I):

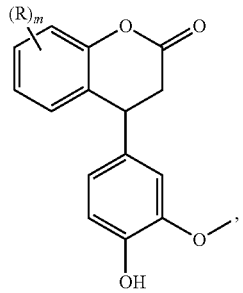

wherein R is —OH, $C_1$-$C_4$ alkyl, —$CO_2$H, acyl or formyl; m is 2 or 3; and at least one R is not OH; or a comestibly or biologically acceptable salt, solvate, or enantiomer thereof or a combination of any of the foregoing compounds, comprising (1) mixing an aryl alcohol from a natural source with ferulic acid from a natural source (e.g., trans-ferulic acid having the structure:

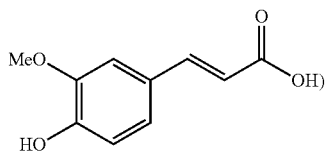

and one or more natural acids; and (2) heating the combination of the aryl alcohol, ferulic acid (e.g., trans-ferulic acid), and acid to a temperature of 25° C. to 220° C. for a reaction time of 30 minutes to 24 hours to produce the compound of Formula (I).

In some embodiments, the one or more natural acid is from a botanical source.

In some embodiments, the natural acid is oxalic acid, malic acid, tartaric acid, hydrochloric acid, phosphoric acid, benzoic acid, formic acid, maleic acid, pyruvic acid, lactic acid; or a combination of any of the foregoing acids. In some embodiments, the natural acid is oxalic acid. In some embodiments, the natural acid is phosphoric acid. In other embodiments, the natural acid is malic acid. In some embodiments, the natural acid is tartaric acid. In some embodiments, the natural acid is a combination of malic acid and tartaric acid. In some embodiments, the natural acid is used as a solvent for the reactants of the process for preparing a flavor-grade compound of Formula (I). In some embodiments, a solvent is used for the reactants of the process for preparing a flavor-grade compound of Formula (I), provided the solvent is not 1,4-dioxane. In some embodiments, a combination of ethanol and water is used as a solvent for the reactants of the process for preparing a flavor-grade compound of Formula (I). In some embodiments, the acid use in the process for preparing a flavor-grade compound is not sulfuric acid. In some embodiments, the acid use in the process for preparing a flavor-grade compound is not sulfonic acid. In some embodiments, the acid use in the process for preparing a flavor-grade compound is not p-toluenesulfonic acid.

In some embodiments, the natural acid has a pKa between −7 to 8. In some embodiments, the natural acid has a pKa between 1 to 8. In some embodiments, the natural acid has a pKa between 1 to 6. In some embodiments, the natural acid has a pKa between 2 to 6. In some embodiments, the natural acid has a pKa between 1 to 5. In some embodiments, the natural acid has a pKa between 2 to 5. In some embodiments, the natural acid has a pKa of 1. In some embodiments, the natural acid has a pKa of 1.5. In some embodiments, the natural acid has a pKa of 2. In some embodiments, the natural acid has a pKa of 2.5. In some embodiments, the natural acid has a pKa of 3. In some embodiments, the natural acid has a pKa of 3.5. In some embodiments, the natural acid has a pKa of 4. In some embodiments, the natural acid has a pKa of 4.5. In some embodiments, the natural acid has a pKa of 5. In some embodiments, the natural acid has a pKa of 5.5. In some embodiments, the natural acid has a pKa of 6. In some embodiments, the natural acid has a pKa of 6.5. In some embodiments, the natural acid has a pKa of about 1. In some embodiments, the natural acid has a pKa of about 1.5. In some embodiments, the natural acid has a pKa of about 2. In some embodiments, the natural acid has a pKa of about 2.5. In some embodiments, the natural acid has a pKa of about 3. In some embodiments, the natural acid has a pKa of about 3.5. In some embodiments, the natural acid has a pKa of about 4. In some embodiments, the natural acid has a pKa of about 4.5. In some embodiments, the natural acid has a pKa of about 5. In some embodiments, the natural acid has a pKa of about 5.5. In some embodiments, the natural acid has a pKa of about 6. In some embodiments, the natural acid has a pKa of about 6.5.

In some embodiments, the heating temperature for the process for preparing a flavor-grade compound of Formula (I), or a combination thereof, is 110° C. to 150° C. In some embodiments, the heating temperature for the process for preparing a flavor-grade compound of Formula (I), or a combination thereof, is 25° C. to 50° C. In some embodiments, the heating temperature for the process for preparing a flavor-grade compound of Formula (I), or a combination thereof, is 50° C. to 75° C. In some embodiments, the heating temperature for the process for preparing a flavor-grade compound of Formula (I), or a combination thereof, is 75° C. to 100° C. In some embodiments, the heating temperature for the process for preparing a flavor-grade compound of Formula (I), or a combination thereof, is 100° C. to 125° C. In some embodiments, the heating temperature for the process for preparing a flavor-grade compound of Formula (I), or a combination thereof, is 125° C. to 150° C. In some embodiments, the heating temperature for the process for preparing a flavor-grade compound of Formula (I), or a combination thereof, is 150° C. to 175° C. In some embodiments, the heating temperature for the process for preparing a flavor-grade compound of Formula (I), or a combination thereof, is 175° C. to 200° C. In some embodiments, the heating temperature for the process for preparing a flavor-grade compound of Formula (I), or a combination thereof, is 200° C. to 220° C. In some embodiments, the heating temperature is 100° C. In some embodiments, the heating temperature is 110° C. In some embodiments, the heating temperature is 120° C. In some embodiments, the heating temperature is 130° C. In some embodiments, the heating temperature is 140° C. In some embodiments, the heating temperature is 150° C. In some embodiments, the heating temperature is 160° C. In some embodiments, the heating temperature is 170° C. In some embodiments, the heating temperature is 180° C. In some embodiments, the heating temperature is 190° C. In some embodiments, the heating temperature is 200° C.

In some embodiments, the heating temperature for the process for preparing a flavor-grade compound of Formula (I), or a combination thereof, is at the melting temperature of the natural acid used in the process. In some embodiments, the heating temperature for the process for preparing a flavor-grade compound of Formula (I), or a combination thereof, is at the melting temperature of oxalic acid. In some embodiments, the heating temperature for the process for preparing a flavor-grade compound of Formula (I), or a combination thereof, is at 102° C. to 103° C. In some embodiments, the heating temperature for the process for preparing a flavor-grade compound of Formula (I), or a combination thereof, is at the melting temperature of malic acid. In some embodiments, the heating temperature for the process for preparing a flavor-grade compound of Formula (I), or a combination thereof, is at 130° C. In some embodiments, the heating temperature for the process for preparing a flavor-grade compound of Formula (I), or a combination thereof, is at the melting temperature of citric acid. In some embodiments, the heating temperature for the process for preparing a flavor-grade compound of Formula (I), or a combination thereof, is at 153° C. In some embodiments, the heating temperature for the process for preparing a flavor-grade compound of Formula (I), or a combination thereof, is at the melting temperature of tartaric acid. In some embodiments, the heating temperature for the process for preparing a flavor-grade compound of Formula (I), or a combination thereof, is at 171° C. to 174° C. In some embodiments, the heating temperature for the process for preparing a flavor-grade compound of Formula (I), or a combination thereof, is at the melting temperature of phosphoric acid. In some embodiments, the heating temperature for the process for preparing a flavor-grade compound of Formula (I), or a combination thereof, is at 42° C. In some embodiments, the heating temperature for the process for preparing a flavor-grade compound of Formula (I), or a combination thereof, is at the melting temperature of benzoic acid. In some embodiments, the heating temperature for the process for preparing a flavor-grade compound of Formula (I), or a combination thereof, is at 122° C. In some embodiments, the heating temperature for the process for preparing a flavor-grade compound of Formula (I), or a combination thereof, is at the melting temperature of maleic acid. In some embodiments, the heating temperature for the process for preparing a flavor-grade compound of Formula (I), or a combination thereof, is at 135° C.

In some embodiments, the heating temperature for the process for preparing a flavor-grade compound of Formula (I), or a combination thereof, is about 110° C. to about 150° C. In some embodiments, the heating temperature for the process for preparing a flavor-grade compound of Formula (I), or a combination thereof, is about 25° C. to about 50° C. In some embodiments, the heating temperature for the process for preparing a flavor-grade compound of Formula (I), or a combination thereof, is about 50° C. to about 75° C. In some embodiments, the heating temperature for the process for preparing a flavor-grade compound of Formula (I), or a combination thereof, is about 75° C. to about 100° C. In some embodiments, the heating temperature for the process for preparing a flavor-grade compound of Formula (I), or a combination thereof, is about 100° C. to about 125° C. In some embodiments, the heating temperature for the process for preparing a flavor-grade compound of Formula (I), or a combination thereof, is about 125° C. to about 150° C. In some embodiments, the heating temperature for the process for preparing a flavor-grade compound of Formula (I), or a combination thereof, is about 150° C. to about 175° C. In some embodiments, the heating temperature for the process for preparing a flavor-grade compound of Formula (I), or a combination thereof, is about 175° C. to about 200° C. In some embodiments, the heating temperature for the process for preparing a flavor-grade compound of Formula (I), or a combination thereof, is about 200° C. to about 220° C. In some embodiments, the heating temperature is about 100° C. In some embodiments, the heating temperature is about 110° C. In some embodiments, the heating temperature is about 120° C. In some embodiments, the heating temperature is about 130° C. In some embodiments, the heating temperature is about 140° C. In some embodiments, the heating temperature is about 150° C. In some embodiments, the heating temperature is about 160° C. In some embodiments, the heating temperature is about 170° C. In some embodiments, the heating temperature is about 180° C. In some embodiments, the heating temperature is about 190° C. In some embodiments, the heating temperature is about 200° C.

In some embodiments, the heating temperature for the process for preparing a flavor-grade compound of Formula (I), or a combination thereof, is about the melting temperature of the natural acid used in the process. In some embodiments, the heating temperature for the process for preparing a flavor-grade compound of Formula (I), or a combination thereof, is about the melting temperature of oxalic acid. In some embodiments, the heating temperature for the process for preparing a flavor-grade compound of Formula (I), or a combination thereof, is about 102° C. to about 103° C. In some embodiments, the heating temperature for the process for preparing a flavor-grade compound of Formula (I), or a combination thereof, is about the melting temperature of malic acid. In some embodiments, the heating temperature for the process for preparing a flavor-grade compound of Formula (I), or a combination thereof, is about 130° C. In some embodiments, the heating temperature for the process for preparing a flavor-grade compound of Formula (I), or a combination thereof, is about the melting temperature of citric acid. In some embodiments, the heating temperature for the process for preparing a flavor-grade compound of Formula (I), or a combination thereof, is about 153° C. In some embodiments, the heating temperature for the process for preparing a flavor-grade compound of Formula (I), or a combination thereof, is about the melting temperature of tartaric acid. In some embodiments, the heating temperature for the process for preparing a flavor-grade compound of Formula (I), or a combination thereof, is about 171° C. to about 174° C. In some embodiments, the heating temperature for the process for preparing a flavor-grade compound of Formula (I), or a combination thereof, is about the melting temperature of phosphoric acid. In some embodiments, the heating temperature for the process for preparing a flavor-grade compound of Formula (I), or a combination thereof, is about 42° C. In some embodiments, the heating temperature for the process for preparing a flavor-grade compound of Formula (I), or a combination thereof, is about the melting temperature of benzoic acid. In some embodiments, the heating temperature for the process for preparing a flavor-grade compound of Formula (I), or a combination thereof, is about 122° C. In some embodiments, the heating temperature for the process for preparing a flavor-grade compound of Formula (I), or a combination thereof, is about the melting temperature of maleic acid. In some embodiments, the heating temperature for the process for preparing a flavor-grade compound of Formula (I), or a combination thereof, is about 135° C.

In some embodiments, the reaction time for the process for preparing a flavor-grade compound of Formula (I), or a combination thereof, is 30 minutes to 24 hours. In some embodiments, the reaction time is 30 minutes to 5 hours. In some embodiments, the reaction time is 30 minutes to 4 hours. In some embodiments, the reaction time is 30 minutes to 3 hours. In some embodiments, the reaction time is 30 minutes to 2 hours. In some embodiments, the reaction time is 30 minutes to 1.5 hours. In some embodiments, the reaction time is 30 minutes to one hour. In some embodiments, the reaction time is 30 minutes. In some embodiments, the reaction time is one hour. In some embodiments, the reaction time is 1.5 hours. In some embodiments, the reaction time is two hours. In some embodiments, the reaction time is 2.5 hours. In some embodiments, the reaction time is three hours. In some embodiments, the reaction time is 3.5 hours. In some embodiments, the reaction time is four hours. In some embodiments, the reaction time is 4.5 hours. In some embodiments, the reaction time is five hours. In some embodiments, the reaction time is 5.5 hours. In some embodiments, the reaction time is six hours. In some embodiments, the reaction time is 6.5 hours. In some embodiments, the reaction time is seven hours. In some embodiments, the reaction time is 7.5 hours. In some embodiments, the reaction time is eight hours. In some embodiments, the reaction time is 8.5 hours. In some embodiments, the reaction time is nine hours. In some embodiments, the reaction time is 9.5 hours. In some embodiments, the reaction time is ten hours. In some embodiments, the reaction time is 10.5 hours. In some embodiments, the reaction time is 11 hours. In some embodiments, the reaction time is 11.5 hours. In some embodiments, the reaction time is 12 hours. In some embodiments, the reaction time is 12.5 hours. In some embodiments, the reaction time is 13 hours. In some embodiments, the reaction time is 13.5 hours. In some embodiments, the reaction time is 14 hours. In some embodiments, the reaction time is 14.5 hours. In some embodiments, the reaction time is 15 hours. In some embodiments, the reaction time is 15.5 hours. In some embodiments, the reaction time is 16 hours. In some embodiments, the reaction time is 16.5 hours. In some embodiments, the reaction time is 17 hours. In some embodiments, the reaction time is 17.5 hours. In some embodiments, the reaction time is 18 hours. In some embodiments, the reaction time is 18.5 hours. In some embodiments, the reaction time is 19 hours. In some embodiments, the reaction time is 19.5 hours. In some embodiments, the reaction time is 20 hours. In some embodiments, the reaction time is 20.5 hours. In some embodiments, the reaction time is 21 hours. In some embodiments, the reaction time is 21.5 hours. In some embodiments, the reaction time is 22 hours. In some embodiments, the reaction time is 22.5 hours. In some embodiments, the reaction time is 23 hours. In some embodiments, the reaction time is 23.5 hours. In some embodiments, the reaction time is 24 hours.

In some embodiments, the reaction time for the process for preparing a flavor-grade compound of Formula (I), or a combination thereof, is about 30 minutes to about 24 hours. In some embodiments, the reaction time is about 30 minutes to about 5 hours. In some embodiments, the reaction time is about 30 minutes to about 4 hours. In some embodiments, the reaction time is about 30 minutes to about 3 hours. In some embodiments, the reaction time is about 30 minutes to about 2 hours. In some embodiments, the reaction time is about 30 minutes to about 1.5 hours. In some embodiments, the reaction time is about 30 minutes to about one hour. In some embodiments, the reaction time is about 30 minutes. In some embodiments, the reaction time is about one hour. In some embodiments, the reaction time is about 1.5 hours. In some embodiments, the reaction time is about two hours. In some embodiments, the reaction time is about 2.5 hours. In some embodiments, the reaction time is about three hours. In some embodiments, the reaction time is about 3.5 hours. In some embodiments, the reaction time is about four hours. In some embodiments, the reaction time is about 4.5 hours. In some embodiments, the reaction time is about five hours. In some embodiments, the reaction time is about 5.5 hours. In some embodiments, the reaction time is about six hours. In some embodiments, the reaction time is about 6.5 hours. In some embodiments, the reaction time is about seven hours. In some embodiments, the reaction time is about 7.5 hours. In some embodiments, the reaction time is about eight hours. In some embodiments, the reaction time is about 8.5 hours. In some embodiments, the reaction time is about nine hours. In some embodiments, the reaction time is about 9.5 hours. In some embodiments, the reaction time is about ten hours. In some embodiments, the reaction time is about 10.5 hours. In some embodiments, the reaction time is about 11 hours. In some embodiments, the reaction time is about 11.5 hours. In some embodiments, the reaction time is about 12 hours. In some embodiments, the reaction time is about 12.5 hours. In some embodiments, the reaction time is about 13 hours. In some embodiments, the reaction time is about 13.5 hours. In some embodiments, the reaction time is about 14 hours. In some embodiments, the reaction time is about 14.5 hours. In some embodiments, the reaction time is about 15 hours. In some embodiments, the reaction time is about 15.5 hours. In some embodiments, the reaction time is about 16 hours. In some embodiments, the reaction time is about 16.5 hours. In some embodiments, the reaction time is about 17 hours. In some embodiments, the reaction time is about 17.5 hours. In some embodiments, the reaction time is about 18 hours. In some embodiments, the reaction time is about 18.5 hours. In some embodiments, the reaction time is about 19 hours. In some embodiments, the reaction time is about 19.5 hours. In some embodiments, the reaction time is about 20 hours. In some embodiments, the reaction time is about 20.5 hours. In some embodiments, the reaction time is about 21 hours. In some embodiments, the reaction time is about 21.5 hours.

In some embodiments, the reaction time is about 22 hours. In some embodiments, the reaction time is about 22.5 hours. In some embodiments, the reaction time is about 23 hours. In some embodiments, the reaction time is about 23.5 hours. In some embodiments, the reaction time is about 24 hours.

In some embodiments, the aryl alcohol for the process for preparing a flavor-grade compound of Formula (I), or a combination thereof, is orcinol having the structure:

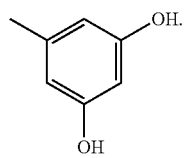

In some embodiments, the orcinol is from a natural source. In some embodiments, the orcinol is from a lichen selected from the group consisting of *Roccella tinctoria*, *Lecanora*, *Roccella fuciformis*, *Roccella pygmaea*, *Roccella phycopsis*, *Lecanora tartarea*, *Variolaria dealbata*, *Ochrolechia parella*, *Parmotrema tinctorum*, *Parmelia*, *Roccella montagnei*, and *Dendrographa leucophoea*. In other embodiments, orcinol is from curculigo orchioides, oakmoss (*Evernia prunastri*), treemoss (*Pseudevernia furfuracea*), or an aloe. In some embodiments, the orcinol is from curculigo orchioides. In certain such embodiments, extraction of orcinol from curculigo orchioides yielded orcinol glucosides. In certain such embodiments, the orcinol glucosides are deglycosylated through one of two ways, enzymatically through reaction with a glucosidase or through reaction with tartaric acid to afford orcinol.

In some embodiments, the trans-ferulic acid for the process for preparing a flavor-grade compound of Formula (I), or a combination thereof, is from cereal bran.

In some embodiments, a flavor-grade compound of Formula (I), or a comestibly acceptable salt, solvate, or enantiomer thereof, or flavor-grade Compound 1 or 4, or a comestibly acceptable salt, solvate, or enantiomer thereof, or flavor-grade Compound 2, 3, 5, or 6, or a comestibly acceptable salt or solvate thereof; or a combination of any of the foregoing compounds, is prepared with the process for preparing a flavor-grade compound of Formula (I) described above. In some embodiments, a combination of flavor-grade Compounds 1-6, or comestibly acceptable salts or solvates thereof, is prepared with the process for preparing a flavor-grade compound of Formula (I) described above. In some embodiments, a combination of flavor-grade Compound 1 and 4, or comestibly acceptable salts, solvates, or enantiomers thereof, is prepared with the process for preparing a flavor-grade compound of Formula (I) described above. In some embodiments, a combination of flavor-grade Compounds 1-3, or comestibly acceptable salts or solvates thereof, is prepared with the process for preparing a flavor-grade compound of Formula (I) described above. In some embodiments wherein a combination of flavor-grade Compounds 1-3, or comestibly acceptable salts or solvates thereof, is prepared with the process for preparing a flavor-grade compound of Formula (I) described above, flavor-grade Compounds 4-6, or comestibly acceptable salts or solvates thereof, are also prepared with the process. In some embodiments, a combination of flavor-grade Compounds 4-6, or comestibly acceptable salts or solvates thereof, is prepared with the process for preparing a flavor-grade compound of Formula (I) described above. In some embodiments, flavor-grade Compound 1, or a comestibly acceptable salt, solvate, or enantiomer thereof, is prepared with the process for preparing a flavor-grade compound of Formula (I) described above. In some embodiments, flavor-grade Compound 2, or a comestibly acceptable salt or solvate thereof, is prepared with the process for preparing a flavor-grade compound of Formula (I) described above. In some embodiments, flavor-grade Compound 3, or a comestibly acceptable salt or solvate thereof, is prepared with the process for preparing a flavor-grade compound of Formula (I) described above. In some embodiments, flavor-grade Compound 4, or a comestibly acceptable salt, solvate, or enantiomer thereof, is prepared with the process for preparing a flavor-grade compound of Formula (I) described above. In some embodiments, flavor-grade Compound 5, or a comestibly acceptable salt or solvate thereof, is prepared with the process for preparing a flavor-grade compound of Formula (I) described above. In some embodiments, flavor-grade Compound 6, or a comestibly acceptable salt or solvate thereof, is prepared with the process for preparing a flavor-grade compound of Formula (I) described above.

In some embodiments, the flavor-grade neoflavonoid compounds are purified from the reaction mixture to afford a mixture of flavor-grade Compounds 1-6. In some embodiments, the flavor-grade neoflavonoid compounds are purified from the reaction mixture to afford a mixture of flavor-grade Compounds 1-3. In some embodiments, the flavor-grade neoflavonoid compounds are purified from the reaction mixture to afford a mixture of flavor-grade Compounds 4-6. In some embodiments, the flavor-grade neoflavonoid compounds are purified from the reaction mixture to afford a mixture of flavor-grade Compounds 1 and 4. In some embodiments, the flavor-grade neoflavonoid compounds are purified from the reaction mixture to afford flavor-grade Compound 1. In some embodiments, the flavor-grade neoflavonoid compounds are purified from the reaction mixture to afford flavor-grade Compound 2. In some embodiments, the flavor-grade neoflavonoid compounds are purified from the reaction mixture to afford flavor-grade Compound 3. In some embodiments, the flavor-grade neoflavonoid compounds are purified from the reaction mixture to afford flavor-grade Compound 4. In some embodiments, the flavor-grade neoflavonoid compounds are purified from the reaction mixture to afford flavor-grade Compound 5. In some embodiments, the flavor-grade neoflavonoid compounds are purified from the reaction mixture to afford flavor-grade Compound 6. In some embodiments, the flavor-grade neoflavonoid compounds are purified by chromatography (e.g., silica gel, reverse phase, ion exchange, or chiral chromatography). In some embodiments, the flavor-grade neoflavonoid compounds are purified by crystallization or recrystallization.

In some embodiments, the flavor-grade neoflavonoid compounds are not purified from the reaction mixture and are used as a crude mixture of flavor-grade Compounds 1-6.

In some embodiments, a 1:1 molar ratio of flavor-grade Compounds 1 and 4, or comestibly acceptable salts, solvates, or enantiomers thereof, is prepared by the process for preparing a flavor-grade compound of Formula (I) described above. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:2 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:3 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:4 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:5 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:6 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:7 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:8 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:9 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:10 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:11 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:12 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:13 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:14 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:15 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:16 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:17 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:18 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:19 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:20 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:30 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:40 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:50 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:100 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:500 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:1000 Compound 1: Compound 4.

In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:2 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:3 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:4 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:5 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:6 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:7 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:8 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:9 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:10 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:11 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:12 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:13 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:14 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:15 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:16 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:17 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:18 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:19 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:20 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:30 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:40 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:50 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:100 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:500 Compound 1: Compound 4. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:1000 Compound 1: Compound 4.

In some embodiments, the molar ratio of flavor-grade Compounds 1 and 4, or comestibly acceptable salts, solvates, or enantiomers thereof, prepared by the process for preparing a flavor-grade compound of Formula (I) described above is 1:2 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:3 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:4 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:5 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:6 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:7 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:8 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:9 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:10 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:11 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:12 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:13 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:14 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:15 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:16 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:17 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:18 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:19 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:20 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:30 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:40 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:50 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:100 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:500 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is 1:1000 Compound 4: Compound 1.

In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:2 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:3 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:4 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:5 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:6 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:7 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:8 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:9 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:10 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:11 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:12 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:13 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:14 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:15 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:16 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:17 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:18 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:19 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:20 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:30 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:40 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:50 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:100 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:500 Compound 4: Compound 1. In some embodiments, the molar ratio of flavor-grade Compounds 1 and 4, or comestibly acceptable salts, solvates, or enantiomers thereof, prepared by the process for preparing a flavor-grade compound of Formula (I) described above is about 1:1000 Compound 4: Compound 1.

In some embodiments, a 1:1 molar ratio of flavor-grade Compounds 2 and 3, or comestibly acceptable salts or solvates thereof, is prepared by the process for preparing a flavor-grade compound of Formula (I) described above. In some embodiments, the molar ratio of flavor-grade Compounds 2 and 3, or comestibly acceptable salts or solvates thereof, prepared by the process for preparing a flavor-grade compound of Formula (I) described above is 1:2 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:3 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:4 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:5 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:6 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:7 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:8 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:9 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:10 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:11 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:12 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:13 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:14 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:15 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:16 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:17 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:18 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:19 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:20 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:30 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:40 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:50 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:100 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:500 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is 1:1000 Compound 2: Compound 3.

In some embodiments, the molar ratio of flavor-grade Compounds 2 and 3, or comestibly acceptable salts or solvates thereof, prepared by the process for preparing a flavor-grade compound of Formula (I) described above is about 1:1. In some embodiments, the molar ratio of flavor-grade Compounds 2 and 3, or comestibly acceptable salts or solvates thereof, prepared by the process for preparing a flavor-grade compound of Formula (I) described above is about 1:2 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:3 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:4 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:5 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:6 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:7 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:8 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:9 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:10 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:11 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:12 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:13 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:14 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:15 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:16 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:17 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:18 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:19 Compound 2:

Compound 3. In some embodiments, the molar ratio of flavor-grade Compounds 2 and 3, or comestibly acceptable salts or solvates thereof, prepared by the process for preparing a flavor-grade compound of Formula (I) described above is about 1:20 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:30 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:40 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:50 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:100 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:500 Compound 2: Compound 3. In some embodiments, the molar ratio of flavor-grade Compounds 2 and 3, or comestibly acceptable salts or solvates thereof, prepared by the process for preparing a flavor-grade compound of Formula (I) described above is about 1:1000 Compound 2: Compound 3.

In some embodiments, the molar ratio of flavor-grade Compounds 2 and 3, or comestibly acceptable salts or solvates thereof, prepared by the process for preparing a flavor-grade compound of Formula (I) described above is 1:2 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:3 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:4 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:5 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:6 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:7 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:8 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:9 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:10 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:11 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:12 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:13 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:14 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:15 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:16 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:17 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:18 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:19 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:20 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:30 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:40 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:50 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:100 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:500 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is 1:1000 Compound 3: Compound 2.

In some embodiments, the molar ratio of flavor-grade Compounds 2 and 3, or comestibly acceptable salts or solvates thereof, prepared by the process for preparing a flavor-grade compound of Formula (I) described above is about 1:2 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:3 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:4 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:5 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:6 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:7 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:8 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:9 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:10 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:11 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:12 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:13 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:14 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:15 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:16 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:17 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:18 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:19 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:20 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:30 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:40 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:50 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:100 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:500 Compound 3: Compound 2. In some embodiments, the molar ratio of flavor-grade Compounds 2 and 3, or comestibly acceptable salts or solvates thereof, prepared by the process for preparing a flavor-grade compound of Formula (I) described above is about 1:1000 Compound 3: Compound 2.

In some embodiments, a 1:1 molar ratio of flavor-grade Compounds 5 and 6, or comestibly acceptable salts or solvates thereof, is prepared by the process for preparing a flavor-grade compound of Formula (I) described above. In some embodiments, the molar ratio of flavor-grade Compounds 5 and 6, or comestibly acceptable salts or solvates thereof, prepared by the process for preparing a flavor-grade compound of Formula (I) described above is 1:2 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:3 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:4 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:5 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:6 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:7 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:8 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:9 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:10 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:11 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:12 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:13 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:14 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:15 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:16 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:17 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:18 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:19 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:20 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:30 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:40 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:50 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:100 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:500 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is 1:1000 Compound 5: Compound 6.

In some embodiments, the molar ratio of flavor-grade Compounds 5 and 6, or comestibly acceptable salts or solvates thereof, prepared by the process for preparing a flavor-grade compound of Formula (I) described above is about 1:1. In some embodiments, the molar ratio of flavor-grade Compounds 5 and 6, or comestibly acceptable salts or solvates thereof, prepared by the process for preparing a flavor-grade compound of Formula (I) described above is about 1:2 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:3 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:4 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:5 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:6 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:7 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:8 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:9 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:10 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:11 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:12 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:13 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:14 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:15 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:16 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:17 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:18 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:19 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:20 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:30 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:40 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:50 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:100 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:500 Compound 5: Compound 6. In some embodiments, the molar ratio of flavor-grade Compounds 5 and 6, or comestibly acceptable salts or solvates thereof, prepared by the process for preparing a flavor-grade compound of Formula (I) described above is about 1:1000 Compound 5: Compound 6.

In some embodiments, the molar ratio of flavor-grade Compounds 5 and 6, or comestibly acceptable salts or solvates thereof, prepared by the process for preparing a flavor-grade compound of Formula (I) described above is 1:2 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:3 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:4 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:5 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:6 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:7 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:8 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:9 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:10 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:11 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:12 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:13 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:14 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:15 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:16 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:17 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:18 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:19 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:20 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:30 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:40 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:50 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:100 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:500 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is 1:1000 Compound 6: Compound 5.

In some embodiments, the molar ratio of flavor-grade Compounds 5 and 6, or comestibly acceptable salts or solvates thereof, prepared by the process for preparing a flavor-grade compound of Formula (I) described above is about 1:2 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:3 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:4 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:5 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:6 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:7 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:8 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:9 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:10 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:11 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:12 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:13 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:14 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:15 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:16 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:17 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:18 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:19 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:20 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:30 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:40 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:50 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:100 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:500 Compound 6: Compound 5. In some embodiments, the molar ratio of flavor-grade Compounds 5 and 6, or comestibly acceptable salts or solvates thereof, prepared by the process for preparing a flavor-grade compound of Formula (I) described above is about 1:1000 Compound 6: Compound 5.

Flavor-Grade Sweet Taste Modulators

According to one aspect, the disclosure provides flavor-grade compounds for modulating sweet taste (e.g., enhancing or potentiating the sweet taste of a sweetener). In some embodiments, these compounds are prepared with the process for preparing a flavor-grade compound of Formula (I), or a combination thereof, described above. In some embodiments, the flavor-grade compounds are used crude from the reaction mixture of the process described above. In some embodiments, the flavor-grade compounds 1 and 4, or comestibly or biologically acceptable salts, enantiomers, or derivatives thereof, are used crude from the reaction mixture.

As used herein, the term "sweet taste modulators" refers to flavor substances with taste modifying properties. Sweetness enhancers are understood to be a type of "sweet taste modulator" where perception of sweetness is increased in a manner not solely attributable to the inherent sweetness of the sweetness enhancer alone. The term "sweetness enhancer" is understood to include at least compositions capable of enhancing or intensifying the perception of sweet taste of sweetener compositions or sweetened compositions. The term "sweetness enhancer" is synonymous with the terms "sweet taste modulating compound," "sweet taste potentiator," "sweetness potentiator," "sweetness amplifier," and "sweetness intensifier." Generally, the flavor-grade sweet taste modulating compounds provided herein (which serve to enhance the perception of sweetness) may enhance or potentiate the sweet taste of sweeteners without providing any noticeable sweet taste by themselves at acceptable use levels; however, the sweetness enhancers may themselves provide sweet taste at concentrations above a sweetness threshold level. It is noted that the sweetness enhancers may be effective as enhancers even if present at concentrations above their sweetness threshold level. In such embodiments, there is major contribution of the sweetness enhancer to the sweetness of the composition via enhancement of the inherently sweet taste attributed to a sweetener, where the sweetener is also present in the composition. As used herein, the term "sweetness threshold level" is understood to include at least the concentration at which the sweetness is perceptible as sweet in the edible compositions. The sweetness threshold level varies for different edible compositions (e.g., in different matrices), and may be varied with respect to the individual perceiving the sweetness.

In all embodiments of the present disclosure, the flavor-grade sweet taste modulator(s) of the present disclosure is a different compound from than the sweetener of the composition. Accordingly, although an ingredient may be characterized as both a sweet taste modulator and a sweetener, in all embodiments of the disclosure, the sweet taste modulator and the sweetener are different ingredients, i.e., the sweet taste modulator and the sweetener are not the same compound.

Each embodiment of the disclosure described herein may be taken alone or in combination with one or more other embodiments of the disclosure.

The present disclosure provides flavor-grade neoflavonoid compounds for modulating or potentiating the sweet taste of a sweetener. The flavor-grade neoflavonoid compounds of this disclosure are capable of modulating or potentiating the sweet taste of a sweetener. The flavor-grade neoflavonoid compound may have a molecular weight less than about 1000, about 500, or about 300 Daltons. In certain embodiments, the flavor-grade neoflavonoid compound is a compound of Formula (I):

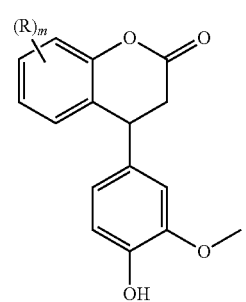

wherein R is —OH, $C_1$-$C_4$ alkyl, —$CO_2$H, acyl or formyl; m is 2 or 3; and at least one R is not OH; or a comestibly acceptable salt, solvate, or enantiomer thereof or a combination of any of the foregoing compounds.

In some embodiments of Formula (I) the flavor-grade compound is:

Compound 1

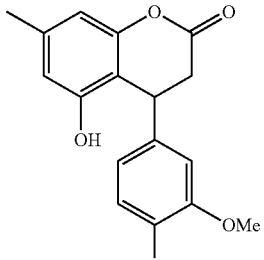

5-hydroxy-4-(4-hydroxy-3-methoxyphenyl)-7-methylchroman-2-one,

Compound 4

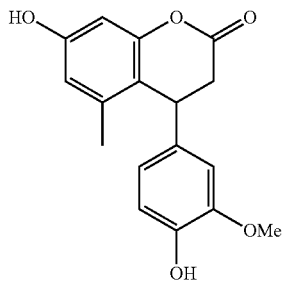 [SMILES: COc1cc([C@H]2CC(=O)Oc3cc(O)cc(C)c32)ccc1O]

7-hydroxy-4-(4-hydroxy-3-methoxyphenyl)-5-methylchroman-2-one, or a comestibly or biologically acceptable salt, solvate, or enantiomer thereof, or Compound 2

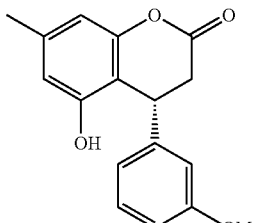

(R)-5-hydroxy-4-(4-hydroxy-3-methoxyphenyl)-7-methylchroman-2-one,

Compound 3

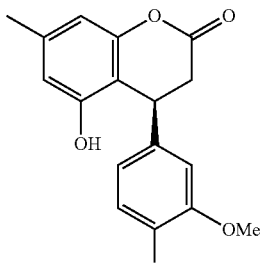

(S)-5-hydroxy-4-(4-hydroxy-3-methoxyphenyl)-7-methylchroman-2-one,

Compound 5

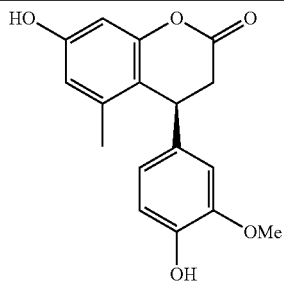

(S)-7-hydroxy-4-(4-hydroxy-3-methoxyphenyl)-5-methylchroman-2-one,

Compound 6

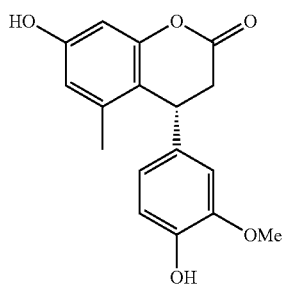 [SMILES: COc1cc([C@H]2CC(=O)Oc3cc(O)cc(C)c32)ccc1O]

(R)-7-hydroxy-4-(4-hydroxy-3-methoxyphenyl)-5-methylchroman-2-one, or a comestibly or biologically acceptable salt or solvate thereof; or a combination of any of the foregoing compounds. In some embodiments, the compound of Formula (I) is a combination of Compounds 1 and 4, or comestibly or biologically acceptable salts, solvates, or enantiomers thereof. In some embodiments, the compound of Formula (I) is a combination of Compounds 1-3, or comestibly or biologically acceptable salts or solvates thereof. In some embodiments wherein the compound of Formula (I) is a combination of Compounds 1-3, or comestibly or biologically acceptable salts or solvates thereof, the combination also comprises a combination of Compounds 4-6, or comestibly or biologically acceptable salts or solvates thereof. In some embodiments, the compound of Formula (I) is a combination of Compounds 4-6, or comestibly or biologically acceptable salts or solvates thereof. In some embodiments, the compound of Formula (I) is a combination of Compounds 1-6, or comestibly or biologically acceptable salts or solvates thereof. In some embodiments, the compound of Formula (I) is Compound 1, or a comestibly or biologically acceptable salt, solvate, or enantiomer thereof. In some embodiments, the compound of Formula (I) is Compound 2, or a comestibly or biologically acceptable salt or solvate thereof. In some embodiments, the compound of Formula (I) is Compound 3, or a comestibly or biologically acceptable salt or solvate thereof. In some embodiments, the compound of Formula (I) is Compound 4, or a comestibly or biologically acceptable salt, solvate, or enantiomer thereof. In some embodiments, the compound of Formula (I) is Compound 5, or a comestibly or biologically acceptable salt or solvate thereof. In some embodiments, the compound of Formula (I) is Compound 6, or a comestibly or biologically acceptable salt or solvate thereof.

In some embodiments, the flavor-grade compound of Formula (I), or a comestibly acceptable salt, solvate, or enantiomer thereof, or flavor-grade Compound 1 or 4, or a comestibly acceptable salt, solvate, or enantiomer thereof, or flavor-grade Compound 2, 3, 5, or 6, or a comestibly acceptable salt or solvate thereof; or a combination of any of the foregoing compounds, is prepared with the process for preparing a flavor-grade compound of Formula (I) described above. In some embodiments, a combination of flavor-grade Compounds 1-6, or comestibly acceptable salts or solvates thereof, is prepared with the process for preparing a flavor-grade compound of Formula (I) described above. In some embodiments, a combination of flavor-grade Compound 1 and 4, or comestibly acceptable salts, solvates, or enantiomers thereof, is prepared with the process for preparing a flavor-grade compound of Formula (I) described above. In some embodiments, a combination of flavor-grade Compounds 1-3, or comestibly acceptable salts or solvates thereof, is prepared with the process for preparing a flavor-grade compound of Formula (I) described above. In some embodiments wherein a combination of flavor-grade Compounds 1-3, or comestibly acceptable salts or solvates thereof, is prepared with the process for preparing a flavor-grade compound of Formula (I) described above, flavor-grade Compounds 4-6, or comestibly acceptable salts or solvates thereof, are also prepared with the process. In some embodiments, a combination of flavor-grade Compounds 4-6, or comestibly acceptable salts or solvates thereof, is prepared with the process for preparing a flavor-grade compound of Formula (I) described above. In some embodiments, flavor-grade Compound 1, or a comestibly acceptable salt, solvate, or enantiomer thereof, is prepared with the process for preparing a flavor-grade compound of Formula (I) described above. In some embodiments, flavor-grade Compound 2, or a comestibly acceptable salt or solvate thereof, is prepared with the process for preparing a flavor-grade compound of Formula (I) described above. In some embodiments, flavor-grade Compound 3, or a comestibly acceptable salt or solvate thereof, is prepared with the process for preparing a flavor-grade compound of Formula (I) described above. In some embodiments, flavor-grade Compound 4, or a comestibly acceptable salt, solvate, or enantiomer thereof, is prepared with the process for preparing a flavor-grade compound of Formula (I) described above. In some embodiments, flavor-grade Compound 5, or a comestibly acceptable salt or solvate thereof, is prepared with the process for preparing a flavor-grade compound of Formula (I) described above. In some embodiments, flavor-grade Compound 6, or a comestibly acceptable salt or solvate thereof, is prepared with the process for preparing a flavor-grade compound of Formula (I) described above.

The term "comestibly or biologically acceptable derivative" refers to any comestibly or biologically acceptable derivative of a sweet taste modulator of the present disclosure, which, upon ingestion, is capable of providing (directly or indirectly) a flavor-grade sweet taste modulator or bitter blocker of the present disclosure, or a polymorph, metabolite, residue or portion thereof, or a combination of flavor-grade sweet taste modulators, characterized by the ability to enhance the perception of a sweet taste attributed to a sweetener or block the perception of bitter taste attributed to a bitter tastant. A "comestible product" is a product suitable for oral use, such as eating or drinking. Therefore, a comestibly acceptable compound is an edible compound.

Sweet taste modulators synergize with sweeteners to enhance or potentiate the perception of sweet taste due to the sweetener. When sweet taste modulators are used above their sweetness threshold level, they synergize with sweeteners to enhance or potentiate the perception of sweet taste due to the sweetener. In such cases, the overall sweetness of a composition comprising a flavor-grade sweet taste modulator, or a combination of flavor-grade sweet taste modulators, and a sweet compound is higher than the mere addition of inherent sweetness due to each of the flavor-grade sweet taste modulators, or the combination of flavor-grade sweet taste modulators, and a sweet compound. For example, if a sweet taste modulator with a sweetness equivalent to 1% sucrose is added to a 5% sucrose solution, the perceived sweetness of the resulting composition would be greater than that of a 6% sucrose solution—with any perceived sweetness greater than a 6% sucrose solution being attributable to the sweetness enhancing properties of the sweet taste modulators. Such an increase in perceived sweetness may be referred to as synergistic, not additive.

The terms "sweetness threshold," and "sweetness recognition threshold," are used interchangeably, herein, and refer to the level at which the lowest known concentration of a certain sweet compound is perceivable as sweet by the human sense of taste. This sweetness recognition threshold also encompasses the sweetness detection threshold, referring to the level at which the lowest known concentration of a certain sweet compound is perceivable by the human sense of taste. The sweetness threshold can vary from person to person. The sweetness threshold can also vary from matrix to matrix (e.g., different sweetness thresholds in water and a carbonated beverage). For example, a sweetness threshold level for sucrose in water could be around 1% or 1.5%. In some embodiments, the flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds is used at a concentration below its sweetness threshold.

The terms "effective concentration" and "effective amount" are used interchangeably herein and refer to an amount sufficient to produce a desired property or result. For example, an effective amount of a flavor-grade sweet taste modulator, or a combination of flavor-grade sweet taste modulators, of the present disclosure is an amount capable of modulating (e.g., enhancing) the perception of sweet taste associated with a sweetener. The term "effective amount" of a flavor-grade sweet taste modulator, or a combination of flavor-grade sweet taste modulators, of the disclosure also refers to an amount which, when added to an edible composition, enhances the sweet taste of, e.g., a sugar, thereby allowing for the maintenance of the perception of a desired sweet flavor of the edible composition. The term "effective amount" also refers to the amount of a flavor-grade sweet taste modulator, or a combination of flavor-grade sweet taste modulators, of the present disclosure capable of modulating (e.g., enhancing) the perception of a sweet taste associated with either a sweetener in a food product or an inherently sweet food product. The flavor-grade sweet taste modulators, or the combination of flavor-grade sweet taste modulators, of the present disclosure may impart a sweetness or taste at certain concentrations and no perceptible sweetness or taste at other concentrations. For example, the flavor-grade sweet taste modulator, or the combination of flavor-grade sweet taste modulators, may be present in an amount such that the taste, such as sweetness, of the sweet taste modulator is imperceptible. The compositions discussed herein include an effective amount of the flavor-grade sweet taste modulator, or the combination of flavor-grade sweet taste modulators. An effective amount of the flavor-grade sweet taste modulator, or the combination of flavor-grade sweet taste modulators, includes an amount sufficient to enhance the perception of sweetness intensity of a sweetener.

In general, a flavor-grade sweet taste modulator, or a combination of flavor-grade sweet taste modulators, of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) enhances the sweetness of a sweetener when the compound is present at a concentration between about 0.001 ppm and about 1000 ppm. In some embodiments, the flavor-grade sweet taste modulator, or the combination of flavor-grade sweet taste modulators, of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) enhances the sweetness of a sweetener when the flavor-grade compound, or the combination of flavor-grade compounds, is present at a concentration between about 0.005 ppm to about 500 ppm; about 0.01 ppm to about 100 ppm; about 0.05 ppm to about 50 ppm; about 0.1 ppm to about 5 ppm; about 0.1 ppm to about 10 ppm; about 0.1 ppm to about 100 ppm; about 1 ppm to about 10 ppm; about 1 ppm to about 30 ppm; about 1 ppm to about 50 ppm; about 10 ppm to about 20 ppm; about 10 ppm to about 25 ppm; about 10 ppm to about 30 ppm; about 1 ppm to about 50 ppm; about 5 ppm to about 50 ppm; about 10 ppm to about 50 ppm; about 30 ppm to about 50 ppm; about 1 ppm to about 60 ppm; about 100 ppm to about 300 ppm; about 100 ppm to about 1000 ppm; or about 30 ppm to about 3000 ppm. In some embodiments, the flavor-grade sweet taste modulator, or the combination of flavor-grade sweet taste modulators, of the present disclosure (e.g., flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) enhances the sweetness of a sweetener when the flavor-grade compound, or the combination of flavor-grade sweet taste modulators, is present at a concentration between about 50 ppm to about 100 ppm; about 100 ppm to about 200 ppm; about 200 ppm to about 300 ppm; about 300 ppm to about 400 ppm; about 400 ppm to about 500 ppm; about 500 ppm to about 600 ppm; about 600 ppm to about 700 ppm; about 700 ppm to about 800 ppm; about 800 ppm to about 900 ppm; about 900 ppm to about 1000 ppm; about 1000 ppm to about 1100 ppm; about 1100 ppm to about 1200 ppm; about 1200 ppm to about 1300 ppm; about 1300 ppm to about 1400 ppm; about 1400 ppm to about 1500 ppm; about 1500 ppm to about 1600 ppm; about 1600 ppm to about 1700 ppm; about 1700 ppm to about 1800 ppm; about 1800 ppm to about 1900 ppm; about 1900 ppm to about 2000 ppm; about 2000 ppm to about 2100 ppm; about 2100 ppm to about 2200 ppm; about 2200 ppm to about 2300 ppm; about 2300 ppm to about 2400 ppm; about 2400 ppm to about 2500 ppm; about 2500 ppm to about 2600 ppm; about 2600 ppm to about 2700 ppm; about 2700 ppm to about 2800 ppm; about 2800 ppm to about 2900 ppm, or about 2900 ppm to about 3000 ppm. In yet other embodiments, the flavor-grade sweet taste modulator, or the combination of flavor-grade sweet taste modulators, of the present disclosure enhances the sweetness of a sweetener when the flavor-grade compound, or the combination of flavor-grade compounds, is present at a concentration of about 0.1 ppm to about 30 ppm; about 1 ppm to about 30 ppm; or about 1 ppm to about 50 ppm. In additional embodiments, the flavor-grade sweet taste modulator, or the combination of flavor-grade sweet taste modulators, of the present disclosure (e.g., flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) enhances the sweetness of a sweetener when the flavor-grade compound, or the combination of flavor-grade compounds, is present at a concentration of about 0.1 ppm to about 5 ppm; about 0.1 ppm to about 4 ppm; about 0.1 ppm to about 3 ppm; about 0.1 ppm to about 2 ppm; about 0.1 ppm to about 1 ppm; about 0.5 ppm to about 5 ppm; about 0.5 ppm to 4 about ppm; about 0.5 ppm to about 3 ppm; about 0.5 ppm to about 2 ppm; about 0.5 ppm to about 1.5 ppm; about 0.5 ppm to about 1 ppm; about 5 ppm to about 15 ppm; about 6 ppm to about 14 ppm; about 7 ppm to about 13 ppm; about 8 ppm to about 12 ppm; about 9 ppm to about 11 ppm; about 25 ppm to about 35 ppm; about 26 ppm to about 34 ppm; about 27 ppm to about 33 ppm; about 28 ppm to about 32 ppm; or about 29 ppm to about 31 ppm.

In yet other embodiments, the flavor-grade sweet taste modulator, or the combination of flavor-grade sweet taste modulators, of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) enhances the sweetness of a sweetener when the flavor-grade compound, or the combination of flavor-grade compounds, is present at a concentration of about 0.1 ppm, about 0.5 ppm, about 1 ppm, about 2 ppm, about 3 ppm, about 4 ppm, about 5 ppm, about 6 ppm, about 7 ppm, about 8 ppm, about 9 ppm, about 10 ppm, about 11 ppm, about 12 ppm, about 13 ppm, about 14 ppm, about 15 ppm, about 16 ppm, about 17 ppm, about 18 ppm, about 19 ppm, about 20 ppm, about 21 ppm, about 22 ppm, about 23 ppm, about 24 ppm, about 25 ppm, about 26 ppm, about 27 ppm, about 28 ppm about, 29 ppm, about 30 ppm, about 31 ppm, about 32 ppm, about 33 ppm, about 34 ppm, about 35 ppm, about 36 ppm, about 37 ppm, about 38 ppm, about 39 ppm, about 40 ppm, about 41 ppm, about 42 ppm, about 43 ppm, about 44 ppm, about 45 ppm, about 46 ppm, about 47 ppm, about 48 ppm, about 49 ppm, about 50 ppm, about 51 ppm, about 52 ppm, about 53 ppm, about 54 ppm, about 55 ppm, about 56 ppm, about 57 ppm, about 58 ppm, about 59 ppm, about 60 ppm, about 61 ppm, about 62 ppm, about 63 ppm, about 64 ppm, about 65 ppm, about 66 ppm, about 67 ppm, about 68 ppm, about 69 ppm, about 70 ppm, about 71 ppm, about 72 ppm, about 73 ppm, about 74 ppm, about 75 ppm, about 76 ppm, about 77 ppm, about 78 ppm, about 79 ppm, about 80 ppm, about 81 ppm, about 82 ppm, about 83 ppm, about 84 ppm, about 85 ppm, about 86 ppm, about 87 ppm, about 88 ppm, about 89 ppm, about 90 ppm, about 91 ppm, about 92 ppm, about 93 ppm, about 94 ppm, about 95 ppm, about 96 ppm, about 97 ppm, about 98 ppm, about 99 ppm, about 100 ppm, about 101 ppm, about 102 ppm, about 103 ppm, about 104 ppm, about 105 ppm, about 106 ppm, about 107 ppm, about 108 ppm, about 109 ppm, about 110 ppm, about 111 ppm, about 112 ppm, about 113 ppm, about 114 ppm, about 115 ppm, about 116 ppm, about 117 ppm, about 118 ppm, about 119 ppm, about 120 ppm, about 121 ppm, about 122 ppm, about 123 ppm, about 124 ppm, about 125 ppm, about 126 ppm, about 127 ppm, about 128 ppm, about 129 ppm, about 130 ppm, about 131 ppm, about 132 ppm, about 133 ppm, about 134 ppm, about 135 ppm, about 136 ppm, about 137 ppm, about 138 ppm, about 139 ppm, about 140 ppm, about 141 ppm, about 142 ppm, about 143 ppm, about 144 ppm, about 145 ppm, about 146 ppm, about 147 ppm, about 148 ppm, about 149 ppm, or about 150 ppm. In some embodiments, the flavor-grade compound, or the combination of flavor-grade compounds, is present at a concentration of about 0.1 ppm. In some embodiments, the flavor-grade compound, or the combination of flavor-grade compounds, is present at a concentration of about 0.5 ppm. In some embodiments, the flavor-grade compound, or the combination of flavor-grade compounds, is present at a concentration of about 1 ppm. In some embodiments, the flavor-grade compound, or the combination of flavor-grade compounds, is present at a concentration of about 2 ppm. In some embodiments, the flavor-grade compound, or the combination of flavor-grade compounds, is present at a concentration of about 3 ppm. In some embodiments, the flavor-grade compound, or the combination of flavor-grade compounds, is present at a concentration of about 4 ppm. In some embodiments, the flavor-grade compound, or the combination of flavor-grade compounds, is present at a concentration of about 5 ppm. In some embodiments, the flavor-grade compound, or the combination of flavor-grade compounds, is present at a concentration of about 6 ppm. In some embodiments, the flavor-grade compound, or the combination of flavor-grade compounds, is present at a concentration of about 7 ppm. In some embodiments, the flavor-grade compound, or the combination of flavor-grade compounds, is present at a concentration of about 8 ppm. In some embodiments, the flavor-grade compound, or the combination of flavor-grade compounds, is present at a concentration of about 9 ppm. In some embodiments, the flavor-grade compound, or the combination of flavor-grade compounds, is present at a concentration of about 10 ppm. In some embodiments, the flavor-grade compound, or the combination of flavor-grade compounds, is present at a concentration of about 11 ppm. In some embodiments, the flavor-grade compound, or the combination of flavor-grade compounds, is present at a concentration of about 12 ppm. In some embodiments, the flavor-grade compound, or the combination of flavor-grade compounds, is present at a concentration of about 13 ppm. In some embodiments, the flavor-grade compound, or the combination of flavor-grade compounds, is present at a concentration of about 14 ppm. In some embodiments, the flavor-grade compound, or the combination of flavor-grade compounds, is present at a concentration of about 15 ppm. In some embodiments, the flavor-grade compound, or the combination of flavor-grade compounds, is present at a concentration of about 16 ppm. In some embodiments, the flavor-grade compound, or the combination of flavor-grade compounds, is present at a concentration of about 17 ppm. In some embodiments, the flavor-grade compound, or the combination of flavor-grade compounds, is present at a concentration of about 18 ppm. In some embodiments, the flavor-grade compound, or the combination of flavor-grade compounds, is present at a concentration of about 19 ppm. In some embodiments, the flavor-grade compound, or the combination of flavor-grade compounds, is present at a concentration of about 20 ppm. In some embodiments, the flavor-grade compound, or the combination of flavor-grade compounds, is present at a concentration of about 21 ppm. In some embodiments, the flavor-grade compound, or the combination of flavor-grade compounds, is present at a concentration of about 22 ppm. In some embodiments, the flavor-grade compound, or the combination of flavor-grade compounds, is present at a concentration of about 23 ppm. In some embodiments, the flavor-grade compound, or the combination of flavor-grade compounds, is present at a concentration of about 24 ppm. In some embodiments, the flavor-grade compound, or the combination of flavor-grade compounds, is present at a concentration of about 25 ppm. In some embodiments, the flavor-grade compound, or the combination of flavor-grade compounds, is present at a concentration of about 26 ppm. In some embodiments, the flavor-grade compound, or the combination of flavor-grade compounds, is present at a concentration of about 27 ppm. In some embodiments, the flavor-grade compound, or the combination of flavor-grade compounds, is present at a concentration of about 28 ppm. In some embodiments, the flavor-grade compound, or the combination of flavor-grade compounds, is present at a concentration of about 29 ppm. In some embodiments, the flavor-grade compound, or the combination of flavor-grade compounds, is present at a concentration of about 30 ppm. In some embodiments, the flavor-grade compound, or the combination of flavor-grade compounds, is present at a concentration of about 31 ppm. In some embodiments, the flavor-grade compound, or the combination of flavor-grade compounds, is present at a concentration of about 32 ppm. In some embodiments, the flavor-grade compound, or the combination of flavor-grade compounds, is present at a concentration of about 33 ppm. In some embodiments, the flavor-grade compound, or the combination of flavor-grade compounds, is present at a concentration of about 34 ppm. In some embodiments, the flavor-grade compound, or the combination of flavor-grade compounds, is present at a concentration of about 35 ppm. In some embodiments, the flavor-grade compound, or the combination of flavor-grade compounds, is present at a concentration of about 36 ppm. In some embodiments, the flavor-grade compound, or the combination of flavor-grade compounds, is present at a concentration of about 37 ppm. In some embodiments, the flavor-grade compound, or the combination of flavor-grade compounds, is present at a concentration of about 38 ppm. In some embodiments, the flavor-grade compound, or the combination of flavor-grade compounds, is present at a concentration of about 39 ppm. In some embodiments, the flavor-grade compound, or the combination of flavor-grade compounds, is present at a concentration of about 40 ppm. In some embodiments, the flavor-grade compound, or the combination of flavor-grade compounds, is present at a concentration of about 41 ppm. In some embodiments, the flavor-grade compound, or the combination of flavor-grade compounds, is present at a concentration of about 42 ppm. In some embodiments, the flavor-grade compound, or the combination of flavor-grade compounds, is present at a concentration of about 43 ppm. In some embodiments, the flavor-grade compound, or the combination of flavor-grade compounds, is present at a concentration of about 44 ppm. In some embodiments, the flavor-grade compound, or the combination of flavor-grade compounds, is present at a concentration of about 45 ppm. In some embodiments, the flavor-grade compound, or the combination of flavor-grade compounds, is present at a concentration of about 46 ppm. In some embodiments, the flavor-grade compound, or the combination of flavor-grade compounds, is present at a concentration of about 47 ppm. In some embodiments, the flavor-grade compound, or the combination of flavor-grade compounds, is present at a concentration of about 48 ppm. In some embodiments, the flavor-grade compound, or the combination of flavor-grade compounds, is present at a concentration of about 49 ppm. In some embodiments, the flavor-grade compound, or the combination of flavor-grade compounds, is present at a concentration of about 50 ppm. In some embodiments, the flavor-grade compound, or the combination of flavor-grade compounds, is present at a concentration of about 51 ppm. In some embodiments, the flavor-grade compound, or the combination of flavor-grade compounds, is present at a concentration of about 52 ppm. In some embodiments, the flavor-grade compound, or the combination of flavor-grade compounds, is present at a concentration of about 53 ppm. In some embodiments, the flavor-grade compound, or the combination of flavor-grade compounds, is present at a concentration of about 54 ppm. In some embodiments, the flavor-grade compound, or the combination of flavor-grade compounds, is present at a concentration of about 55 ppm. In some embodiments, the flavor-grade compound, or the combination of flavor-grade compounds, is present at a concentration of about 56 ppm. In some embodiments, the flavor-grade compound, or the combination of flavor-grade compounds, is present at a concentration of about 57 ppm. In some embodiments, the flavor-grade compound, or the combination of flavor-grade compounds, is present at a concentration of about 58 ppm. In some embodiments, the flavor-grade compound, or the combination of flavor-grade compounds, is present at a concentration of about 59 ppm. In some embodiments, the flavor-grade compound, or the combination of flavor-grade compounds, is present at a concentration of about 60 ppm. In some embodiments, the flavor-grade compound, or the combination of flavor-grade compounds, is present at a concentration of about 61 ppm. In some embodiments, the flavor-grade compound, or the combination of flavor-grade compounds, is present at a concentration of about 62 ppm. In some embodiments, the flavor-grade compound, or the combination of flavor-grade compounds, is present at a concentration of about 63 ppm. In some embodiments, the flavor-grade compound, or the combination of flavor-grade compounds, is present at a concentration of about 64 ppm. In some embodiments, the flavor-grade compound, or the combination of flavor-grade compounds, is present at a concentration of about 65 ppm. In some embodiments, the flavor-grade compound, or the combination of flavor-grade compounds, is present at a concentration of about 66 ppm. In some embodiments, the flavor-grade compound, or the combination of flavor-grade compounds, is present at a concentration of about 67 ppm. In some embodiments, the flavor-grade compound, or the combination of flavor-grade compounds, is present at a concentration of about 68 ppm. In some embodiments, the flavor-grade compound, or the combination of flavor-grade compounds, is present at a concentration of about 69 ppm. In some embodiments, the flavor-grade compound, or the combination of flavor-grade compounds, is present at a concentration of about 70 ppm. In some embodiments, the flavor-grade compound, or the combination of flavor-grade compounds, is present at a concentration of about 71 ppm. In some embodiments, the flavor-grade compound, or the combination of flavor-grade compounds, is present at a concentration of about 72 ppm. In some embodiments, the flavor-grade compound, or the combination of flavor-grade compounds, is present at a concentration of about 73 ppm. In some embodiments, the flavor-grade compound, or the combination of flavor-grade compounds, is present at a concentration of about 74 ppm. In some embodiments, the flavor-grade compound, or the combination of flavor-grade compounds, is present at a concentration of about 75 ppm. In some embodiments, the flavor-grade compound, or the combination of flavor-grade compounds, is present at a concentration of about 76 ppm. In some embodiments, the flavor-grade compound, or the combination of flavor-grade compounds, is present at a concentration of about 77 ppm. In some embodiments, the flavor-grade compound, or the combination of flavor-grade compounds, is present at a concentration of about 78 ppm. In some embodiments, the flavor-grade compound, or the combination of flavor-grade compounds, is present at a concentration of about 79 ppm. In some embodiments, the flavor-grade compound, or the combination of flavor-grade compounds, is present at a concentration of about 80 ppm. In some embodiments, the flavor-grade compound, or the combination of flavor-grade compounds, is present at a concentration of about 81 ppm. In some embodiments, the flavor-grade compound, or the combination of flavor-grade compounds, is present at a concentration of about 82 ppm. In some embodiments, the flavor-grade compound, or the combination of flavor-grade compounds, is present at a concentration of about 83 ppm. In some embodiments, the flavor-grade compound, or the combination of flavor-grade compounds, is present at a concentration of about 84 ppm. In some embodiments, the flavor-grade compound, or the combination of flavor-grade compounds, is present at a concentration of about 85 ppm. In some embodiments, the flavor-grade compound, or the combination of flavor-grade compounds, is present at a concentration of about 86 ppm. In some embodiments, the flavor-grade compound, or the combination of flavor-grade compounds, is present at a concentration of about 87 ppm. In some embodiments, the flavor-grade compound, or the combination of flavor-grade compounds, is present at a concentration of about 88 ppm. In some embodiments, the flavor-grade compound, or the combination of flavor-grade compounds, is present at a concentration of about 89 ppm. In some embodiments, the flavor-grade compound, or the combination of flavor-grade compounds, is present at a concentration of about 90 ppm. In some embodiments, the flavor-grade compound, or the combination of flavor-grade compounds, is present at a concentration of about 91 ppm. In some embodiments, the flavor-grade compound, or the combination of flavor-grade compounds, is present at a concentration of about 92 ppm. In some embodiments, the flavor-grade compound, or the combination of flavor-grade compounds, is present at a concentration of about 93 ppm. In some embodiments, the flavor-grade compound, or the combination of flavor-grade compounds, is present at a concentration of about 94 ppm. In some embodiments, the flavor-grade compound, or the combination of flavor-grade compounds, is present at a concentration of about 95 ppm. In some embodiments, the flavor-grade compound, or the combination of flavor-grade compounds, is present at a concentration of about 96 ppm. In some embodiments, the flavor-grade compound, or the combination of flavor-grade compounds, is present at a concentration of about 97 ppm. In some embodiments, the flavor-grade compound, or the combination of flavor-grade compounds, is present at a concentration of about 98 ppm. In some embodiments, the flavor-grade compound, or the combination of flavor-grade compounds, is present at a concentration of about 99 ppm. In some embodiments, the flavor-grade compound, or the combination of flavor-grade compounds, is present at a concentration of about 100 ppm. In some embodiments, the flavor-grade compound, or the combination of flavor-grade compounds, is present at a concentration of about 101 ppm. In some embodiments, the flavor-grade compound, or the combination of flavor-grade compounds, is present at a concentration of about 102 ppm. In some embodiments, the flavor-grade compound, or the combination of flavor-grade compounds, is present at a concentration of about 103 ppm. In some embodiments, the flavor-grade compound, or the combination of flavor-grade compounds, is present at a concentration of about 104 ppm. In some embodiments, the flavor-grade compound, or the combination of flavor-grade compounds, is present at a concentration of about 105 ppm. In some embodiments, the flavor-grade compound, or the combination of flavor-grade compounds, is present at a concentration of about 106 ppm. In some embodiments, the flavor-grade compound, or the combination of flavor-grade compounds, is present at a concentration of about 107 ppm. In some embodiments, the flavor-grade compound, or the combination of flavor-grade compounds, is present at a concentration of about 108 ppm. In some embodiments, the flavor-grade compound, or the combination of flavor-grade compounds, is present at a concentration of about 109 ppm. In some embodiments, the flavor-grade compound, or the combination of flavor-grade compounds, is present at a concentration of about 110 ppm. In some embodiments, the flavor-grade compound, or the combination of flavor-grade compounds, is present at a concentration of about 111 ppm. In some embodiments, the flavor-grade compound, or the combination of flavor-grade compounds, is present at a concentration of about 112 ppm. In some embodiments, the flavor-grade compound, or the combination of flavor-grade compounds, is present at a concentration of about 113 ppm. In some embodiments, the flavor-grade compound, or the combination of flavor-grade compounds, is present at a concentration of about 114 ppm. In some embodiments, the flavor-grade compound, or the combination of flavor-grade compounds, is present at a concentration of about 115 ppm. In some embodiments, the flavor-grade compound, or the combination of flavor-grade compounds, is present at a concentration of about 116 ppm. In some embodiments, the flavor-grade compound, or the combination of flavor-grade compounds, is present at a concentration of about 117 ppm. In some embodiments, the flavor-grade compound, or the combination of flavor-grade compounds, is present at a concentration of about 118 ppm. In some embodiments, the flavor-grade compound, or the combination of flavor-grade compounds, is present at a concentration of about 119 ppm. In some embodiments, the flavor-grade compound, or the combination of flavor-grade compounds, is present at a concentration of about 120 ppm. In some embodiments, the flavor-grade compound, or the combination of flavor-grade compounds, is present at a concentration of about 121 ppm. In some embodiments, the flavor-grade compound, or the combination of flavor-grade compounds, is present at a concentration of about 122 ppm. In some embodiments, the flavor-grade compound, or the combination of flavor-grade compounds, is present at a concentration of about 123 ppm. In some embodiments, the flavor-grade compound, or the combination of flavor-grade compounds, is present at a concentration of about 124 ppm. In some embodiments, the flavor-grade compound, or the combination of flavor-grade compounds, is present at a concentration of about 125 ppm. In some embodiments, the flavor-grade compound, or the combination of flavor-grade compounds, is present at a concentration of about 126 ppm. In some embodiments, the flavor-grade compound, or the combination of flavor-grade compounds, is present at a concentration of about 127 ppm. In some embodiments, the flavor-grade compound, or the combination of flavor-grade compounds, is present at a concentration of about 128 ppm. In some embodiments, the flavor-grade compound, or the combination of flavor-grade compounds, is present at a concentration of about 129 ppm. In some embodiments, the flavor-grade compound, or the combination of flavor-grade compounds, is present at a concentration of about 130 ppm. In some embodiments, the flavor-grade compound, or the combination of flavor-grade compounds, is present at a concentration of about 131 ppm. In some embodiments, the flavor-grade compound, or the combination of flavor-grade compounds, is present at a concentration of about 132 ppm. In some embodiments, the flavor-grade compound, or the combination of flavor-grade compounds, is present at a concentration of about 133 ppm. In some embodiments, the flavor-grade compound, or the combination of flavor-grade compounds, is present at a concentration of about 134 ppm. In some embodiments, the flavor-grade compound, or the combination of flavor-grade compounds, is present at a concentration of about 135 ppm. In some embodiments, the flavor-grade compound, or the combination of flavor-grade compounds, is present at a concentration of about 136 ppm. In some embodiments, the flavor-grade compound, or the combination of flavor-grade compounds, is present at a concentration of about 137 ppm. In some embodiments, the flavor-grade compound, or the combination of flavor-grade compounds, is present at a concentration of about 138 ppm. In some embodiments, the flavor-grade compound, or the combination of flavor-grade compounds, is present at a concentration of about 139 ppm. In some embodiments, the flavor-grade compound, or the combination of flavor-grade compounds, is present at a concentration of about 140 ppm. In some embodiments, the flavor-grade compound, or the combination of flavor-grade compounds, is present at a concentration of about 141 ppm. In some embodiments, the flavor-grade compound, or the combination of flavor-grade compounds, is present at a concentration of about 142 ppm. In some embodiments, the flavor-grade compound, or the combination of flavor-grade compounds, is present at a concentration of about 143 ppm. In some embodiments, the flavor-grade compound, or the combination of flavor-grade compounds, is present at a concentration of about 144 ppm. In some embodiments, the flavor-grade compound, or the combination of flavor-grade compounds, is present at a concentration of about 145 ppm. In some embodiments, the flavor-grade compound, or the combination of flavor-grade compounds, is present at a concentration of about 146 ppm. In some embodiments, the flavor-grade compound, or the combination of flavor-grade compounds, is present at a concentration of about 147 ppm. In some embodiments, the flavor-grade compound, or the combination of flavor-grade compounds, is present at a concentration of about 148 ppm. In some embodiments, the flavor-grade compound, or the combination of flavor-grade compounds, is present at a concentration of about 149 ppm. In some embodiments, the flavor-grade compound, or the combination of flavor-grade compounds, is present at a concentration of about 150 ppm.

The flavor-grade sweet taste modulator, or the combination of flavor-grade sweet taste modulators, of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) may enhance the sweetness of a sweetener when the flavor-grade compound, or the combination of flavor-grade compounds, is present at a concentration of 0.1 ppm, 0.5 ppm, 1 ppm, 2 ppm, 3 ppm, 4 ppm, 5 ppm, 6 ppm, 7 ppm, 8 ppm, 9 ppm, 10 ppm, 11 ppm, 12 ppm, 13 ppm, 14 ppm, 15 ppm, 16 ppm, 17 ppm, 18 ppm, 19 ppm, 20 ppm, 21 ppm, 22 ppm, 23 ppm, 24 ppm, 25 ppm, 26 ppm, 27 ppm, 28 ppm, 29 ppm, 30 ppm, 31 ppm, 32 ppm, 33 ppm, 34 ppm, 35 ppm, 36 ppm, 37 ppm, 38 ppm, 39 ppm, 40 ppm, 41 ppm, 42 ppm, 43 ppm, 44 ppm, 45 ppm, 46 ppm, 47 ppm, 48 ppm, 49 ppm, 50 ppm, 51 ppm, 52 ppm, 53 ppm, 54 ppm, 55 ppm, 56 ppm, 57 ppm, 58 ppm, 59 ppm, 60 ppm, 61 ppm, 62 ppm, 63 ppm, 64 ppm, 65 ppm, 66 ppm, 67 ppm, 68 ppm, 69 ppm, 70 ppm, 71 ppm, 72 ppm, 73 ppm, 74 ppm, 75 ppm, 76 ppm, 77 ppm, 78 ppm, 79 ppm, 80 ppm, 81 ppm, 82 ppm, 83 ppm, 84 ppm, 85 ppm, 86 ppm, 87 ppm, 88 ppm, 89 ppm, 90 ppm, 91 ppm, 92 ppm, 93 ppm, 94 ppm, 95 ppm, 96 ppm, 97 ppm, 98 ppm, 99 ppm, 100 ppm, 101 ppm, 102 ppm, 103 ppm, 104 ppm, 105 ppm, 106 ppm, 107 ppm, 108 ppm, 109 ppm, 110 ppm, 111 ppm, 112 ppm, 113 ppm, 114 ppm, 115 ppm, 116 ppm, 117 ppm, 118 ppm, 119 ppm, 120 ppm, 121 ppm, 122 ppm, 123 ppm, 124 ppm, 125 ppm, 126 ppm, 127 ppm, 128 ppm, 129 ppm, 130 ppm, 131 ppm, 132 ppm, 133 ppm, 134 ppm, 135 ppm, 136 ppm, 137 ppm, 138 ppm, 139 ppm, 140 ppm, 141 ppm, 142 ppm, 143 ppm, 144 ppm, 145 ppm, 146 ppm, 147 ppm, 148 ppm, 149 ppm, or 150 ppm. In some embodiments, the flavor-grade compound, or the combination of flavor-grade compounds, is present at a concentration of 0.1 ppm. In some embodiments, the flavor-grade compound is, or the combination of flavor-grade compounds, present at a concentration of 0.5 ppm. In some embodiments, the flavor-grade compound, or the combination of flavor-grade compounds, is present at a concentration of 1 ppm. In some embodiments, the flavor-grade compound, or the combination of flavor-grade compounds, is present at a concentration of 2 ppm. In some embodiments, the flavor-grade compound, or the combination of flavor-grade compounds, is present at a concentration of 3 ppm. In some embodiments, the flavor-grade compound, or the combination of flavor-grade compounds, is present at a concentration of 4 ppm. In some embodiments, the flavor-grade compound, or the combination of flavor-grade compounds, is present at a concentration of 5 ppm. In some embodiments, the flavor-grade compound, or the combination of flavor-grade compounds, is present at a concentration of 6 ppm. In some embodiments, the flavor-grade compound, or the combination of flavor-grade compounds, is present at a concentration of 7 ppm. In some embodiments, the flavor-grade compound, or the combination of flavor-grade compounds, is present at a concentration of 8 ppm. In some embodiments, the flavor-grade compound, or the combination of flavor-grade compounds, is present at a concentration of 9 ppm. In some embodiments, the flavor-grade compound, or the combination of flavor-grade compounds, is present at a concentration of 10 ppm. In some embodiments, the flavor-grade compound, or the combination of flavor-grade compounds, is present at a concentration of 11 ppm. In some embodiments, the flavor-grade compound, or the combination of flavor-grade compounds, is present at a concentration of 12 ppm. In some embodiments, the flavor-grade compound, or the combination of flavor-grade compounds, is present at a concentration of 13 ppm. In some embodiments, the flavor-grade compound, or the combination of flavor-grade compounds, is present at a concentration of 14 ppm. In some embodiments, the flavor-grade compound, or the combination of flavor-grade compounds, is present at a concentration of 15 ppm. In some embodiments, the flavor-grade compound, or the combination of flavor-grade compounds, is present at a concentration of 16 ppm. In some embodiments, the flavor-grade compound, or the combination of flavor-grade compounds, is present at a concentration of 17 ppm. In some embodiments, the flavor-grade compound, or the combination of flavor-grade compounds, is present at a concentration of 18 ppm. In some embodiments, the flavor-grade compound, or the combination of flavor-grade compounds, is present at a concentration of 19 ppm. In some embodiments, the flavor-grade compound, or the combination of flavor-grade compounds, is present at a concentration of 20 ppm. In some embodiments, the flavor-grade compound, or the combination of flavor-grade compounds, is present at a concentration of 21 ppm. In some embodiments, the flavor-grade compound, or the combination of flavor-grade compounds, is present at a concentration of 22 ppm. In some embodiments, the flavor-grade compound, or the combination of flavor-grade compounds, is present at a concentration of 23 ppm. In some embodiments, the flavor-grade compound, or the combination of flavor-grade compounds, is present at a concentration of 24 ppm. In some embodiments, the flavor-grade compound, or the combination of flavor-grade compounds, is present at a concentration of 25 ppm. In some embodiments, the flavor-grade compound, or the combination of flavor-grade compounds, is present at a concentration of 26 ppm. In some embodiments, the flavor-grade compound, or the combination of flavor-grade compounds, is present at a concentration of 27 ppm. In some embodiments, the flavor-grade compound, or the combination of flavor-grade compounds, is present at a concentration of 28 ppm. In some embodiments, the flavor-grade compound, or the combination of flavor-grade compounds, is present at a concentration of 29 ppm. In some embodiments, the flavor-grade compound, or the combination of flavor-grade compounds, is present at a concentration of 30 ppm. In some embodiments, the flavor-grade compound, or the combination of flavor-grade compounds, is present at a concentration of 31 ppm. In some embodiments, the flavor-grade compound, or the combination of flavor-grade compounds, is present at a concentration of 32 ppm. In some embodiments, the flavor-grade compound, or the combination of flavor-grade compounds, is present at a concentration of 33 ppm. In some embodiments, the flavor-grade compound, or the combination of flavor-grade compounds, is present at a concentration of 34 ppm. In some embodiments, the flavor-grade compound, or the combination of flavor-grade compounds, is present at a concentration of 35 ppm. In some embodiments, the flavor-grade compound, or the combination of flavor-grade compounds, is present at a concentration of 36 ppm. In some embodiments, the flavor-grade compound, or the combination of flavor-grade compounds, is present at a concentration of 37 ppm. In some embodiments, the flavor-grade compound, or the combination of flavor-grade compounds, is present at a concentration of 38 ppm. In some embodiments, the flavor-grade compound, or the combination of flavor-grade compounds, is present at a concentration of 39 ppm. In some embodiments, the flavor-grade compound, or the combination of flavor-grade compounds, is present at a concentration of 40 ppm. In some embodiments, the flavor-grade compound, or the combination of flavor-grade compounds, is present at a concentration of 41 ppm. In some embodiments, the flavor-grade compound, or the combination of flavor-grade compounds, is present at a concentration of 42 ppm. In some embodiments, the flavor-grade compound, or the combination of flavor-grade compounds, is present at a concentration of 43 ppm. In some embodiments, the flavor-grade compound, or the combination of flavor-grade compounds, is present at a concentration of 44 ppm. In some embodiments, the flavor-grade compound is present at a concentration of 45 ppm. In some embodiments, the flavor-grade compound, or the combination of flavor-grade compounds, is present at a concentration of 46 ppm. In some embodiments, the flavor-grade compound, or the combination of flavor-grade compounds, is present at a concentration of 47 ppm. In some embodiments, the flavor-grade compound, or the combination of flavor-grade compounds, is present at a concentration of 48 ppm. In some embodiments, the flavor-grade compound, or the combination of flavor-grade compounds, is present at a concentration of 49 ppm. In some embodiments, the flavor-grade compound, or the combination of flavor-grade compounds, is present at a concentration of 50 ppm. In some embodiments, the flavor-grade compound, or the combination of flavor-grade compounds, is present at a concentration of 51 ppm. In some embodiments, the flavor-grade compound, or the combination of flavor-grade compounds, is present at a concentration of 52 ppm. In some embodiments, the flavor-grade compound, or the combination of flavor-grade compounds, is present at a concentration of 53 ppm. In some embodiments, the flavor-grade compound, or the combination of flavor-grade compounds, is present at a concentration of 54 ppm. In some embodiments, the flavor-grade compound, or the combination of flavor-grade compounds, is present at a concentration of 55 ppm. In some embodiments, the flavor-grade compound, or the combination of flavor-grade compounds, is present at a concentration of 56 ppm. In some embodiments, the flavor-grade compound, or the combination of flavor-grade compounds, is present at a concentration of 57 ppm. In some embodiments, the flavor-grade compound, or the combination of flavor-grade compounds, is present at a concentration of 58 ppm. In some embodiments, the flavor-grade compound, or the combination of flavor-grade compounds, is present at a concentration of 59 ppm. In some embodiments, the flavor-grade compound, or the combination of flavor-grade compounds, is present at a concentration of 60 ppm. In some embodiments, the flavor-grade compound, or the combination of flavor-grade compounds, is present at a concentration of 61 ppm. In some embodiments, the flavor-grade compound, or the combination of flavor-grade compounds, is present at a concentration of 62 ppm. In some embodiments, the flavor-grade compound, or the combination of flavor-grade compounds, is present at a concentration of 63 ppm. In some embodiments, the flavor-grade compound, or the combination of flavor-grade compounds, is present at a concentration of 64 ppm. In some embodiments, the flavor-grade compound, or the combination of flavor-grade compounds, is present at a concentration of 65 ppm. In some embodiments, the flavor-grade compound, or the combination of flavor-grade compounds, is present at a concentration of 66 ppm. In some embodiments, the flavor-grade compound, or the combination of flavor-grade compounds, is present at a concentration of 67 ppm. In some embodiments, the flavor-grade compound, or the combination of flavor-grade compounds, is present at a concentration of 68 ppm. In some embodiments, the flavor-grade compound, or the combination of flavor-grade compounds, is present at a concentration of 69 ppm. In some embodiments, the flavor-grade compound, or the combination of flavor-grade compounds, is present at a concentration of 70 ppm. In some embodiments, the flavor-grade compound, or the combination of flavor-grade compounds, is present at a concentration of 71 ppm. In some embodiments, the flavor-grade compound, or the combination of flavor-grade compounds, is present at a concentration of 72 ppm. In some embodiments, the flavor-grade compound, or the combination of flavor-grade compounds, is present at a concentration of 73 ppm. In some embodiments, the flavor-grade compound, or the combination of flavor-grade compounds, is present at a concentration of 74 ppm. In some embodiments, the flavor-grade compound, or the combination of flavor-grade compounds, is present at a concentration of 75 ppm. In some embodiments, the flavor-grade compound, or the combination of flavor-grade compounds, is present at a concentration of 76 ppm. In some embodiments, the flavor-grade compound, or the combination of flavor-grade compounds, is present at a concentration of 77 ppm. In some embodiments, the flavor-grade compound, or the combination of flavor-grade compounds, is present at a concentration of 78 ppm. In some embodiments, the flavor-grade compound, or the combination of flavor-grade compounds, is present at a concentration of 79 ppm. In some embodiments, the flavor-grade compound, or the combination of flavor-grade compounds, is present at a concentration of 80 ppm. In some embodiments, the flavor-grade compound, or the combination of flavor-grade compounds, is present at a concentration of 81 ppm. In some embodiments, the flavor-grade compound, or the combination of flavor-grade compounds, is present at a concentration of 82 ppm. In some embodiments, the flavor-grade compound, or the combination of flavor-grade compounds, is present at a concentration of 83 ppm. In some embodiments, the flavor-grade compound, or the combination of flavor-grade compounds, is present at a concentration of 84 ppm. In some embodiments, the flavor-grade compound, or the combination of flavor-grade compounds, is present at a concentration of 85 ppm. In some embodiments, the flavor-grade compound, or the combination of flavor-grade compounds, is present at a concentration of 86 ppm. In some embodiments, the flavor-grade compound, or the combination of flavor-grade compounds, is present at a concentration of 87 ppm. In some embodiments, the flavor-grade compound, or the combination of flavor-grade compounds, is present at a concentration of 88 ppm. In some embodiments, the flavor-grade compound, or the combination of flavor-grade compounds, is present at a concentration of 89 ppm. In some embodiments, the flavor-grade compound, or the combination of flavor-grade compounds, is present at a concentration of 90 ppm. In some embodiments, the flavor-grade compound, or the combination of flavor-grade compounds, is present at a concentration of 91 ppm. In some embodiments, the flavor-grade compound, or the combination of flavor-grade compounds, is present at a concentration of 92 ppm. In some embodiments, the flavor-grade compound, or the combination of flavor-grade compounds, is present at a concentration of 93 ppm. In some embodiments, the flavor-grade compound, or the combination of flavor-grade compounds, is present at a concentration of 94 ppm. In some embodiments, the flavor-grade compound, or the combination of flavor-grade compounds, is present at a concentration of 95 ppm. In some embodiments, the flavor-grade compound, or the combination of flavor-grade compounds, is present at a concentration of 96 ppm. In some embodiments, the flavor-grade compound, or the combination of flavor-grade compounds, is present at a concentration of 97 ppm. In some embodiments, the flavor-grade compound, or the combination of flavor-grade compounds, is present at a concentration of 98 ppm. In some embodiments, the flavor-grade compound, or the combination of flavor-grade compounds, is present at a concentration of 99 ppm. In some embodiments, the flavor-grade compound, or the combination of flavor-grade compounds, is present at a concentration of 100 ppm. In some embodiments, the flavor-grade compound, or the combination of flavor-grade compounds, is present at a concentration of 101 ppm. In some embodiments, the flavor-grade compound, or the combination of flavor-grade compounds, is present at a concentration of 102 ppm. In some embodiments, the flavor-grade compound, or the combination of flavor-grade compounds, is present at a concentration of 103 ppm. In some embodiments, the flavor-grade compound, or the combination of flavor-grade compounds, is present at a concentration of 104 ppm. In some embodiments, the flavor-grade compound, or the combination of flavor-grade compounds, is present at a concentration of 105 ppm. In some embodiments, the flavor-grade compound, or the combination of flavor-grade compounds, is present at a concentration of 106 ppm. In some embodiments, the flavor-grade compound, or the combination of flavor-grade compounds, is present at a concentration of 107 ppm. In some embodiments, the flavor-grade compound is present at a concentration of 108 ppm. In some embodiments, the flavor-grade compound, or the combination of flavor-grade compounds, is present at a concentration of 109 ppm. In some embodiments, the flavor-grade compound, or the combination of flavor-grade compounds, is present at a concentration of 110 ppm. In some embodiments, the flavor-grade compound, or the combination of flavor-grade compounds, is present at a concentration of 111 ppm. In some embodiments, the flavor-grade compound, or the combination of flavor-grade compounds, is present at a concentration of 112 ppm. In some embodiments, the flavor-grade compound, or the combination of flavor-grade compounds, is present at a concentration of 113 ppm. In some embodiments, the flavor-grade compound, or the combination of flavor-grade compounds, is present at a concentration of 114 ppm. In some embodiments, the flavor-grade compound, or the combination of flavor-grade compounds, is present at a concentration of 115 ppm. In some embodiments, the flavor-grade compound, or the combination of flavor-grade compounds, is present at a concentration of 116 ppm. In some embodiments, the flavor-grade compound, or the combination of flavor-grade compounds, is present at a concentration of 117 ppm. In some embodiments, the flavor-grade compound, or the combination of flavor-grade compounds, is present at a concentration of 118 ppm. In some embodiments, the flavor-grade compound, or the combination of flavor-grade compounds, is present at a concentration of 119 ppm. In some embodiments, the flavor-grade compound, or the combination of flavor-grade compounds, is present at a concentration of 120 ppm. In some embodiments, the flavor-grade compound, or the combination of flavor-grade compounds, is present at a concentration of 121 ppm. In some embodiments, the flavor-grade compound, or the combination of flavor-grade compounds, is present at a concentration of 122 ppm. In some embodiments, the flavor-grade compound, or the combination of flavor-grade compounds, is present at a concentration of 123 ppm. In some embodiments, the flavor-grade compound, or the combination of flavor-grade compounds, is present at a concentration of 124 ppm. In some embodiments, the flavor-grade compound, or the combination of flavor-grade compounds, is present at a concentration of 125 ppm. In some embodiments, the flavor-grade compound, or the combination of flavor-grade compounds, is present at a concentration of 126 ppm. In some embodiments, the flavor-grade compound, or the combination of flavor-grade compounds, is present at a concentration of 127 ppm. In some embodiments, the flavor-grade compound, or the combination of flavor-grade compounds, is present at a concentration of 128 ppm. In some embodiments, the flavor-grade compound, or the combination of flavor-grade compounds, is present at a concentration of 129 ppm. In some embodiments, the flavor-grade compound, or the combination of flavor-grade compounds, is present at a concentration of 130 ppm. In some embodiments, the flavor-grade compound, or the combination of flavor-grade compounds, is present at a concentration of 131 ppm. In some embodiments, the flavor-grade compound, or the combination of flavor-grade compounds, is present at a concentration of 132 ppm. In some embodiments, the flavor-grade compound, or the combination of flavor-grade compounds, is present at a concentration of 133 ppm. In some embodiments, the flavor-grade compound, or the combination of flavor-grade compounds, is present at a concentration of 134 ppm. In some embodiments, the flavor-grade compound, or the combination of flavor-grade compounds, is present at a concentration of 135 ppm. In some embodiments, the flavor-grade compound, or the combination of flavor-grade compounds, is present at a concentration of 136 ppm. In some embodiments, the flavor-grade compound, or the combination of flavor-grade compounds, is present at a concentration of 137 ppm. In some embodiments, the flavor-grade compound, or the combination of flavor-grade compounds, is present at a concentration of 138 ppm. In some embodiments, the flavor-grade compound, or the combination of flavor-grade compounds, is present at a concentration of 139 ppm. In some embodiments, the flavor-grade compound, or the combination of flavor-grade compounds, is present at a concentration of 140 ppm. In some embodiments, the flavor-grade compound, or the combination of flavor-grade compounds, is present at a concentration of 141 ppm. In some embodiments, the flavor-grade compound, or the combination of flavor-grade compounds, is present at a concentration of 142 ppm. In some embodiments, the flavor-grade compound, or the combination of flavor-grade compounds, is present at a concentration of 143 ppm. In some embodiments, the flavor-grade compound, or the combination of flavor-grade compounds, is present at a concentration of 144 ppm. In some embodiments, the flavor-grade compound, or the combination of flavor-grade compounds, is present at a concentration of 145 ppm. In some embodiments, the flavor-grade compound, or the combination of flavor-grade compounds, is present at a concentration of 146 ppm. In some embodiments, the flavor-grade compound, or the combination of flavor-grade compounds, is present at a concentration of 147 ppm. In some embodiments, the flavor-grade compound, or the combination of flavor-grade compounds, is present at a concentration of 148 ppm. In some embodiments, the flavor-grade compound, or the combination of flavor-grade compounds, is present at a concentration of 149 ppm. In some embodiments, the flavor-grade compound, or the combination of flavor-grade compounds, is present at a concentration of 150 ppm.

In other embodiments, the flavor-grade sweet taste modulator, or the combination of flavor-grade sweet taste modulators, of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) enhances the sweetness of a sweetener when the flavor-grade compound, or the combination of flavor-grade compounds, is present at a concentration of more than about 0.5 ppm, about 1 ppm, about 5 ppm, about 10 ppm, about 15 ppm, about 20 ppm, about 25 ppm, about 30 ppm, about 35 ppm, or about 50 ppm up to, for example, about 35 ppm or about 50 ppm. In some embodiments, the flavor-grade compound, or the combination of flavor-grade compounds, is present at a concentration of more than 0.5 ppm. In some embodiments, the flavor-grade compound, or the combination of flavor-grade compounds, is present at a concentration of more than 1 ppm. In some embodiments, the flavor-grade compound, or the combination of flavor-grade compounds, is present at a concentration of more than 5 ppm. In some embodiments, the flavor-grade compound, or the combination of flavor-grade compounds, is present at a concentration of more than 10 ppm. In some embodiments, the flavor-grade compound, or the combination of flavor-grade compounds, is present at a concentration of more than 15 ppm. In some embodiments, the flavor-grade compound, or the combination of flavor-grade compounds, is present at a concentration of more than 20 ppm. In some embodiments, the flavor-grade compound, or the combination of flavor-grade compounds, is present at a concentration of more than 25 ppm. In some embodiments, the flavor-grade compound, or the combination of flavor-grade compounds, is present at a concentration of more than 30 ppm. In some embodiments, the flavor-grade compound, or the combination of flavor-grade compounds, is present at a concentration of more than 35 ppm. In some embodiments, the flavor-grade compound, or the combination of flavor-grade compounds, is present at a concentration of more than 50 ppm. In additional embodiments, the flavor-grade sweet taste modulator, or the combination of flavor-grade sweet taste modulators, of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) enhances the sweetness of a sweetener when the flavor-grade compound, or the combination of flavor-grade compounds, is present at a concentration less than about 50 ppm, about 35 ppm, about 30 ppm, about 25 ppm, about 20 ppm, about 15 ppm, about 10 ppm, about 5 ppm, about 1 ppm, or about 0.5 ppm. In some embodiments, the flavor-grade compound, or the combination of flavor-grade compounds, is present at a concentration less than 50 ppm. In some embodiments, the flavor-grade compound, or the combination of flavor-grade compounds, is present at a concentration less than 35 ppm. In some embodiments, the flavor-grade compound, or the combination of flavor-grade compounds, is present at a concentration less than 30 ppm. In some embodiments, the flavor-grade compound, or the combination of flavor-grade compounds, is present at a concentration less than 25 ppm. In some embodiments, the flavor-grade compound, or the combination of flavor-grade compounds, is present at a concentration less than 20 ppm. In some embodiments, the flavor-grade compound, or the combination of flavor-grade compounds, is present at a concentration less than 15 ppm. In some embodiments, the flavor-grade compound, or the combination of flavor-grade compounds, is present at a concentration less than 10 ppm. In some embodiments, the flavor-grade compound, or the combination of flavor-grade compounds, is present at a concentration less than 5 ppm. In some embodiments, the flavor-grade compound, or the combination of flavor-grade compounds, is present at a concentration less than 1 ppm. In some embodiments, the flavor-grade compound, or the combination of flavor-grade compounds, is present at a concentration less than 0.5 ppm. In yet additional embodiments, the flavor-grade sweet taste modulator, or the combination of flavor-grade sweet taste modulators, of the present disclosure enhances the sweetness of a sweetener when the flavor-grade compound, or the combination of flavor-grade compounds, is present at a concentration less than about 35 ppm, about 10 ppm, or about 1 ppm.

The terms "parts per million" and "ppm" are used in the food industry to refer to a low concentration of a solution. For example, one gram of solute in 1000 mL of solvent has a concentration of 1000 ppm and one thousandth of a gram (0.001 g) of solute in 1000 mL of solvent has a concentration of one ppm. Accordingly, a concentration of one milligram per liter (i.e., 1 mg/L) is equal to 1 ppm. A concentration of 1 mg % is 1 mg/100 mL. Accordingly, a concentration of 1 mg % is equal to 10 ppm.

The flavor-grade sweet taste modulators, or the combination of flavor-grade sweet taste modulators, of the disclosure may be combined with known naturally occurring and/or synthetic sweet taste modulators when used in embodiments (e.g., edible compositions and methods) described herein.

Sweeteners

In compositions and methods of the disclosure that comprise a sweetener, the sweetener can be of any type, for example a natural, non-natural, or synthetic sweetener. Non-limiting examples of such sweeteners include caloric carbohydrate sweeteners, natural carbohydrate sweeteners, non-natural carbohydrate sweeteners, natural high-potency sweeteners, non-natural high-potency sweeteners, synthetic high potency sweeteners, synthetic carbohydrate sweeteners, sugar alcohols, rare sugars and combinations thereof. In some embodiments, the at least one sweetener is chosen from caloric sweeteners. In another embodiment, the at least one sweetener is chosen from synthetic sweeteners. In another embodiment, the at least one sweetener is chosen from non-natural sweeteners. Non-limiting examples of rare sugars include D-Psicose, D-Turanose, D-allose, D-Tagatose, D-Sorbose, L-fructose, L-glucose, L-fructose, L-talose, L-ribose, and L-arabinose.

In some embodiments, the sweetener is a natural or inherent component of an edible composition. For example, the sweetener may be an inherent component of a food product or of a food stuff, such as fruit or a fruit product (e.g., fruit sauce). Accordingly, the flavor-grade compounds, or the combination of flavor-grade compounds, of the present disclosure may be used in edible compositions to which no sweetener is added.

The terms "caloric sweeteners" and "caloric carbohydrate sweeteners," are used interchangeably herein, and refer to nutritive sweeteners that provide calories and include all caloric carbohydrate sweeteners, such as sugars and polyols. Non-limiting examples of suitable caloric carbohydrate sweeteners include sucrose, fructose, glucose, erythritol, maltitol, lactitol, sorbitol, mannitol, xylitol, D-tagatose, trehalose, galactose, rhamnose, cyclodextrin (e.g., α-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, glucuronic acid, gluconic acid, glucono-lactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, nigero-oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42, or HFCS90), honey, maple syrup, coupling sugars, soybean oligosaccharides, and glucose syrup. Preferably, the sweetener is a natural sweetener chosen from glucose, fructose, sucrose, and mixtures thereof.

The term "polyol," as used herein, refers to a molecule that contains more than one hydroxyl group. A polyol may be a diol, triol, or a tetraol which contain 2, 3, and 4 hydroxyl groups, respectively. A polyol also may contain more than four hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the edible composition.

In some embodiments, the sweetener is a carbohydrate sweetener. In such embodiments, the sweetener is chosen from sucrose, fructose, glucose, erythritol, high fructose corn or starch syrup, and mixtures thereof.

The terms "synthetic high potency sweetener" and "artificial high potency sweetener" are used interchangeably herein and refer to any composition which is not found naturally in nature and characteristically has a sweetness potency greater than sucrose, fructose, or glucose, yet have fewer or no calories. Non-limiting examples of synthetic sweeteners suitable for embodiments of this disclosure include sucralose, acesulfame potassium or other salts, aspartame, alitame, saccharin, neohesperidin dihydrochalcone, cyclamate, neotame, advantame, and salts thereof.

In some embodiments, the sweetener is a synthetic sweetener. Preferably, the synthetic sweetener is chosen from sucralose, aspartame, potassium acesulfame, and mixtures thereof.

Other sweeteners suitable for use in embodiments provided herein, for example, include natural sweeteners. The terms "natural high-potency sweetener," "NHPS," "NHPS composition," and "natural high-potency sweetener composition" are used interchangeably, herein, and refer to any sweetener found in nature which may be in raw, extracted, purified, or any other form, singularly or in combination thereof and characteristically have a sweetness potency greater than sucrose, fructose, or glucose, yet have fewer or no calories. Non-limiting examples of NHPSs suitable for embodiments of this disclosure include steviol glycoside, rebaudioside A, rebaudioside B, rebaudioside C (dulcoside B), rebaudioside D, rebaudioside E, rebaudioside F, rebaudioside I, rebaudioside H, rebaudioside L, rebaudioside K, rebaudioside J, rebaudioside N, rebaudioside O, rebaudioside M, dulcoside A, rubusoside, stevia leaf extract, stevioside, glycosylated steviol glycosides, mogrosides, mogroside V, isomogroside, mogroside IV, Luo Han Guo fruit extract, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, or cyclocarioside I. In some embodiments, the glycosylated steviol glycoside is 13-[(2-O-β-D-glucopyranosyl-3-O-(4-O-α-D-glucopyranosyl)-β-D-glucopyranosyl-β-D-glucopyranosyl)oxy]ent-kaur-16-en-19-oic acid-[(4-O-α-D-glucopyranosyl-β-D-glucopyranosyl) ester], 13-[(2-O-β-D-glucopyranosyl-β-D-glucopyranosyl)oxy]ent-kaur-16-en-19-oic acid-[(4-O-(4-O-(4-O-α-D-glucopyranosyl)-α-D-glucopyranosyl)-α-D-glucopyranosyl)-β-D-glucopyranosyl ester], 13-[(2-O-β-D-glucopyranosyl-3-O-(4-O-(4-O-(4-O-α-D-glucopyranosyl)-α-D-glucopyranosyl)-α-D-glucopyranosyl)-β-D-glucopyranosyl-β-D-glucopyranosyl)oxy]ent-kaur-16-en-19-oic acid β-D-glucopyranosyl ester, or 13-[(2-O-β-D-glucopyranosyl-3-O-(4-O-(4-O-(4-O-α-D-glucopyranosyl)-α-D-glucopyranosyl)-α-D-glucopyranosyl)-β-D-glucopyranosyl-β-D-glucopyranosyl) oxy]ent-kaur-16-en-19-oic acid-[(4-O-α-D-glucopyranosyl-β-D-glucopyranosyl) ester]. NHPS also includes modified NHPSs. Modified NHPSs include NHPSs which have been altered naturally. For example, a modified NHPS includes, but is not limited to, NHPSs which have been fermented, contacted with enzyme, or derivatized or substituted on the NHPS. In one embodiment, at least one modified NHPS may be used in combination with at least one NHPS. In another embodiment, at least one modified NHPS may be used without a NHPS. Thus, modified NHPSs may be substituted for a NHPS or may be used in combination with NHPSs for any of the embodiments described herein. For the sake of brevity, however, in the description of embodiments, a modified NHPS is not expressly described as an alternative to an unmodified NHPS, but it should be understood that modified NHPSs can be substituted for NHPSs in any embodiment disclosed herein.

In some embodiments, the sweetener may be used individually or in combination with other sweeteners. For example, the sweetener composition may comprise a single caloric sweetener, a single NHPS or a single synthetic sweetener; a single caloric sweetener with a single NHPS; a single caloric sweetener with a single synthetic sweetener; one or more caloric sweetener with a single NHPS; one or more caloric sweetener with a single synthetic sweetener; a single caloric sweetener with one or more NHPS; a single caloric sweetener with one or more synthetic sweeteners; a single NHPS in combination with a single synthetic sweetener; one or more NHPSs in combination with a single synthetic sweetener; a single NHPS in combination with one or more synthetic sweeteners; one or more NHPSs in combination with one or more synthetic sweeteners; or one or more caloric sweetener with one or more NHPS and one or more synthetic sweetener. A plurality of natural and/or synthetic sweeteners may be used as long as the combined effect does not adversely affect the taste of the sweetener composition or orally sweetened composition.

One of ordinary skill in the art should appreciate that the sweetener composition can be customized to obtain a desired calorie content. For example, a low-caloric or non-caloric synthetic sweetener may be combined with a caloric sweetener and/or other caloric additives to produce a sweetener composition with a preferred calorie content.

The sweetener is present in the composition in an amount greater than its sweetness threshold level. In some embodiments, the sweetener is present in an amount ranging from 0.01% to 99.9% by weight, relative to the total weight of the composition. For example, the at least one sweetener is present in an amount ranging from 2% to 50%, or for example from 4% to 50% by weight, relative to the total weight of the composition. In some embodiments, the at least one sweetener is present in about 5% to about 20% by weight. In further embodiments, the at least one sweetener is present in about 5% to about 15% by weight. In yet further embodiments, the at least one sweetener is present in about 5% to about 12% by weight in beverages, for example, in non-alcoholic beverages.

In accordance with the disclosure, the flavor-grade sweet taste modulator, or the combination of flavor-grade sweet taste modulators, of the present disclosure potentiates or enhances the sweetness of the sweetener. The composition comprising the sweetener and the flavor-grade sweet taste modulator, or the combination of flavor-grade sweet taste modulators, of the present disclosure has more sweetness intensity than a composition comprising the at least one sweetener without the flavor-grade sweet taste modulator, or the combination of flavor-grade sweet taste modulators.

As used herein, the term "sweetness intensity" is understood to mean any perceptible sweetness. The composition comprising the sweetener and the flavor-grade sweet taste modulator, or the combination of flavor-grade sweet taste modulators, of the present disclosure is perceptibly sweeter than a composition comprising the sweetener without the flavor-grade sweet taste modulator, or the combination of flavor-grade sweet taste modulators. For example, a composition comprising the sweetener and the flavor-grade sweet taste modulator, or the combination of flavor-grade sweet taste modulators, of the present disclosure is slightly sweeter, moderately sweeter, or significantly sweeter than a composition comprising the sweetener without the flavor-grade sweet taste modulator, or the combination of flavor-grade sweet taste modulators. As discussed above, in embodiments where the flavor-grade sweet taste modulators of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds are used above their sweetness threshold, the increase in sweetness intensity is synergistic, not additive.

The sweetness of a composition may be based on (i.e., relative to) a known sweet standard. Sweet compounds based on such sweet standards include, but are not limited to, for example natural, non-natural, or synthetic sweeteners.

Non-limiting examples of such sweeteners include caloric carbohydrate sweeteners, natural carbohydrate sweeteners, non-natural carbohydrate sweeteners, natural high-potency sweeteners, non-natural high-potency sweeteners, synthetic high potency sweeteners, synthetic carbohydrate sweeteners, and combinations thereof. For example, the sweetness of a composition may be based on to a 5% sucrose solution. In such cases, a composition comprising the sweetener and a flavor-grade sweet taste modulator, or the combination of flavor-grade sweet taste modulators, of the present disclosure may be perceived as having a sweetness equivalent to a 5.5% sucrose solution. In other embodiments, the composition comprising the sweetener and a flavor-grade sweet taste modulator, or the combination of flavor-grade sweet taste modulators, of the present disclosure may be perceived as having a sweetness equivalent to a 6.0%, 6.5%, 7.0%, 7.5%, 8.0%, 8.5%, 9.0%, 9.5%, or 10% sucrose solution. Suitable sweet standards include, but are not limited to, sucrose standards, fructose standards and glucose standards. Each of these standards may be used at concentrations which include, but are not limited to, 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, or 10% solution. In some embodiments, the sweetness intensity of the composition comprising the sweetener and a flavor-grade sweet taste modulator, or the combination of flavor-grade sweet taste modulators, of the present disclosure increases the perceived sweetness based on a sweet standard by greater than 10%, by greater than 20%, by greater than 30%, by greater than 40%, greater than by 50% or greater than by 60% compared to a composition comprising the sweetener without the flavor-grade sweet taste modulator, or the combination of flavor-grade sweet taste modulators.

In some embodiments, the perception of sweetness intensity of the sweetener (i.e., the perception of sweet taste of the sweetener in the edible composition) is enhanced by up to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65°, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. In some embodiments, the perception of sweetness intensity of the sweetener is enhanced beyond 100%, for example, by 125%, 150%, 175%, 200%, 225%, 250%, 275%, 300%, 325%, 350%, 375%, 400%, 425%, 450%, 475%, 500% or increments in between those recited. In some embodiments, the perception of sweetness intensity is enhanced by up to 25%. In other embodiments, the perception of sweetness intensity is enhanced by up to 50%. In other embodiments, the perception of sweetness intensity is enhanced by up to 75%. In other embodiments, the sweetness intensity is enhanced by up to 100%. In some embodiments, the perception of sweetness intensity is enhanced by about 5%-about 100%, about 5%-about 90%, about 5%-about 80%, about 5%-about 70%, about 5%-about 60%, about 5%-about 50%, about 5%-about 40%, about 5%-about 30%, about 10%-about 30%, about 10%-about 25%. about 20%-about 80%, about 20%-about 70%, about 20%-about 60%, about 20%-about 50%, about 20%-about 40%, about 20%-about 30%, about 25%-about 80%, about 25%-about 70%, about 25%-about 60%, about 25%-about 50%, about 25%-about 40%, or about 25%-about 30%. These amounts are not meant to be limiting, and increments between the recited percentages are specifically envisioned as part of the disclosure.

It is contemplated that the combination of at least one sweetness enhancer and at least one sweetener may be carried out in any pH range that does not materially or adversely affect the taste of the sweetener composition or the sweetened composition. A non-limiting example of the pH range may be from about 1.5 to about 9.0. Further examples include a pH range from about 2.0 to about 8.5, from about 2.0 to about 8.0, from about 2.0 to about 7.5, from about 2.0 to about 7.0, from about 2.5 to about 7.0, and from about 3.0 to about 7.0. Additional examples of pH ranges include from about 2.0 to about 4.0, from about 2.5 to about 4.5, from about 3.5 to about 5.5, from about 5.0 to about 6.0, from about 4.0 to about 5.5, from about 5.0 to about 6.0, from about 6.5 to about 7.5, and from about 6.0 to about 8.0. In some embodiments, the pH is about 3.0 or about 7.0. The temperature of the composition may, for example, range from about −4° C. to about 90° C.

One of ordinary skill in the art may combine the sweetener(s) and flavor-grade sweet taste modulator(s), or the combination of flavor-grade sweet taste modulators, in any manner.

Sweet Taste Improving Compositions

The terms "sweet taste improving composition" and "sweet taste improving additive" are used interchangeably herein and refer to any material that imparts a more sugar-like temporal profile or sugar-like flavor profile or both to a synthetic sweetener. Suitable sweet taste improving additives useful in embodiments of this disclosure include amino acids and salts thereof, poly-amino acids and salts thereof, peptides, sugar acids and salts thereof, nucleotides and salts thereof, organic acids, inorganic acids, organic salts including organic acid salts and organic base salts, inorganic acid salts (e.g., sodium chloride, potassium chloride, magnesium chloride), acid salts (e.g., sodium citrate), bitter compounds, flavorants and flavoring ingredients, astringent compounds, polymers, proteins or protein hydrolysates, surfactants, emulsifiers, flavonoids, alcohols, and natural high-potency sweeteners.

The terms "sugar-like characteristic," "sugar-like taste," "sugar-like sweet," "sugary," and "sugar-like" are used interchangeably, herein, and include any characteristic similar to that of sucrose and include, but are not limited to, maximal response, flavor profile, temporal profile, adaptation behavior, mouth feel, concentration/response function behavior, tastant and flavor/sweet taste interactions, spatial pattern selectivity, and temperature effects. These characteristics are dimensions in which the taste of sucrose is different from the tastes of sweetness enhanced sweetener compositions. Suitable procedures for determining whether a composition has a more sugar-like taste are well known in the art.

The compositions of the present disclosure may also further comprise at least one additional additive, such as a sweet taste improving composition, and/or a sweet taste improving additive. For example, the composition of the disclosure may comprise at least one sweet taste improving composition for balancing the temporal and/or flavor profile of the sweetness enhanced sweetener composition. The use of sweet taste improving compositions to improve the temporal and/or flavor profile of sweetener compositions are described in detail in U.S. Patent Application Publication Nos. 2007/0128311, 2007/0275147, 2008/0292765, 2011/0160311, and US 2011/0318464 the disclosures of which are incorporated herein by reference in their entirety.

Exemplary suitable sweet-taste improving compounds include, but are not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, flavonoids, alcohols, polymers, other sweet taste improving taste additives imparting such sugar-like characteristics, and combinations thereof. In some embodiments, the sweet-taste improving compound is erythritol. In some such embodiments, the ratio of erythritol to flavor-grade Compound 1 is about 1:1 to about 800:1 by weight. In other embodiments, the ratio of erythritol to flavor-grade Compound 1 is about (30-200):1 or about (50-100): 1 by weight. In some such embodiments, the ratio of erythritol to flavor-grade Compound 2 is about 1:1 to about 800:1 by weight. In other embodiments, the ratio of erythritol to flavor-grade Compound 2 is about (30-200): 1 or about (50-100): 1 by weight. In some such embodiments, the ratio of erythritol to flavor-grade Compound 3 is about 1:1 to about 800:1 by weight. In other embodiments, the ratio of erythritol to flavor-grade Compound 3 is about (30-200): 1 or about (50-100): 1 by weight. In some such embodiments, the ratio of erythritol to flavor-grade Compound 4 is about 1:1 to about 800:1 by weight. In other embodiments, the ratio of erythritol to flavor-grade Compound 4 is about (30-200): 1 or about (50-100): 1 by weight. In some such embodiments, the ratio of erythritol to flavor-grade Compound 5 is about 1:1 to about 800:1 by weight. In other embodiments, the ratio of erythritol to flavor-grade Compound 5 is about (30-200): 1 or about (50-100):1 by weight. In some such embodiments, the ratio of erythritol to flavor-grade Compound 6 is about 1:1 to about 800:1 by weight. In other embodiments, the ratio of erythritol to flavor-grade Compound 6 is about (30-200): 1 or about (50-100):1 by weight. In some such embodiments, the ratio of erythritol to a combination of flavor-grade Compounds 1-6 is about 1:1 to about 800:1 by weight. In other embodiments, the ratio of erythritol to a combination of flavor-grade Compounds 1-6 is about (30-200):1 or about (50-100):1 by weight. In some such embodiments, the ratio of erythritol to a combination of flavor-grade Compounds 1 and 4 is about 1:1 to about 800:1 by weight. In other embodiments, the ratio of erythritol to a combination of flavor-grade Compounds 1 and 4 is about (30-200): 1 or about (50-100):1 by weight.

Suitable sweet taste improving amino acid additives for use in embodiments of this disclosure include, but are not limited to, aspartic acid, arginine, glycine, glutamic acid, proline, threonine, theanine, cysteine, cystine, alanine, valine, tyrosine, leucine, isoleucine, asparagine, serine, lysine, histidine, ornithine, methionine, carnitine, aminobutyric acid ($\alpha$-, $\beta$-, or $\gamma$-isomers), glutamine, hydroxyproline, taurine, norvaline, sarcosine, and their salt forms such as sodium or potassium salts or acid salts. The sweet taste improving amino acid additives also may be in the D- or L-configuration and in the mono-, di-, or tri-form of the same or different amino acids. Additionally, the amino acids may be $\alpha$-, $\beta$-, $\gamma$-, $\delta$-, and $\epsilon$-isomers if appropriate. Combinations of the foregoing amino acids and their corresponding salts (e.g., sodium, potassium, calcium, magnesium salts or other alkali or alkaline earth metal salts thereof, or acid salts) also are suitable sweet taste improving additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable sweet taste improving polyamino acid additives include poly-L-aspartic acid, poly-L-lysine (e.g., poly-L-$\alpha$-lysine or poly-L-$\epsilon$-lysine), poly-L-ornithine (e.g., poly-L-$\alpha$-ornithine or poly-L-$\epsilon$-ornithine), poly-L-arginine, other polymeric forms of amino acids, and salt forms thereof (e.g., calcium, potassium, sodium, or magnesium salts such as L-glutamic acid mono sodium salt). The sweet taste improving poly-amino acid additives also may be in the D- or L-configuration. Additionally, the poly-amino acids may be $\alpha$-, $\beta$-, $\gamma$-, $\delta$-, and $\epsilon$-isomers if appropriate. Combinations of the foregoing poly-amino acids and their corresponding salts (e.g., sodium, potassium, calcium, magnesium salts or other alkali or alkaline earth metal salts thereof or acid salts) also are suitable sweet taste improving additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to poly-amino acids of various molecular weights (MW), such as poly-L-$\alpha$-lysine with a MW of 1,500, MW of 6,000, MW of 25,200, MW of 63,000, MW of 83,000, or MW of 300,000. In some embodiments, the taste improving amino acid additive is glycine, alanine, taurine, serine or proline. In such embodiments, the taste improving amino acid additive is present in a concentration of about 10 ppm to about 25,000 ppm or about 100 ppm to about 1000 ppm.

Suitable sweet taste improving sugar acid additives include, for example, but are not limited to aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

For example, suitable sweet taste improving nucleotide additives include, but are not limited to, inosine monophosphate ("IMP"), guanosine monophosphate ("GMP"), adenosine monophosphate ("AMP"), cytosine monophosphate ("CMP"), uracil monophosphate ("UMP"), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

Suitable sweet taste improving organic acid additives include any compound which comprises a —COOH moiety. Suitable sweet taste improving organic acid additives, for example, include but are not limited to $C_2$-$C_{30}$ carboxylic acids, substituted hydroxyl $C_2$-$C_{30}$ carboxylic acids, benzoic acid, substituted benzoic acids (e.g., 2,4-dihydroxybenzoic acid), substituted cinnamic acids, hydroxyacids, substituted hydroxybenzoic acids, substituted cyclohexyl carboxylic acids, tannic acid, lactic acid, tartaric acid, citric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

For example, suitable sweet taste improving organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), and adipic acid. The examples of the sweet taste improving organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phospho, phosphonato, and any other viable functional group provided the substituted organic acid additives function to improve the sweet taste of a synthetic sweetener.

For example, suitable sweet taste improving inorganic acid additives include but are not limited to phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Suitable sweet taste improving bitter compound additives, for example, include but are not limited to caffeine, quinine, urea, bitter orange oil, naringin, quassia, and salts thereof.

Edible Compositions

According to one aspect, the disclosure provides an edible composition comprising a flavor-grade sweet taste modulator, or the combination of flavor-grade sweet taste modulators, of the disclosure for enhancing or potentiating the sweet taste of a sweetener or for masking or blocking a bitter or unpleasant taste. Thus, such edible compositions may comprise a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds. In some embodiments, the edible composition comprises a combination of flavor-grade Compounds 1-6, or comestibly or biologically acceptable salts or solvates thereof. In some embodiments, the edible composition comprises a combination of flavor-grade Compounds 1-3, or comestibly or biologically acceptable salts or solvates thereof. In some embodiments wherein the edible composition comprises a combination of flavor-grade Compounds 1-3, or comestibly or biologically acceptable salts or solvates thereof, the edible composition further comprises a combination of flavor-grade Compounds 4-6, or comestibly or biologically acceptable salts or solvates thereof. In some embodiments, the edible composition comprises a combination of flavor-grade Compounds 4-6, or comestibly or biologically acceptable salts or solvates thereof. In some embodiments, the edible composition comprises flavor-grade Compound 2, or a comestibly or biologically acceptable salt or solvate thereof. In some embodiments, the edible composition comprises a combination of flavor-grade Compounds 1 and 4, or comestibly or biologically acceptable salts, solvates, or enantiomers thereof. Optionally, the edible composition comprises a (i) sweetener; and (ii) a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds. In some embodiments, the edible composition comprises a sweetener and a combination of flavor-grade Compounds 1-6, or comestibly or biologically acceptable salts or solvates thereof. In some embodiments, the edible composition comprises a sweetener and a combination of flavor-grade Compounds 1-3, or comestibly or biologically acceptable salts or solvates thereof. In some embodiments, wherein the edible composition comprises a sweetener and a combination of flavor-grade Compounds 1-3, or comestibly or biologically acceptable salts or solvates thereof, the edible composition also comprises flavor-grade Compounds 4-6, or comestibly or biologically acceptable salts or solvates thereof. In some embodiments, the edible composition comprises a sweetener and a combination of flavor-grade Compounds 4-6, or comestibly or biologically acceptable salts or solvates thereof. In some embodiments, the edible composition comprises a sweetener and flavor-grade Compound 1, or a comestibly or biologically acceptable salt, solvate, or enantiomer thereof. In some embodiments, the edible composition comprises a sweetener and flavor-grade Compound 2, or a comestibly or biologically acceptable salt or solvate thereof. In some embodiments, the edible composition comprises a sweetener and flavor-grade Compound 3, or a comestibly or biologically acceptable salt or solvate thereof. In some embodiments, the edible composition comprises a sweetener and flavor-grade Compound 4, or a comestibly or biologically acceptable salt, solvate, or enantiomer thereof. In some embodiments, the edible composition comprises a sweetener and flavor-grade Compound 5, or a comestibly or biologically acceptable salt or solvate thereof. In some embodiments, the edible composition comprises a sweetener and flavor-grade Compound 6, or a comestibly or biologically acceptable salt or solvate thereof. In some embodiments, the edible composition comprises a sweetener and flavor-grade Compounds 1 and 4, or comestibly or biologically acceptable salts, solvates, or enantiomers thereof. In some embodiments, the edible composition comprises a sweetener and the crude from the reaction mixture from the method described above. In some embodiments, the crude from the reaction mixture comprises flavor-grade neoflavonoid compounds 1 and 4, or comestibly or biologically acceptable salts, enantiomers, or derivatives thereof.

The terms "edible composition," "orally ingestible composition" and "sweetenable composition" are used interchangeably, herein, and refer to a composition suitable for consumption, typically via the oral cavity (although consumption may occur via non-oral means such as inhalation). Edible compositions may be present in any form including, but not limited to, liquids, solids, semi-solids, tablets, lozenges, powders, gels, gums, pastes, slurries, syrups, aerosols and sprays. As used herein, edible compositions include food products, pharmaceutical compositions, and consumer products. The term edible composition also refers to, for example, dietary and nutritional supplements. As used herein, edible compositions also include compositions that are placed within the oral cavity but not swallowed, including professional dental products, such as dental treatments, fillings, packing materials, molds and polishes. The term "comestible" refers to similar compositions and is generally used as a synonym to the term "edible."

The term "food product" refers to any composition comprising one or more processed foodstuffs. Food products include, but are not limited to, confectionaries, bakery products (including, but not limited to, doughs, breads, biscuits, crackers, cakes, pastries, pies, tarts, quiches, and cookies), ice creams (including but not limited to impulse ice cream, take-home ice cream, frozen yogurt, gelato, sorbet, sherbet and soy, oat, bean and rice-based ice cream), dairy products (including, but not limited to, drinking milk, cheese, yogurt, and sour milk drinks), cheeses (including, but not limited to, natural cheeses and processed cheeses), butter, margarine, sweet and savory snacks (including but not limited to fruit snacks, chips/crisps, tortilla/corn chips, popcorn, pretzels, chocolates, and nuts), hot and cold beverages (including, but not limited to, beverages, beverage mixes, concentrates, juices, carbonated beverages, non-carbonated beverages, alcoholic beverages, non-alcoholic beverages, soft drinks, sports drinks, isotonic drinks, coffees, teas, bottled waters, and beverages prepared from botanicals and botanical extracts (including cold beverages that are prepared with botanical or fungi extracts as ingredients, and drinks that are prepared in various ways, such as infusions, decoctions, or other means of extraction or distillation of various plant parts, including, but not limited to leaves, flowers, stems, fruits, roots, rhizomes, stems, bark, volatile oils, or even the whole plant), snack bars (including, but not limited to granola bars, muesli bars, protein bars, breakfast bars, energy bars, and fruit bars), meal replacement products, ready meals (including, but not limited to canned meals, preserved meals, frozen meals, dried meals, chilled meals, dinner mixes, macaroni and cheese, frozen pizza, chilled pizza, and prepared salads), soups (including but not limited to broth-like soups and cream-based soups), broth, gravy, soy sauce, meats and fish (including raw, cooked, and dried meats), deli products (including but not limited to meats and cheeses suitable for slicing or pre-sliced meats and cheeses, e.g., turkey, chicken, ham, bologna, salami, bierwurst, capicola, chorizo, corned beef, Dutch loaf, Serrano, prosciutto, head cheese, liverwurst, meatloaf (including olive loaf, pepper loaf, pimento loaf, and ham and cheese loaf), mortadella, pastrami, pepperoni, roast beef, roast pork, saucisson, smoked meat, summer sausage, tongue, American cheese, blue cheese, cheddar cheese, Colby cheese, Colby-Jack cheese, gouda, Monterey Jack cheese, Muenster cheese mozzarella, Parmigiano cheese, pepper jack cheese, provolone, Romano cheese, string cheese, spray cheese, and Swiss cheese), vegetables (including, but not limited to, raw, pickled, cooked, and dried vegetables, such as French fries), fruits (including raw, cooked, and dried fruits), grains (including, but not limited to, dried cereals and breads), prepared foods (including, but not limited to, dried, canned, or jarred sauces and soups), snack foods, pastas (including, but not limited to, fresh pasta, chilled pasta, frozen pasta, dried pasta, and macaroni), noodles (including, but not limited to, egg noodles, wheat noodles, rice noodles, mung bean noodles, potato noodles, buckwheat noodles, corn noodles, cellophane noodles, chow mein, fettuccini, fusilli, gnocchi, lasagna, linguini, lo mein, macaroni, manicotti, pad thai, penne, ramen, rice vermicelli, rigatoni, soba, spaghetti, spatzle, udon, and ziti), canned foods, frozen foods, dried foods, chilled foods, oils and fats, baby food, spreads, salads, cereals (including, but not limited to, hot and cold cereals), sauces (including, but not limited to, cheese sauces (e.g., for macaroni and cheese) tomato pastes, tomato purees, bouillon cubes, stock cubes, table sauces, bouillabaisse sauces, pasta sauces, cooking sauces, marinades, dry sauces, powder mixes, ketchups, mayonnaises, salad dressings, vinaigrettes, mustards, and dips), jellies, jams, preserves, honey, puddings, recipe mixes, syrups, icings, fillings, infused foods, salt-preserved food, marinated foods and condiments (such as ketchup, mustard and steak sauce). In some embodiments, the food product is animal feed. For example, the food product may be a pet food product, i.e. a food product for consumption by a household pet. In other embodiments, the food product is a livestock food product, i.e. a food product for consumption by livestock.

The term "foodstuff" refers to an unprocessed ingredient or a basic nutrient or flavor containing element used to prepare a food product. Non-limiting examples of foodstuffs include: fruits, vegetables, meats, fishes, grains, milks, eggs, tubers, sugars, sweeteners, oils, herbs, snacks, sauces, spices and salts.

The term "processed foodstuff" refers to a foodstuff has been subjected to any process which alters its original state (excluding, e.g., harvesting, slaughtering, and cleaning). Examples of methods of processing foods include, but are not limited to, removal of unwanted outer layers, such as potato peeling or the skinning of peaches; chopping or slicing; mincing or macerating; liquefaction, such as to produce fruit juice; fermentation (e.g. beer); emulsification; cooking, such as boiling, broiling, frying, heating, steaming or grilling; deep frying; baking; mixing; addition of gas such as air entrainment for bread or gasification of soft drinks; proofing; seasoning (with, e.g., herbs, spices, salts); spray drying; pasteurization; packaging (e.g., canning or boxing); extrusion; puffing; blending; and preservation (e.g., adding salt, sugar, potassium lactate or other preservatives).

The term "consumer product" refers to health and beauty products for the personal use and/or consumption by a subject. Consumer products may be present in any form including, but not limited to, liquids, solids, semi-solids, tablets, capsules, lozenges, strips, powders, gels, gums, pastes, slurries, syrups, aerosols and sprays. Non-limiting examples of consumer products include nutriceuticals, nutritional supplements, lipsticks, lip balms, soaps, shampoos, gums, adhesives (e.g., dental adhesives), toothpastes, oral analgesics, breath fresheners, mouthwashes, tooth whiteners, and other dentifrices.

The edible composition may comprise (i) a flavor-grade sweet taste modulator of the disclosure, or combinations thereof; and (ii) a sweetener. In some embodiments, the flavor-grade sweet taste modulating compound, or the combination of flavor-grade sweet taste modulators, is a flavor-grade neoflavonoid compound having a molecular weight less than about 1000, about 500, or about 300 Daltons. In certain embodiments, the flavor-grade sweet taste modulating compound is a flavor-grade compound of Formula (I), or a comestibly or biologically acceptable salt, solvate or derivative thereof, or an enantiomer or diastereomer thereof, or a combination of any of the foregoing compounds. In other embodiments, the flavor-grade sweet taste modulating compound is any one of flavor-grade Compounds 1-6, or a comestibly or biologically acceptable salt, solvate, or derivative thereof; or a combination of any of the foregoing compounds. In other embodiments, the flavor-grade sweet taste modulating compound is any one of flavor-grade Compounds 1 or 4, or a comestibly or biologically acceptable salt, solvate, derivative, or enantiomer thereof. In other embodiments, the flavor-grade sweet taste modulating compound is any one of flavor-grade Compounds 2, 3, 5, and 6, or a comestibly or biologically acceptable salt, solvate or derivative thereof; or a combination of any of the foregoing compounds. In other embodiments, the flavor-grade sweet taste modulating compound is flavor-grade Compound 1, or a comestibly or biologically acceptable salt, solvate, derivative, or enantiomer thereof. In other embodiments, the flavor-grade sweet taste modulating compound is flavor-grade Compound 2, or a comestibly or biologically acceptable salt, solvate or derivative thereof. In other embodiments, the flavor-grade sweet taste modulating compound is flavor-grade Compound 3, or a comestibly or biologically acceptable salt, solvate or derivative thereof. In other embodiments, the flavor-grade sweet taste modulating compound is flavor-grade Compound 4, or a comestibly or biologically acceptable salt, solvate, derivative, or enantiomer thereof. In other embodiments, the flavor-grade sweet taste modulating compound is flavor-grade Compound 5, or a comestibly or biologically acceptable salt, solvate or derivative thereof. In other embodiments, the flavor-grade sweet taste modulating compound is flavor-grade Compound 6, or a comestibly or biologically acceptable salt, solvate or derivative thereof. In other embodiments, the flavor-grade sweet taste modulating compound is a combination of flavor-grade Compounds 1 and 4, or comestibly or biologically acceptable salts, solvates or derivatives thereof. In some embodiments, the flavor-grade sweet taste modulating compound is a combination of flavor-grade Compounds 1-3, or comestibly or biologically acceptable salts, solvates or derivatives thereof. In some embodiments wherein the flavor-grade sweet taste modulating compound is a combination of flavor-grade Compounds 1-3, or comestibly or biologically acceptable salts, solvates or derivatives thereof, the combination further comprises a combination of flavor-grade Compounds 4-6, or comestibly or biologically acceptable salts, solvates or derivatives thereof. In some embodiments, the flavor-grade sweet taste modulating compound is a combination of flavor-grade Compounds 4-6, or comestibly or biologically acceptable salts, solvates or derivatives thereof.

In some embodiments, the edible composition naturally or inherently comprises a sweetener. For example, the sweetener is an inherent component of a food product or of a food stuff, such as fruit or a fruit product (e.g., fruit sauce). Accordingly, the flavor-grade compounds, or the combination of flavor-grade compounds, of the present disclosure is added to edible compositions to which no sweetener is added.

In another embodiments, the edible composition is a sweetened composition comprising (i) a flavor-grade sweet taste modulator of the disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds); and (ii) a sweetener.

In some embodiments, the flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is used to enhance the sweet taste or perception of any suitable natural or synthetic sweetener, such as any suitable caloric, low-caloric or non-caloric sweetener. The flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, may have an inherent sweet taste and, in some embodiments, it is present at or above its sweetness threshold, but is not the primary sweetener in the composition. Rather, the flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, serves to enhance the sweet taste of the sweetener. The flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present at or below its sweetness threshold. In such cases, the flavor-grade compound, or the combination of flavor-grade compounds serves only to enhance the sweet taste of the sweetener. A person of skill in the art will be able to select the concentration of the flavor-grade sweet taste modulator, or the combination of flavor-grade modulators, so that it may impart the perception of enhanced sweetness to a composition comprising a sweetener. For example, a skilled artisan may select a concentration for the flavor-grade sweet taste modulator, or the combination of the flavor-grade sweet taste modulators, so that it does not impart any perceptible sweetness to a composition that does not comprise a sweetener. Non-limiting examples of such sweeteners include caloric carbohydrate sweeteners, natural carbohydrate sweeteners, non-natural carbohydrate sweeteners, natural high-potency sweeteners, non-natural high-potency sweeteners, synthetic high potency sweeteners, synthetic carbohydrate sweeteners, and combinations thereof.

In some embodiments, the edible composition further comprises a solubilizing agent, as discussed herein. Compounds—such as sweet taste modulators—have a particular solubility in aqueous solutions. As would be evident to one of skill in the art, the solubility of a compound depends on a number of factors including, but not limited to, the chemical structure of the compound, the solvent, the pH of the solvent, etc. Solubilizing agents may be used to increase the amount of a compound, such as a flavor-grade sweet taste modulator, or a combination of flavor-grade sweet taste modulators that may be dissolved in a particular amount of solvent.

Methods for solubilizing compounds of the present disclosure include but are not limited to chemical, physical or mechanical means. Additives, solubilizing or stabilizing agents may provide chemical means for increasing the concentration of flavor-grade compounds of the present disclosure in solution. Application of mechanical forces resulting in shearing, dispersion or emulsification of flavor-grade compounds of the present disclosure may also result in an increase in the concentration of flavor-grade compounds of the present disclosure in solution. Changes in temperature, pressure, and/or pH are non-limiting physical means for increasing the solubility of flavor-grade compounds of the present disclosure and/or maintaining the concentration of the flavor-grade compound in solution. The mechanical, physical or chemical means may be used in combination, in the presence or absence of cosolvents, surfactant systems, complexing agents and also including self-assembling nanomicelles, nanosuspensions, micronization and cocrystallizations. The methods as well as the importance of increasing the solubility of flavor-grade compounds in solution are well known in the art, for example, "Drug solubility: importance and enhancement techniques", ISRN Pharmaceutics, volume 2012, article ID 195727, Ketan T. Savjani, Anuradha K. Gajjar and Jignasa K. Savjani.

Solubilizing agents include, but are not limited to, glycoprotein-polysaccharides, such as Gum Arabic; homopolymers, such as poly(N-vinyl-pyrrolidone); medium chain mono- and diglycerides, such as Capmul MCM; oligosaccharides, such as Hp-beta-cyclodextrin, alpha-cyclodextrin, beta-cyclodextrin or gamma-cyclodextrin, and cellulose; polyglycerol esters, such as Caprol PEG 860®, Caprol 10G40® or Drewpol 10-1-CC®; polysorbates, such as Tween 20® (polysorbate 20), Tween 60® (polysorbate 60), and Tween 80® (polysorbate 80); and saponin/triterpene glycoside, such as quillaja saponin or Q-NATURALE®. For example, solubilizing agents include, but are not limited to, GRINDSTED® ACETEM, alpha-Cyclodextrin, beta-Cyclodextrin, DATEM, Decaglycerol dioleate, Decaglycerol monooleate, Decaglycerol monostearate, Ethoxylated monoglyceride, gamma-Cyclodextrin, Glycerol monoleate, Glycerol monostearate, Glyerol dioleate, Gum Arabic, Hexaglycerol dioleate, Hp-beta-Cyclodextrin, Lecithin, Methyl cellulose, Oleic acid, Poly(N-vinyl-pyrrolidone), Polyoxyethylene (20) sorbitan monooleate, Polyoxyethylene (20) sorbitan monopalmitate, Polyoxyethylene (20) sorbitan monostearate, Polyoxyethylene (20) sorbitan trioleate, Polyoxyethylene (20) sorbitan tristearate, Polysaccharides, polysorbate 20, polysorbate 60, polysorbate 80, Potassium oleate, Propylene glycol monostearate, Propylene glycol monolaurate, Quillaja saponins, Sodium lauryl sulfate, Sodium oleate, Sodium stearoyllactylate, Sorbitan monolaurate, Sorbitan trioleate, Sorbitan tristearate, Sorbitan monooleate, Sorbitan monostearate, Sucrose monoester, or Sucrose monolaurate. In some embodiments, the solubilizing agent is alpha-Cyclodextrin, beta-Cyclodextrin, gamma-Cyclodextrin, Gum Arabic, Hp-beta-Cyclodextrin, Lecithin, Methyl cellulose, Poly(N-vinyl-pyrrolidone), or Quillaja saponins (Q-NATURALE®). In some embodiments, the solubilizing agent is alpha-Cyclodextrin. In some embodiments, the solubilizing agent is beta-Cyclodextrin. In some embodiments, the solubilizing agent is gamma-Cyclodextrin. In some embodiments, the solubilizing agent is Gum Arabic. In some embodiments, the solubilizing agent is Hp-beta-Cyclodextrin. In some embodiments, the solubilizing agent is Lecithin. In some embodiments, the solubilizing agent is Methyl cellulose. In some embodiments, the solubilizing agent is Poly(N-vinyl-pyrrolidone). In some embodiments, the solubilizing agent is Quillaja saponins. Solubilizing agents may be used at concentrations between 0.001% to 50% to solubilize the flavor-grade compounds of the disclosure. In some embodiments, concentrations of solubilizing agents in the final product range from about 0.05% to about 2%.

Solvents for dissolving the flavor-grade sweet taste modulator of the combination of flavor-grade sweet taste modulators of the disclosure include, but are not limited to, 1,3-butylene glycol, amyl acetate, benzyl alcohol, butane-1,3-diol, castor oil, diethyl tartrate, diethylene glycol monoethyl ether, ethyl acetate, ethyl alcohol, glycerin, glycerol, glycerol diacetate, isopropyl alcohol, NEOBEE® M-5 oil, propylene glycol, and triacetin. In some embodiments, the solvent is 1,3-butylene glycol. In some embodiments, the solvent is amyl acetate. In some embodiments, the solvent is benzyl alcohol. In some embodiments, the solvent is butane-1,3-diol. In some embodiments, the solvent is castor oil. In some embodiments, the solvent is diethyl tartrate. In some embodiments, the solvent is diethylene glycol monoethyl ether. In some embodiments, the solvent is ethyl acetate. In some embodiments, the solvent is ethyl alcohol. In some embodiments, the solvent is glycerin. In some embodiments, the solvent is glycerol. In some embodiments, the solvent is glycerol diacetate. In some embodiments, the solvent is isopropyl alcohol. In some embodiments, the solvent is propylene glycol. In some embodiments, the solvent is triacetin. Solvents may be used at concentrations between 0.001% to 50% to solubilize the flavor-grade compounds of the disclosure. In some embodiments, solvent concentrations in the final product range from about 0.05 to about 2%.

In some embodiments, the edible composition further comprises a surfactant to increase or decrease the effectiveness of the flavor-grade compounds, or the combination of flavor-grade compounds, of the present disclosure as sweet taste modulators. Suitable surfactants include, but are not limited to, non-ionic surfactants (e.g., mono and diglycerides, fatty acid esters, sorbitan esters, propylene glycol esters, and lactylate esters) anionic surfactants (e.g., sulfosuccinates and lecithin) and cationic surfactants (e.g., quaternary ammonium salts).

The rate of release of the flavor-grade sweet taste modulator, or the combination of flavor-grade sweet taste modulators, of the present disclosure may be regulated. The release rate of the flavor-grade sweet taste modulator, or the combination of flavor-grade sweet taste modulators, of the present disclosure can be altered by, for example, varying its solubility in water. Rapid release can be achieved by encapsulating the flavor-grade sweet taste modulator, or the combination of flavor-grade sweet taste modulators, of the present disclosure with a material with high water solubility. Delayed release of the flavor-grade sweet taste modulator, or the combination of flavor-grade sweet taste modulators, of the present disclosure can be achieved by encapsulating the flavor-grade sweet taste modulator, or the combination of flavor-grade sweet taste modulators, of the present disclosure with a material with low water solubility. The flavor-grade sweet taste modulator, or the combination of flavor-grade sweet taste modulators, of the present disclosure can be co-encapsulated with carbohydrates or masking tastants such as sweeteners. The rate of release of the flavor-grade sweet taste modulator, or the combination of flavor-grade sweet taste modulators, of the present disclosure can also be regulated by the degree of encapsulation. In some embodiments, the flavor-grade sweet taste modulator, or the combination of flavor-grade sweet taste modulators, of the present disclosure is fully encapsulated. In other embodiments, the flavor-grade compounds, or the combination of flavor-grade compounds, of the present disclosure are partially encapsulated. In some embodiments, the rate of release may be regulated so as to release with the flavor-grade sweet taste modulator, or the combination of flavor-grade sweet taste modulators. In some embodiments, the rate of release may be regulated in a manner that is dependent on the structure of the sweetener and flavor-grade sweet taste modulator, or the combination of flavor-grade sweet taste modulators.

The edible compositions of this disclosure are prepared according to techniques well-known in the art. In general, an edible composition of the disclosure is prepared by mixing a component or ingredient of the edible composition, such as a sweetener, with a flavor-grade sweet taste modulating compound, or a combination of the flavor-grade sweet taste modulating compounds, of the disclosure. Alternatively, a flavor-grade sweet taste modulating compound, or a combination of the flavor-grade sweet taste modulating compounds, of the disclosure can be added directly to the edible composition comprising a sweetener. In some embodiments, a sweetener is added simultaneously or sequentially with a flavor-grade sweet taste modulating compound, or a combination of the flavor-grade sweet taste modulating compounds, of the disclosure. If sequentially, the sweetener may be added before or after the flavor-grade sweet taste modulating compound, or the combination of flavor-grade sweet taste modulating compounds, of the disclosure. In some embodiments, the edible composition is a food product. In some embodiments, the edible composition is a pharmaceutical composition. In some embodiments, the edible composition is a consumer product. In some embodiments, the edible composition is in the form of, for example, a gum, lozenge, sauce, condiment, meat matrix, meat slurry, paste, suspension, spread, coating, a liquid, a gel, an emulsion, granules, or seasoning.

The amount of both a flavor-grade sweet taste modulating compound, or a combination of the flavor-grade sweet taste modulating compounds, of the present disclosure and a sweetener used in an edible composition depends upon a variety of factors, including the purpose of the composition and the desired or acceptable perception of sweetness. The amount may depend on the nature of the edible composition, the particular flavor-grade compound, or the combination of flavor-grade sweet taste modulating compounds, added, the sweetener, other compounds present in the composition, the method of preparation (including amount of heat used), and the pH of the edible composition. Those of skill in the art will know how to determine the amounts needed to produce the desired taste(s).

When the edible compositions are formulated for ingestion via the oral cavity, a flavor-grade sweet taste modulating compound, or a combination of flavor-grade sweet taste modulating compounds, of the disclosure may be present at any of the concentrations effective for modulating the sweetness of a sweetener listed above.

In some embodiments, the edible compositions are formulated as a concentrate, which is intended for dilution prior to consumption. Such concentrates include syrups, frozen concentrates, dry mixes, and food additives. When present in a concentrate, the sweet taste modulating, flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, is present at a concentration about 2-fold, about 3-fold, about 4-fold, about 5-fold, about 6-fold, about 7-fold, about 8-fold, about 9-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 150-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, or about 1000-fold above any of the effective concentrations discussed herein. Accordingly, the flavor-grade sweet taste modulating compounds, or the combination of the flavor-grade sweet taste modulating compounds, may be present in a concentrate—for later dilution—at concentration between about 1 ppm and about 5000 ppm. In some embodiments, the flavor-grade sweet taste modulator, or the combination of flavor-grade sweet taste modulators, of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) may be present in a concentrate at a concentration between about 1 ppm to about 3000 ppm; about 10 ppm to about 1000 ppm; about 50 ppm to about 500 ppm; about 50 ppm to about 250 ppm; about 50 ppm to about 100 ppm; about 100 ppm to about 500 ppm; about 100 ppm to about 1000 ppm; about 100 ppm to about 3000 ppm; about 500 ppm to about 1000 ppm; about 500 ppm to about 3000 ppm; or about 1000 ppm to about 3000 ppm. In yet other embodiments, the flavor-grade sweet taste modulator of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) may be present in a concentrate for dilution at a concentration of about 50 ppm to about 3000 ppm, about 50 ppm to about 1000 ppm or about 50 ppm to about 500 ppm. In additional embodiments, the flavor-grade sweet taste modulator of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) may be present in a concentrate for dilution at a concentration of about 1 ppm to about 500 ppm; about 1 ppm to about 250 ppm; about 1 ppm to about 100 ppm; about 1 ppm to about 50 ppm; about 10 ppm to about 500 ppm; about 10 ppm to about 250 ppm; about 10 ppm to about 100 ppm; about 50 ppm to about 500 ppm; about 50 ppm to about 250 ppm; or about 50 ppm to about 100 ppm.

The flavor-grade sweet taste modulator, or the combination of flavor-grade sweet taste modulators, of the present disclosure (e.g., a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds) may be present in a concentrate for dilution at a concentration of about 50 ppm, about 75 ppm, about 100 ppm, about 150 ppm, about 200 ppm, about 250 ppm, about 300 ppm, about 350 ppm, about 400 ppm, about 450 ppm, about 500 ppm, about 550 ppm, about 600 ppm, about 650 ppm, about 700 ppm, about 750 ppm, about 800 ppm, about 850 ppm, about 900 ppm, about 950 ppm, about 1000 ppm, about 1050 ppm, about 1100 ppm, about 1150 ppm, about 1200 ppm, about 1250 ppm, about 1300 ppm, about 1350 ppm, about 1400 ppm, about 1450 ppm, about 1500 ppm, about 1550 ppm, about 1600 ppm, about 1650 ppm, about 1700 ppm, about 1750 ppm, about 1800 ppm, about 1850 ppm, about 1900 ppm, about 1950 ppm, about 2000 ppm, about 2050 ppm, about 2100 ppm, about 2150 ppm, about 2200 ppm, about 2250 ppm, about 2300 ppm, about 2350 ppm, about 2400 ppm, about 2450 ppm, about 2500 ppm, about 2550 ppm, about 2600 ppm, about 2650 ppm, about 2700 ppm, about 2750 ppm, about 2800 ppm, about 2850 ppm, about 2900 ppm, about 2950 ppm, or about 3000 ppm.

In some embodiments, the edible composition further comprises a sweet taste improving composition.

The edible compositions may be included in a package. Optionally, the edible composition is packaged in bulk, in which the package contains more of the compositions than would typically be used for a single dish or serving of food or beverage. Such bulk packages can be in the form of paper, plastic, or cloth bags or cardboard boxes or drums. Such bulk packages may be fitted with plastic or metal spouts to facilitate the dispensing of the edible composition.

The package may contain an edible composition comprising a flavor-grade sweet taste modulating compound, or a combination of flavor-grade sweet taste modulating compounds, of the present disclosure and a sweetener. In some embodiments, the package contains an edible composition comprising a flavor-grade sweet taste modulating compound, or a combination of flavor-grade sweet taste modulating compounds, of the present disclosure and caloric carbohydrate sweetener. In some embodiments, the package contains an edible composition comprising a flavor-grade sweet taste modulating compound, or a combination of flavor-grade sweet taste modulating compounds, of the present disclosure and glucose, fructose, sucrose, or a mixture thereof. In some embodiments, the package contains an edible composition comprising a flavor-grade sweet taste modulating compound, or a combination of flavor-grade sweet taste modulating compounds, of the present disclosure and a synthetic sweetener. In some embodiments, the package contains an edible composition comprising a flavor-grade sweet taste modulating compound, or a combination of flavor-grade sweet taste modulating compounds, of the present disclosure and a natural high-potency sweetener.

The edible compositions may be used for medicinal or hygienic purposes, for example, in mouthwash, medicines, pharmaceuticals, cough syrup, throat spray, toothpaste, dental adhesives, tooth whiteners, glues (e.g., on stamps and envelopes), and toxins used in insect and rodent control.

In some embodiments of the disclosure, the sweetener composition is in a form of a tabletop sweetener composition comprising at least one flavor-grade sweet taste modulator according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, at least one sweetener, at least one bulking agent, and optionally at least one sweet taste improving composition and/or anti-caking agent with improved temporal and/or flavor profile.

For example, suitable "bulking agents" include, but are not limited to maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and mixtures thereof. Additionally, the at least one bulking agent is chosen from, granulated sugar (sucrose) or other caloric sweeteners such as crystalline fructose, other carbohydrates, and sugar alcohols. In one embodiment, a bulking agent may be used as a sweet taste improving composition.

As used herein the phrase "anti-caking agent" is understood to mean any composition which prevents, reduces, inhibits, or suppresses at least one sweetener molecule from attaching, binding, or contacting to another sweetener molecule. Alternatively, "anti-caking agent" may refer to any composition which assists in content uniformity and uniform dissolution. In accordance with some embodiments, non-limiting examples of anti-caking agents include cream of tartar, calcium silicate, silicon dioxide, microcrystalline cellulose (Avicel, FMC BioPolymer, Philadelphia, Pa.), and tricalcium phosphate. In at least one embodiment, the anti-caking agents are present in the tabletop sweetener composition in an amount from about 0.001% to about 3% by weight of the tabletop sweetener composition.

Tabletop sweetener compositions may be embodied and packaged in numerous different forms, and may be of any form known in the art. For example, and not by way of limitation, the tabletop sweetener compositions may be in the form of powders, granules, packets, tablets, sachets, pellets, cubes, solids, or liquids.

Method of Preparing an Edible Composition

According to another aspect, the disclosure provides a method of preparing an edible composition. The method comprises: (a) providing a sweetener; and (b) adding to the sweetener of (a) a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds. In some embodiments, the flavor-grade sweet taste modulator of the disclosure has been solubilized prior to the addition step (b). In other embodiments, a solubilizing agent is added to the composition. In some embodiments, the sweetener of step (a) is provided in a comestibly acceptable carrier. The skilled artisan will appreciate that method steps (a) and (b) can be performed in any order—i.e., the method may comprise: (a) adding a flavor-grade compound of Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds; and (b) adding a sweetener to the Compound(s) of (a).

In general, the method of preparing an edible composition of the disclosure comprises mixing a component or ingredient of the edible composition, such as a sweetener, with a flavor-grade sweet taste modulating compound, or a combination of flavor-grade sweet taste modulating compounds, of the disclosure. Alternatively, a flavor-grade sweet taste modulating compound, or a combination of flavor-grade sweet taste modulating compounds, of the disclosure can be added directly to the edible composition comprising a sweetener. In some embodiments, the sweetener is added to the edible composition simultaneously or sequentially with a flavor-grade sweet taste modulating compound, or a combination of flavor-grade sweet taste modulating compounds, of the disclosure. If sequentially, the sweetener may be added before or after the flavor-grade sweet taste modulating compound, or the combination of flavor-grade sweet taste modulating compounds, of the disclosure. When solubilizing agents are utilized, the method includes the addition of the solubilizing agent at any point. For example, if the composition compromises three components—the sweetener, the flavor-grade sweet taste modulating agent, or the combination of flavor-grade sweet taste modulating agents, and the solubilizing compound—the solubilizing compound may be added as the first, second, or third component. The solubilizing agent may also be added concurrently with any other component.

In some embodiments, the methods of preparing an edible composition further comprise adding at least one additional additive, such as a sweet taste improving composition, and/or a sweet taste improving additive.

The edible compositions may be a food product, a pharmaceutical composition, or a consumer product. In some embodiments, the edible composition is in the form of, for example, a gum, lozenge, sauce, condiment, meat matrix, meat slurry, paste, suspension, spread, coating, a liquid, a gel, an emulsion, granules, or seasoning.

Method of Enhancing or Potentiating the Perception of Sweet Taste

According to another aspect, the disclosure provides a method of enhancing the perception of sweet taste in a subject. The method comprises the use of an edible composition of the present disclosure, where the edible composition comprises a flavor-grade compound according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds. Optionally, the edible composition comprises (i) a flavor-grade compound according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds; (ii) a sweetener; and optionally (iii) a solubilizing agent.

The terms "perception of a sweet taste," "perception of sweetness," "perception of a flavor" and similar terms, refer to the awareness of a subject of a particular taste or flavor.

The term "subject" refers to a mammal. In preferred embodiments, the subject is human. In some embodiments, a subject is a domestic or laboratory animal, including but not limited to, household pets, such as dogs, cats, pigs, rabbits, rats, mice, gerbils, hamsters, guinea pigs, and ferrets. In some embodiments, a subject is a livestock animal. Non-limiting examples of livestock animals include: alpaca, bison, camel, cattle, deer, pigs, horses, llamas, mules, donkeys, sheep, goats, rabbits, reindeer, and yak.

The method can be used to enhance or potentiate sweet taste in any edible composition, including a foodstuff, food product, pharmaceutical composition or consumer product. The edible composition may be in any form. In some embodiments, the composition is in the form of, for example, a gum, lozenge, sauce, condiment, paste, suspension, spread, coating, a liquid, a gel, an emulsion, granules, or seasoning.

The edible composition may be utilized by, for example, placement in the oral cavity or by ingestion. In some embodiments, the edible composition comprising a flavor-grade sweet taste modulator, or a combination of flavor-grade sweet taste modulators, of the disclosure is placed in the oral cavity or ingested before an edible composition, such as a foodstuff, a food product, pharmaceutical composition or consumer product, comprising a sweetener, while in other embodiments, the edible composition comprising a flavor-grade sweet taste modulator, or a combination of flavor-grade sweet taste modulators, of the disclosure is placed in the oral cavity or ingested after a sweet food stuff, food product, pharmaceutical composition or consumer product. In other embodiments, the edible composition comprising a flavor-grade sweet taste modulator, or a combination of flavor-grade sweet taste modulators, of the disclosure is placed in the oral cavity or ingested concurrently with a sweet food stuff, food product, pharmaceutical composition or consumer product, either as a separate edible composition or by incorporation in the sweet food stuff, food product, pharmaceutical composition or consumer product. For example, a flavor-grade sweet taste modulator, or a combination of flavor-grade sweet taste modulators, of the disclosure can be combined with foodstuffs or food products to enhance or potentiate the sweet taste of a foodstuff or food product. Alternatively, a flavor-grade sweet taste modulator, or a combination of flavor-grade sweet taste modulators, of the disclosure can be used, for example, in a lozenge or gum for use after exposure to a sweet food stuff, food product, pharmaceutical composition or consumer product (e.g., to enhance or potentiate a sweet aftertaste).

Method of Reducing the Amount of a Sweetener in an Edible Composition

It may be desirable to reduce the amount of a caloric sweetener in an edible composition to reduce the calorie content of that edible composition. It may also be desirable to decrease the amount of a synthetic sweetener or a non-natural high potency sweetener in an edible composition to decrease an undesirable taste or aftertaste associated with the synthetic sweetener or non-natural high potency sweetener. Accordingly, another aspect of the present disclosure provides a method of reducing the amount of a sweetener in an edible composition, such as a food product, a pharmaceutical composition or a consumer product. An amount of the sweetener in the edible composition may be replaced with a flavor-grade sweet taste modulator according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds. In such methods, an amount of solubilizing agent may also be added to the edible composition, as described herein.

The term "replace" or "replacing" refers to substituting one compound for another compound in or in the preparation of, for example, an edible composition, such as food product. It includes complete and partial replacements or substitutions.

In some embodiments, the method comprises: (a) replacing an amount of a sweetener used in preparing an edible composition with an amount of a flavor-grade sweet taste modulator according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds. In some embodiments, the flavor-grade sweet taste modulating compound, or the combination of flavor-grade sweet taste modulating compounds, of the disclosure is added in the form of an edible composition comprising the flavor-grade sweet taste modulator, or a combination of flavor-grade sweet taste modulators, of the disclosure. In such methods, an amount of solubilizing agent may also be added to the edible composition, as described herein.

In some embodiments, the method of reducing the amount of a sweetener in an edible composition comprises the steps of: (a) ingesting a first edible composition, in which the amount of a sweetener has been reduced; and (b) ingesting a second edible compound, which comprises a flavor-grade sweet taste modulator compound, or a combination of flavor-grade sweet taste modulating compounds, of the present disclosure. In some embodiments, the first edible composition is ingested before the second edible composition. In some embodiments, the first edible composition is ingested after the second edible composition. In some embodiments, the first edible composition is ingested concurrently with the second edible composition. In such methods, an amount of solubilizing agent may also be added along with the flavor-grade sweet taste modulator, or a combination of flavor-grade sweet taste modulators, of the present disclosure.

In some embodiments, the edible composition is a food product. In some embodiments, the edible composition is a pharmaceutical composition. In some embodiments, the edible composition is a consumer product. The sweetener being replaced may be a natural caloric sweetener, a natural high-potency sweetener, a synthetic sweetener, or combinations thereof. When the sweetener being replaced is a natural caloric sweetener, the sweetener may be sucrose, fructose, glucose, erythritol, high fructose corn/starch syrup, and mixtures thereof. When the sweetener being replaced is a synthetic sweetener, the sweetener may be sucralose, aspartame, potassium acesulfame, and mixtures thereof. The method also comprises replacing an amount of a natural caloric sweetener with a synthetic or natural high-potency sweetener and a flavor-grade sweet taste modulating compound, or a combination of flavor-grade sweet taste modulating compounds, of the present disclosure, such that any off-taste or after taste associated with the synthetic or natural high-potency sweetener is reduced or eliminated. In such embodiments, the "sweetener replaced" is the natural caloric sweetener.

In some embodiments, the methods of reducing sugar intake of a subject further comprise the step of identifying a subject in need thereof. The skilled worker would be able to identify a subject in need of reducing sugar intake. Non-limiting examples of such subjects include subjects that suffer from any one or more of the following disorders: diabetes, pre-diabetes, insulin resistance, obesity, excessive weight, and hyperglycemia.

In some embodiments, the amount of the sweetener replaced in the edible composition in step (a) is an amount sufficient to maintain or restore the health of a subject. For example, the amount of the sweetener replaced in the edible composition may be an amount sufficient to decrease diabetes, pre-diabetes, insulin resistance, obesity, excessive weight, and hyperglycemia in a subject. The amount of the sweetener replaced may be up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 99%. These amounts are not meant to be limiting, and increments between the recited percentages are specifically envisioned as part of the disclosure.

In some embodiments, the amount of the flavor-grade sweet taste modulating compound, or the combination of flavor-grade sweet taste modulating compounds, added in step (b) is effective to enhance the perception of sweet taste in the subject.

In some embodiments, the amount of the flavor-grade sweet taste modulating compound, or the combination of flavor-grade sweet taste modulating compounds, added in step (b) is sufficient to permit replacement of up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 99% of the amount of sweetener present in the edible composition. These amounts are not meant to be limiting, and increments between the recited percentages are specifically envisioned as part of the disclosure. In some embodiments, the amount of the flavor-grade sweet taste modulating compound, or the combination of flavor-grade sweet taste modulating compounds, added in step (b) is sufficient to permit replacement of up to 25% of the amount of the sweetener present in the edible composition. In other embodiments, the amount of the flavor-grade sweet taste modulating compound, or the combination of flavor-grade sweet taste modulating compounds, added in step (b) is sufficient to permit replacement of up to 50% of the amount of the sweetener present in the edible composition. In other embodiments, the amount of the flavor-grade sweet taste modulating compound, or the combination of flavor-grade sweet taste modulating compounds, added in step (b) is sufficient to permit replacement of up to 75% of the amount of the sweetener present in the edible composition. In yet other embodiments, the amount of the flavor-grade sweet taste modulating compound, or the combination of flavor-grade sweet taste modulating compounds, added in step (b) is sufficient to permit replacement of up to 99% of the amount of the sweetener present in the edible composition.

In some embodiments, the method of reducing the amount of a sweetener in an edible composition further comprises adding at least one additional additive, such as a sweet taste improving composition, and/or a sweet taste improving additive.

Method of Reducing Caloric Intake

Another aspect of the disclosure provides a method of reducing caloric intake of a subject. In some embodiments, the method comprises the step of providing an edible composition to the subject, wherein all or a portion of a natural caloric sweetener in the edible composition is replaced with (a) a flavor-grade sweet taste modulating compound according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds; or (b) one or more synthetic or natural high potency sweeteners and a flavor-grade sweet taste modulating compound according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds. The edible composition may be a food product, a pharmaceutical composition, or a consumer product. In such methods, an amount of solubilizing agent may also be added to the edible composition, as described herein.

The methods of reducing caloric intake of a subject may further comprise the step of identifying a subject in need thereof. The skilled worker would be able to identify a subject in need of reducing sugar intake. Non-limiting examples of such subjects include subjects that suffer from any one or more of the following disorders: diabetes, pre-diabetes, insulin resistance, obesity, excessive weight, and hyperglycemia.

In some embodiments, the amount of the natural caloric sweetener replaced in the edible composition is an amount sufficient to maintain or restore the health of a subject. For example, the amount of the natural caloric sweetener replaced in the edible composition may be an amount sufficient to result in weight loss in a subject. Alternatively, the amount of the natural caloric sweetener replaced in the edible composition may be an amount sufficient to alleviate the effects of, or treat, a disease associated with sugar consumption or excessive weight of the subject (e.g., diabetes). In some embodiments, the amount of the natural caloric sweetener replaced in the edible composition is up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 99%. These amounts are not meant to be limiting, and increments between the recited percentages are specifically envisioned as part of the disclosure. In some embodiments, the present method results in the subject's daily natural caloric sweetener intake being less than 250 g/day, less than 200 g/day, less than 175 g/day, less than 150 g/day, less than 125 g/day, less than 100 g/day, less than 75 g/day, less than 50 g/day, less than 25 g/day, less than 20 g/day, less than 15 g/day, less than 10 g/day, or less than 25 g/day.

In some embodiments, the amount of flavor-grade sweet taste modulating compound, or the combination of flavor-grade sweet taste modulating compounds, of the disclosure added to the edible composition is sufficient to permit reduction of a subject's natural caloric sweetener intake by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 99%. These amounts are not meant to be limiting, and increments between the recited percentages are specifically envisioned as part of the disclosure. In some embodiments, the amount of flavor-grade sweet taste modulating compound, or the combination of flavor-grade sweet taste modulating compounds, of the disclosure added to the edible composition is sufficient to permit reduction of a subject's natural caloric sweetener intake by up to 25%. In other embodiments, the amount of flavor-grade sweet taste modulating compound, or the combination of flavor-grade sweet taste modulating compounds, of the disclosure added to the edible composition is sufficient to permit reduction of a subject's natural caloric sweetener intake by up to 50%. In other embodiments, the amount of flavor-grade sweet taste modulating compound, or the combination of flavor-grade sweet taste modulating compounds, of the disclosure added to the edible composition is sufficient to permit reduction of a subject's natural caloric sweetener intake by up to 75%. In yet other embodiments, the amount of flavor-grade sweet taste modulating compound, or the combination of flavor-grade sweet taste modulating compounds, of the disclosure added to the edible composition is sufficient to permit reduction of a subject's natural caloric sweetener intake by up to 99%.

In some embodiments, the method of reducing the amount of a sweetener in an edible composition further comprises adding at least one additional additive, such as a sweet taste improving composition, and/or a sweet taste improving additive.

Method of Enhancing Sweet Taste of an Edible Composition

According to another embodiment, the disclosure provides methods of enhancing or potentiating the sweet taste in an edible composition. The edible composition may be a food product, a pharmaceutical composition, or a consumer product.

In one embodiment, the method comprises: (a) adding an effective amount of a flavor-grade sweet taste modulating compound according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, to an edible composition comprising a sweetener such that the perception of sweetness intensity of the sweetener is enhanced. In some embodiments, the sweetener is either added to the edible composition before the flavor-grade sweet taste modulating compound, or the combination of flavor-grade sweet taste modulating compounds; concurrently with the flavor-grade sweet taste modulating compound, or the combination of flavor-grade sweet taste modulating compounds; or after the flavor-grade sweet taste modulating compound, or the combination of flavor-grade sweet taste modulating compounds. In other embodiments, the sweetener is naturally or inherently present in the edible composition when the flavor-grade sweet taste modulating compound, or the combination of flavor-grade sweet taste modulating compounds, is added. In such methods, an amount of solubilizing agent may also be added to the edible composition, as described herein.

Alternatively, the method comprises: (a) ingesting an effective amount of a flavor-grade sweet taste modulating compound according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, before, along with, or after the edible composition such that the perception of sweetness intensity of the sweetener is enhanced. In such methods, an amount of solubilizing agent may also be added to the edible composition, as described herein.

The edible composition may comprise a sweetener, such as a natural caloric sweetener, a natural high-potency sweetener, a synthetic sweetener, or combinations thereof. When the sweetener is a natural caloric sweetener, the sweetener may be sucrose, fructose, glucose, erythritol, high fructose corn/starch syrup, and mixtures thereof. When the sweetener is a synthetic sweetener, the sweetener may be sucralose, aspartame, potassium acesulfame, and mixtures thereof.

In some embodiments, the perception of sweetness intensity of the sweetener is enhanced by up to 1%, 2%, 3%, 4%, 5%, 6%, 7%, 8%, 9%, 10%, 15%, 20%, 25%, 30%, 35%, 40%, 45%, 50%, 55%, 60%, 65%, 70% 75%, 80%, 85%, 90%, 95% or 100%. In some embodiments, the perception of sweetness intensity of the sweetener is enhanced beyond 100%, for example, by 125%, 150%, 175%, 200%, 225%, 250%, 275%, 300%, 325%, 350%, 375%, 400%, 425%, 450%, 475%, 500% or increments in between those recited. These amounts are not meant to be limiting, and increments between the recited percentages are specifically envisioned as part of the disclosure. In some embodiments, the perception of sweetness intensity of the sweetener is enhanced by up to 25%. In other embodiments, the perception of sweetness intensity of the sweetener is enhanced by up to 50%. In other embodiments, the perception of sweetness intensity of the sweetener is enhanced by up to 75%. In other embodiments, the perception of sweetness intensity of the sweetener is enhanced by up to 100%. In some embodiments, the perception of sweetness intensity of the sweetener is enhanced by about 5%-about 100%, about 5%-about 90%, about 5%-about 80%, about 5%-about 70%, about 5%-about 60%, about 5%-about 50%, about 5%-about 40%, about 5%-about 30%, about 10%-about 30%, about 10%-about 25%, about 20%-about 80%, about 20%-about 70%, about 20%-about 60%, about 20%-about 50%, about 20%-about 40%, about 20%-about 30%, about 25%-about 80%, about 25%-about 70%, about 25%-about 60%, about 25%-about 50%, about 25%-about 40%, or about 25%-about 30%. These amounts are not meant to be limiting, and increments between the recited percentages are specifically envisioned as part of the disclosure.

In some embodiments, the method of enhancing the sweet taste attributed to a sweetener in an edible composition further comprises adding at least one additional additive, such as a sweet taste improving composition, and/or a sweet taste improving additive.

Method of Enhancing Activation of a Sweet Taste Receptor

Another aspect of the disclosure provides a method of enhancing or potentiating activation and/or signaling of a sweet taste receptor. In some embodiments, the method comprises contacting a sweet taste receptor with a flavor-grade sweet modulating compound according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, in the presence of a sweetener.

In some embodiments, the method comprises contacting a sweet taste receptor with an edible composition comprising a flavor-grade sweet modulating compound according to Formula (I), or a comestibly or biologically acceptable salt, solvate, or enantiomer thereof, or any one of flavor-grade Compounds 1-6, or a comestibly or biologically acceptable salt or solvate thereof; or a combination of any of the foregoing compounds, in the presence of a sweetener. The edible composition may be a food product, a pharmaceutical composition, or a consumer product. In such methods, an amount of solubilizing agent may also be present in the edible composition, as described herein.

In various embodiments, the sweet taste receptor is an ex vivo or in vivo receptor present in, for example, an assay. The sweet taste receptor also may be an in vivo receptor present in a subject. In such embodiments, the sweet taste receptor is typically present in the oral cavity or gastrointestinal tract of the subject. In some embodiments, the sweet receptor is in the oral cavity of a human. Alternatively, the sweet receptor is in the oral cavity of a non-human animal, such as an animal model.

An in vivo sweet responsive assay means an assay where an assessment of increased perception of sweetness can be ascribed. Such an assay may be, for example, but not limited to, a human sensory descriptive analysis panel, a human sensory discriminative panel, and/or an expert flavorist assessment. Non-human assessments of sweet response include, but not limited to, operant conditioned animal studies of sweetness taste perception and/or lick rate/amount bottle preference tests An in vitro sweet responsive assay refers to an assay where an assessment of increased sweet response or interaction can be ascribed. An example of such an assay may be, but is not limited to, in vitro receptor binding assays, in vitro receptor cell-based assays, and/or electronic tongue taste analysis.

In some embodiments, enhancement of a sweet taste receptor activation will affect a physiological process or condition. Non-limiting examples of physiological processes and conditions affected by the enhancement of sweet taste receptor activation include sweet taste, effects on the gastrointestinal tract, appetite, nutrition, nutrient absorption, satiety, hunger, diabetes, obesity, blood glucose levels, blood glucose regulation, metabolism, diet, and eating disorders.

Methods and Preparations for Blocking or Masking Unpleasant Taste

In addition to sweetness modulation, flavor-grade, compounds of Formula (I), flavor-grade Compounds 1-6 or any of the foregoing compounds, can be suitable for masking or reducing an unpleasant taste sensation, in particular a bitter taste sensation of a bitter-tasting substance. Flavor-grade compounds of Formula (I), flavor-grade Compounds 1-6 or combinations of any of the foregoing compounds, can both synergistically enhance the sweet taste sensation of sweeteners like steviolglycosides (for example occurring naturally in Stevia ssp.) and mask or reduce the bitter taste sensation of such steviolglycosides or other bitter tasting sweeteners such as acesulfame-K, saccharin, steviosides, or rebaudiosides. Preparations comprising the flavor-grade, bitter blocking compounds, or the combination of flavor-grade bitter blocking compounds of the disclosure can be made in the same or similar manner and concentration as the preparations comprising the sweet taste enhancing preparations of the disclosure.

Preparation of the Compounds of the Invention

In one embodiment, flavor-grade Compounds 1-6, or combinations of these compounds, are prepared by the multi-step sequences described below. One of skill in the art would be able to readily adapt the described conditions for the synthesis of any of the compounds of Formula (I).

The flavor-grade compounds of Formula (I) were generated by a reaction between an aryl alcohol (e.g., orcinol) and trans-ferulic acid catalyzed by a natural acid or a combination of natural acids (Scheme 1). The natural acids were selected from oxalic acid, malic acid, tartaric acid, hydrochloric acid, phosphoric acid, benzoic acid, formic acid, maleic acid, pyruvic acid, lactic acid, or a combination thereof. The reactions were heated to between 25° C. to 220° C. for a reaction time of 30 minutes to 24 hours. Reactions were typically conducted at 110° C. to 150° C. for 30 minutes to 1.5 hours. Preferably, reactions were conducted at 150° C. for one hour.

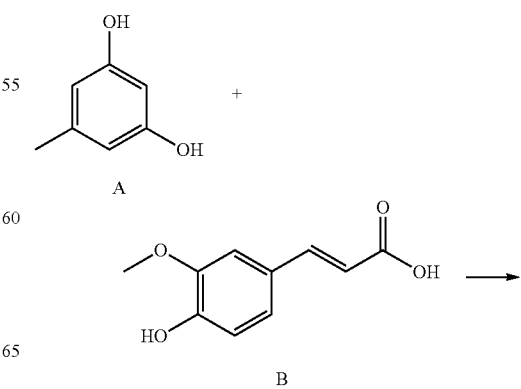

Scheme 1

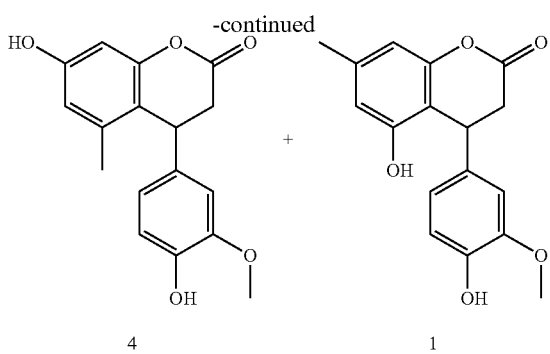

Orcinol (A) was extracted from curculigo orchioides. Extraction of orcinol from curculigo orchioides yielded orcinol glucosides. These glucosides were then deglycosylated through one of two ways, enzymatically through reaction with a glucosidase or through reaction with tartaric acid. The deglycosylated orcinol was then purified. Orcinol (A) can also be extracted from different lichens, including Roccella tinctoria, Lecanora, Roccella fuciformis, Roccella pygmaea, Roccella phycopsis, Lecanora tartarea, Variolaria dealbata, Ochrolechia parella, Parmotrema tinctorum, Parmelia, Roccella montagnei, and Dendrographa leucophoea, or from oakmoss (Evernia prunastri), treemoss (Pseudevernia furfuracea), or aloes.

Trans-ferulic acid (B) was extracted from cereal bran and purified.

Reaction 1

Orcinol from a natural source (1.0 grams) and trans-ferulic acid from a natural source (0.8 grams) were heated in an enclosed scintillation vial with L-malic acid from a natural source (2 grams) and L-(+)-tartaric acid from a natural source (2 grams) at 150° C. for one hour. The reaction mixture was poured into 200 mL brine and extracted with 200 mL ethyl acetate. The organic phase was then washed again with 100 mL brine, dried over sodium sulfate and concentrated by evaporation. The solid was washed again with 100 mL water overnight to recover orcinol. After filtration, the solid was dissolved in ethanol and was chromatographed to give 200 mg pure flavor-grade Compound 1 (yield was 16%).

Reaction 2

Orcinol from a natural source (1.0 grams) and trans-ferulic acid from a natural source (0.8 grams) were heated in an enclosed scintillation vial with L-malic acid from a natural source (2 grams) and L-(+)-tartaric acid from a natural source (2 grams) at 150° C. for one hour. The reaction mixture was poured into 200 mL brine and extracted with 200 mL ethyl acetate. The organic phase was then washed again with 100 mL brine, dried over sodium sulfate and concentrated by evaporation. The solid was washed again with 100 mL water overnight to recover orcinol. After filtration, the solid was lyophilized to give about 900 mg (yield is 73%) of a mixture of flavor-grade Compounds 1-6 ((±) 5-hydroxy-4-(4-hydroxy-3-methoxyphenyl)-7-methylchroman-2-one and (±) 7-hydroxy-4-(4-hydroxy-3-methoxyphenyl)-5-methylchroman-2-one at a 1:2 molar ratio).

Reaction 3

The orcinol from a natural source was released from orcinol glucoside: Orcinol glucoside (5 grams) in 20% of aqueous tartaric acid (50 mL) was heated at 100° C. for 1.5 days. The mixture was cooled down and extracted with ethyl acetate (100 mL×2). The combined organic layers were washed with water, brine, dried over sodium sulfate and concentrated, and the residual obtained was used in the next step without further purification.

Orcinol from a natural source (1.0 grams) and trans-ferulic acid from a natural source (0.8 grams) were heated in an enclosed scintillation vial with L-malic acid from a natural source (2 grams) and L-(+)-tartaric acid from a natural source (2 grams) at 150° C. for one hour. The reaction mixture was poured into 200 mL brine and extracted with 200 mL ethyl acetate. The organic phase was then washed again with 100 mL brine, dried over sodium sulfate and concentrated by evaporation. The solid was washed again with 100 mL water overnight to recover orcinol. After filtration, the solid obtained was dissolved in ethyl acetate and passed through a layer of silica gel. The fractions were concentrated, and the residue was solidified with ether, washed with ether to afford the desired product, a mixture of flavor-grade Compounds 1-6 (120 mg, (±) 5-hydroxy-4-(4-hydroxy-3-methoxyphenyl)-7-methylchroman-2-one and (±) 7-hydroxy-4-(4-hydroxy-3-methoxyphenyl)-5-methylchroman-2-one at a 2:1 molar ratio).

Reaction 4

The orcinol from a natural source was released from orcinol glucoside by action of β-glucosidase: Orcinol glucoside was diluted in 100 mL of 100 mM sodium acetate buffer, pH 5 (final concentration of substrate—35 mM). β-D-glucoside glycohydrolase from almonds (EC 3.2.1.21; Sigma-Aldrich) was added to the solution at concentration 1-20 U/μMole of substrate. The de-glycosylation reaction was carried out under agitation at 100 rpm at 37° C. until completion. The broth was mixed with acetonitrile and separated into two layers under −12° C. The organic layer was dried over sodium sulfate and concentrated, and the residual (1.7 grams) obtained was used in the next step without further purification.

Orcinol from a natural source (1.0 grams) and trans-ferulic acid from a natural source (0.8 grams) were heated in an enclosed scintillation vial with L-malic acid from a natural source (2 grams) and L-(+)-tartaric acid from a natural source (2 grams) at 150° C. for one hour. The reaction mixture was poured into 200 mL brine and extracted with 200 mL ethyl acetate. The organic phase was then washed again with 100 mL brine, dried over sodium sulfate and concentrated by evaporation. The solid was washed again with 100 mL water overnight to recover orcinol. After filtration, the solid was lyophilized to give about 900 mg (yield is 73%) of a mixture of flavor-grade Compounds 1-6 ((±) 5-hydroxy-4-(4-hydroxy-3-methoxyphenyl)-7-methylchroman-2-one and (±) 7-hydroxy-4-(4-hydroxy-3-methoxyphenyl)-5-methylchroman-2-one at a 1:2 molar ratio).

Purification Conditions

Flavor-grade compound 2 was purified with a 330 g column with 0% to 40% ethyl acetate in hexane to give 23.6 g of a mixture of two regioisomers (1:1 ratio by LC-MS). The solid mixture was taken up in DMSO and separated by HPLC using a preparative C18 column (250 mm×50 mm, Xbridge, Waters, USA) with an isocratic gradient of water/acetonitrile (60/40, v/v, 0.1% formic acid added to water) at 100 mL/min flow rate. The desired regioisomer was collected between 6.5 minutes and 7.5 minutes. Pure fractions were combined and evaporated under vacuum to remove acetonitrile. The aqueous suspension was extracted with ethyl acetate twice. Combined organic phase was dried over sodium sulfate and evaporated under vacuum to give Compound 1 as white solid. LC-MS (retention time: 2.28 min, 301 [M+1]). $^1$H NMR (DMSO-D$_6$): 9.87 (s, 1H), 8.92 (s, 1H), 6.80 (d, J=1.9 Hz, 1H), 6.64 (d, J=8.0 Hz, 1H), 6.51 (s, 1H), 6.46 (s, 1H), 6.32 (dd, J=8.1, 2.0 Hz, 1H), 4.44 (d, J=6.1 Hz, 1H), 3.72 (s, 3H), 2.84-3.19 (m, 2H), 2.26 (s, 3H).

2.83 g of racemic sample of Compound 1 was separated by SFC chiral chromatography to provide 1.3 g of enantiomer, Compound 2 (chiral column: CHIRALPAK AD-H 25×3 cm, isopropanol/CO$_2$ (20/80), 100 bar, flow rate: 31.5 mL/min) with >98% ee, Compound 2 $[\alpha]^{20}_D$=+20 (c=1.0 mg/mL, ethanol). Compound 2 is (+)-5-hydroxy-4-(4-hydroxy-3-methoxyphenyl)-7-methylchroman-2-one and was determined to be (R)-5-hydroxy-4-(4-hydroxy-3-methoxyphenyl)-7-methylchroman-2-one by crystallography. Compound 3 is (−)-5-hydroxy-4-(4-hydroxy-3-methoxyphenyl)-7-methylchroman-2-one and was determined to be (S)-5-hydroxy-4-(4-hydroxy-3-methoxyphenyl)-7-methylchroman-2-one by crystallography.

EXAMPLES

Example 1

2 Alternative Forced Choice

Effect of Test Compounds on the Perception of Sweet Taste of High Fructose Corn Syrup
(HFCS) Two-alternative Forced Choice Method (2AFC).

The effect of the test compounds and combinations of test compounds on the perception of the sweet taste of a flavored beverage (referred to as Lemon Lime henceforth) of sweetener in humans was evaluated using a two-alternative forced choice "sip and spit" method (2AFC).
Preparation of Samples for Sensory Taste Tests:

The Lemon Lime solutions were prepared by adding sucrose equivalent (SE) quantities of high fructose corn syrup (HFCS) (by weight), to water to achieve the desired concentration. The lemon lime pH is 3.1. Compounds were first prepared as a 500-fold concentrated stock solution in 100% ethanol. These concentrated stocks were then added to the aqueous sweetener solutions to result in a final ethanol concentration of 0.2%. The control (positive and negative) samples were also normalized to 0.2% ethanol. This level of ethanol was not seen to contribute any perceived sweetness.
Sensory Methodology: Assessment of Sweetness Perception Using 2AFC Method The 2AFC test used for compound evaluation was a double blinded and randomized test where taste panelists (n≥15) evaluate a pair of sweetener solutions at a time—one sample contains aqueous sweetener solution plus compound (i.e. test) while the other contains aqueous sweetener solution at higher concentration without compound (i.e. positive control). Each test sample was compared against a positive control. For example, if the test sample contained 1× sweetener concentration with compound (e.g. 5brix HFCS with compound), the positive control sample contained a 1.1× sweetener concentration (e.g. 5.5brix HFCS without compound). In this manner, compounds were not assessed simply for an increase in perceived sweetness, but a significant increase in perceived sweetness above the positive control.

Panelists were instructed not to eat or drink (except water) for at least 1 h before the test. During the test, panelists were instructed to sip each sample, swirl it around their mouth and then expectorate. After tasting each sample in the pair, panelists were instructed to record the sample that is "sweeter" in taste. Panelists cleansed their palates by rinsing with water, eating a cracker and waiting for an interval of about 5 minutes. All samples were tasted at ambient temperatures. Data were analyzed using binomial probabilities. The results of the 2AFC analysis are presented in Table 1, below.

TABLE 1

Sensory Data Summary 2AFC assessment of increase in perceived sweetness

| Compound No. | Sweetner Concentration for Compound Containing Sample (Test sample) | Sweetener Concentration of positive control surpassed by test sample | Compound concentration with positive 2AFC results (ppm) | Fold increase in perceived sweetness |
|---|---|---|---|---|
| 1 | 7.14brix HFCS | 10brix HFCS | 25 | >1.4X |
| 1 & 4 (2:1 molar ratio) | 7.14brix HFCS | 10brix HFCS | 41.25 | >1.4X |

Approximate levels of sweetness enhancement in column 5 of Table 1 were calculated as follows:
Approximate levels of sweetness enhancement=Sweetener concentration of positive control surpassed by the test sample, divided by sweetener concentration for compound-containing sample (e.g. 1.5×=7.5brix HFCS/5brix HFCS). This only indicates that the perceived increase is greater than the positive control, but does not indicate the degree with which the positive control concentration was surpassed.

Compounds and combinations of compounds of the disclosure can be also be tested by methods included in U.S. provisional application 62/102,790, the disclosure, data and methods of which are incorporated herein by reference.

What is claimed is:
1. A composition comprising a sweetener and a flavor-grade compound wherein said compound is one of Compounds 1-3 having the structure:

Compound 1

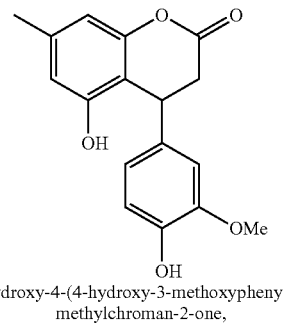

5-hydroxy-4-(4-hydroxy-3-methoxyphenyl)-7-methylchroman-2-one, or a comestibly or biologically acceptable salt, solvate or enantiomer thereof, or Compound 2

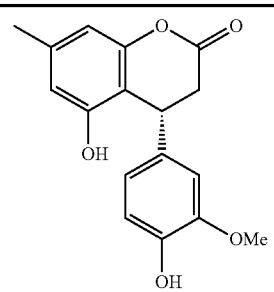

Compound 3

(R)-5-hydroxy-4-(4-hydroxy-3-methoxyphenyl)-7-methylchroman-2-one,

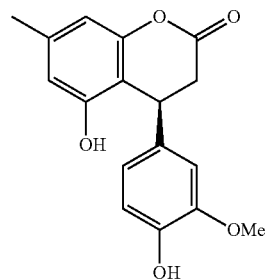 [SMILES: COc1cc([C@@H]2CC(=O)Oc3cc(C)cc(O)c32)ccc1O]

(S)-5-hydroxy-4-(4-hydroxy-3-methoxyphenyl)-7-methylchroman-2-one, or a comestibly or biologically acceptable salt or solvate thereof; or a combination of any of the foregoing compounds.

2. The composition of claim 1, wherein said composition is edible and capable of enhancing the sweet taste of the sweetener.

3. The composition according to claim 1, wherein the sweetener is a caloric sweetener, an artificial sweetener, an artificial high-potency sweetener, a natural high-potency sweetener, a sugar alcohol, a rare sugar, or a combination of any of the foregoing sweeteners.

4. The composition or method of claim 3, wherein the caloric sweetener is a carbohydrate selected from sucrose, high fructose corn or starch syrup, glucose, and fructose.

5. The composition claim 3, wherein the natural high-potency sweetener is a steviol glycoside, rebaudioside A, rebaudioside B, rebaudioside C (dulcoside B), rebaudioside D, rebaudioside E, rebaudioside F, rebaudioside I, rebaudioside H, rebaudioside L, rebaudioside K, rebaudioside J, rebaudioside N, rebaudioside O, rebaudioside M, dulcoside A, rubusoside, stevia leaf extract, a stevioside, a glycosylated steviol glycoside, a mogroside, mogroside V, isomogroside, mogroside IV, Luo Han Guo fruit extract, siamenoside, monatin or any salt thereof (monatin SS, RR, RS, SR), curculin, glycyrrhizic acid or any salt thereof, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, or cyclocarioside I or a mixture of any of the foregoing sweeteners.

6. A method of enhancing the sweet taste of an edible composition, the method comprising adding an effective amount of a flavor-grade composition of claim 1 or a comestibly or biologically acceptable salt, solvate, or enantiomer thereof; or a combination of any of the foregoing compounds, to said edible composition, such that the perception of sweet taste of a sweetener is enhanced.

7. A tabletop sweetener composition comprising the composition of claim 1.

8. A delivery system selected from the group consisting of a co-crystallized flavor composition with a sugar or a polyol, an agglomerated flavor composition, a compacted flavor composition, a dried flavor composition, a particle flavor composition, a spheronized flavor composition, a granular flavor composition or a liquid flavor composition, wherein the flavor composition comprises the composition of claim 1.

9. A food product, beverage composition, consumer product, or pharmaceutical composition comprising the composition of claim 1.

10. The beverage composition of claim 9, wherein said beverage is a non-alcoholic beverage.

11. The beverage composition of claim 9, wherein said beverage composition is selected from a non-carbonated beverage, a carbonated beverage, a cola, a root beer, a fruit flavored beverage, a citrus-flavored beverage, a fruit juice, a fruit-containing beverage, a vegetable juice, a vegetable containing beverage, tea, coffee, a dairy beverage, a sports drink, an energy drink, and enhanced or flavored water.

* * * * *